US011448598B1

(12) United States Patent
Bhartia et al.

(10) Patent No.: US 11,448,598 B1
(45) Date of Patent: Sep. 20, 2022

(54) METHODS AND SYSTEMS FOR DETECTION OF BIOHAZARD SIGNATURES IN COMPLEX CLINICAL AND ENVIRONMENTAL SAMPLES

(71) Applicant: Photon Systems, Inc., Covina, CA (US)

(72) Inventors: Rohit Bhartia, Altadena, CA (US); Michael R. Reid, Newport Beach, CA (US); William F. Hug, Altadena, CA (US); Ray D. Reid, Glendora, CA (US)

(73) Assignee: Photon Systems, Inc., Covina, CA (US)

( * ) Notice: Subject to any disclaimer, the term of this patent is extended or adjusted under 35 U.S.C. 154(b) by 0 days.

(21) Appl. No.: 17/374,902

(22) Filed: Jul. 13, 2021

Related U.S. Application Data

(60) Provisional application No. 63/162,491, filed on Mar. 17, 2021, provisional application No. 63/051,258, filed on Jul. 13, 2020.

(51) Int. Cl.
*G01N 21/64* (2006.01)
*G01N 21/33* (2006.01)
(Continued)

(52) U.S. Cl.
CPC ......... *G01N 21/6486* (2013.01); *G01N 21/33* (2013.01); *G01N 21/359* (2013.01);
(Continued)

(58) Field of Classification Search
CPC .............. G01N 21/6486; G01N 21/33; G01N 21/3577; G01N 21/359; G01N 21/6456;
(Continued)

(56) References Cited

U.S. PATENT DOCUMENTS

| 3,757,250 A | 9/1973 | Packard et al. |
| 5,088,820 A | 2/1992 | Winefordner et al. |

(Continued)

FOREIGN PATENT DOCUMENTS

WO     WO 2021214336 A1 * 10/2021 ............. G01N 21/65

OTHER PUBLICATIONS

Asher, S.A., "Resonance Raman Spectroscopy of Hemoglobin", Methods in Enzymology, vol. 76, (1981): pp. 371-413.
(Continued)

*Primary Examiner* — David P Porta
*Assistant Examiner* — Jeremy S Valentiner
(74) *Attorney, Agent, or Firm* — Dennis R. Smalley

(57) ABSTRACT

Methods, apparatus, and systems provide improved identification of selected biohazard and/or biohazard signatures from complex in vivo or in vitro samples and include deep UV native fluorescence spectroscopic analysis for multiple locations of a sample wherein classification results for individual locations are combined and spatially correlated to provide a positive or negative conclusion of biohazard signature presence (e.g., for signatures for viruses, bacteria, and diseases including SARS-CoV-2 and its variants and COVID-19 and its variants). Improvements include one or more of reduced sample processing time (minutes to fractions of a minute), reduced sampling cost (dollars to fractions of a dollar), high conclusion reliability (rivaling real time RT-PCR). Some embodiments may incorporate a stage or scanning mirror system to provide movement of a sample relative to an excitation exposure location. Some embodiments may incorporate Raman or phosphorescence spectroscopic analysis as well as imaging systems.

23 Claims, 23 Drawing Sheets

(51) Int. Cl.
*G01N 33/569* (2006.01)
*G01N 21/3577* (2014.01)
*G01N 21/359* (2014.01)
*G01N 21/65* (2006.01)
*G01N 21/17* (2006.01)

(52) U.S. Cl.
CPC ..... *G01N 21/3577* (2013.01); *G01N 21/6456* (2013.01); *G01N 21/658* (2013.01); *G01N 33/56983* (2013.01); *G01N 2021/1736* (2013.01); *G01N 2021/6421* (2013.01); *G01N 2021/6423* (2013.01); *G01N 2021/656* (2013.01); *G01N 2201/0221* (2013.01); *G01N 2201/067* (2013.01); *G01N 2201/129* (2013.01)

(58) Field of Classification Search
CPC ........... G01N 21/658; G01N 33/56983; G01N 2021/1736; G01N 2021/6421; G01N 2021/6423; G01N 2021/656; G01N 2201/0332; G01N 2201/067; G01N 2201/129
See application file for complete search history.

(56) References Cited

U.S. PATENT DOCUMENTS

| | | |
|---|---|---|
| 5,194,912 A | 3/1993 | Batchelder et al. |
| 5,442,438 A | 8/1995 | Batchelder et al. |
| 5,465,607 A | 11/1995 | Corrigan et al. |
| 5,623,342 A | 4/1997 | Baldwin et al. |
| 6,002,476 A | 12/1999 | Treado |
| 6,287,869 B1 | 9/2001 | Hug et al. |
| 6,891,618 B2 | 5/2005 | Harju et al. |
| 7,084,972 B2 | 8/2006 | Treado |
| 7,154,595 B2 | 12/2006 | Paldus et al. |
| 7,245,369 B2 | 7/2007 | Wang et al. |
| 7,286,231 B2 | 10/2007 | Maier et al. |
| 7,525,653 B1 | 4/2009 | Hug et al. |
| 7,564,541 B2 | 7/2009 | Tuschel |
| 7,595,473 B2 | 9/2009 | Walt et al. |
| 7,817,273 B2 | 10/2010 | Bahatt et al. |
| 7,956,991 B2 | 6/2011 | Bangalore et al. |
| 8,395,770 B1 | 3/2013 | Hug et al. |
| 8,759,791 B1 | 6/2014 | Hug et al. |
| 9,442,070 B1 | 9/2016 | Hug et al. |
| 10,732,037 B1 | 8/2020 | Reid |
| 2003/0080291 A1 | 5/2003 | Larson et al. |
| 2005/0224781 A1 | 10/2005 | Kneissl et al. |
| 2006/0008866 A1 | 1/2006 | Flick et al. |
| 2007/0081156 A1* | 4/2007 | Treado ...................... G01J 3/10 356/301 |
| 2011/0003279 A1 | 1/2011 | Patel |
| 2020/0158728 A1* | 5/2020 | Robinson ........... G01N 33/6854 |

OTHER PUBLICATIONS

Asher, S.A., "UV Resonance Raman Spectroscopy for Analytical, Physical, and Biophysical Chemistry, Part 1", Anal. Chem., vol. 65, No. 2, (Jan. 15, 1993): pp. 59-66.
Asher, S.A., "UV Resonance Raman Spectroscopy for Analytical, Physical, and Biophysical Chemistry, Part 2", Anal. Chem., vol. 65, No. 4, (Feb. 15, 1993): pp. 201-210.
Asher, S.A., "UV Resonance Raman Studies of Molecular Structure and Dynamics: Applications in Physical and Biophysical Chemistry", Ann. Rev. Phys. Chem., vol. 39, (1988): pp. 537-588.
Asher, S.A., et al., "Development of a New UV Resonance Raman Spectrometer for the 217-400 nm Spectral Region", Rev. Sci. Instr. vol. 54, (Dec. 1983): pp. 1657-1662.
Bhartia, W. F. Hug, E. C. Salas, R. D. Reid, K. K. Sijapati, A. Tsapin, W. Abbey, P. G. Conrad, K. H. Nealson and A. L. Lane, "Classification of Organic and Biological materials with Deep UV Excitation", Applied Spectroscopy, vol. 62, No. 10, Oct. 2008.
Chi, Z., et al., "UV Resonance Raman-Selective Amide Vibrational Enhancement: Quantitative Methodology for Determining Protein Secondary Structure", Biochemistry, vol. 37, (1998): pp. 2854-2864.
Cho, N., and S.A. Asher, "UV Resonance Raman and Absorption Studies of Angiotensin II Conformation in Lipid Environments", Biospectroscopy, vol. 2, (1996): pp. 71-82.
Cho, N., Song, S., and S.A. Asher, "UV Resonance Raman and Excited-State Relaxation Rate Studies of Hemoglobin", Biochemistry, vol. 33, (1994): pp. 5932-5941.
Gregg, S.D., J.L.Campbell, J.W. Fisher, and M.G. Bartlett, "Methods for characterization of Jet Propellant-8: vapor and aerosol", Biomed. Chromatograph. 21, pp. 463-472, Mar. 2007.
Ianoul, A., T. Coleman, and S.A. Asher, "UV Resonance Raman Spectroscopic Detection of Nitrate and Nitrite in Wastewater Treatment Processes", Anal. Chem., vol. 74, pp. 1458-1461, 2002.
McCreery, R.L., "Raman Spectrocopy for Chemical Analysis", John Wiley & Sons, ISBN # 0-471-25287-5, 2000.
Milofsky, R. E., et al., "Native Fluorescence Detection of Nucleic Acids and DNA Restriction Fragments in Capillary Electrophoresis", Anal. Chem., vol. 65, (Jan. 1993): pp. 153-157.
Moon, Raphael P.; Guicheteau, Jason A.; Christesen, Steven D.; Fountain, Augustus W. III; Ginter, Joy; Tokarz, John; Green, Norman; Tripathi, Ashish; Emmons, Erik; and Hung, Kevin, "Preparation of Chemical Samples on Relevant Surfaces Using Inkjet Technology", Apr. 2013, Edgewood Chemical Biological Center; U.S. Army Research, Development and Engineering Command, Aberdeen Proving Ground, MD 21010-5424.
Munro, C.H., V. Pajcini, and S.A. Asher, "Dielectric Stack Filters for Ex Situ and In Situ UV Optical-Fiber Probe Raman Spectroscopic Measurements", App. Spect., vol. 51, No. 11, pp. 1722-1729, 1997.
R. Bhartia, W. F. Hug, E. C. Salas, K. Sijapati, A. L. Lane, R. D. Reid and P.G.Conrad, "Biochemical detection and identification false alarm rate: dependence on wavelength using laser induced native fluorescence", Proc. SPIE, vol. 6218, Orlando, FL. Apr. 2006.
Reid, Michael; Hug, William; and Reid, Ray, "ChemCal, a surface cleaning validation tool for depositing predetermined chemical concentrations, used in the calibration of surface cleaning validation tools.", International Forum on Process Analytical Chemistry, Feb. 14, 2018, Photon Systems Inc.
Reid, Ray, "TraC—A disruptive new hand-held rapid measurement system to verify pharma equipment surface cleanliness", International Forum on Process Analytical Chemistry, Mar. 2, 2017, Photon Systems Inc.
S. A. Asher, C.R. Johnson, "Raman Spectroscopy of a Coal Liquid Shows That Fluorescence Interference Is Minimized with Ultraviolet Excitation", Science, 225, 311-313, Jul. 20, 1984.
Sparrow, M.C., J.F. Jackovitz, C.H. Munro, W.F. Hug, and S.A. Asher, "A New 224nm Hollow Cathode UV Laser Raman Spectrometer", J. App. Spectroscopy, vol. 55, No. 1, Jan. 2001.
Storrie-Lombardi, M. C., W. F. Hug, G. D. McDonald, A. I. Tsapin, and K. H. Nealson. "Hollow cathode ion laser for deep ultraviolet Raman spectroscopy and fluorescence imaging". Rev. Sci. Instruments, 12, 4452-4459, Dec. 2000.
W. H. Hug, R. Bhartia, A.Tsapin, A.L.Lane, P.G.Conrad, K. Sigapati, and R.D. Reid, "Status of Miniature Integrated UV Resonance Fluorescence and Raman Sensors for Detection and Identification of Biochemical Warfare Agents", Proc. SPIE, vol. 5994, p. 5884J1-12, Boston, MA. Oct. 2005.

* cited by examiner (1) Expose the sample to excitation radiation and read resulting emission radiation for a plurality of wavelength bands from each of a plurality of locations on the sample.

▼

(2) On a location-by-location basis, perform a first level analysis to determine which emission radiation readings meet signal threshold requirements relative to background noise readings.

▼

(3) For each emission radiation reading meeting signal threshold requirement, perform a second level membership analysis to assign a class membership to individual location readings indicative of potential relevance to biohazard signature presence.

▼

(4) Perform at least one additional level of analysis involving spatial relationships between a plurality of location readings having class membership potentially relevant to biohazard signature presence wherein a proximity grouping of multiple readings with biohazard signature relevance is used, alone or in combination with other data or analysis, in determining a biohazard signature presence for the sample and thus a biohazard signature presence conclusion for the subject, location, or material.

FIG. 1A

(1) Using one or more test methods of acceptable reliability to determine whether a biohazard signature of interest is present within each of a plurality of different samples which may or may not be correlated to having other similar attributes or coming from sources having similar attributes.

▼

(2) Expose each sample to excitation radiation and read resulting emission radiation for a plurality of wavelength bands from each of a plurality of locations on the sample.

▼

(3) Separate the samples into two or more groups, e.g., biohazard signature positive and biohazard signature negative, and if necessary, further separate the groups into subgroups, such as algorithm training group or calibration group and a testing or verification group. Further divisions may be used based on other common factors or different factors associated with the data.

▼

(4) Use the data from separated sample groups, or such samples and data after further processing or clean-up, as a basis for comparison and classification of spectrum data taken from samples for which a biohazard signature classification is to be made as in element (3) of FIG. 1A. If necessary, prior to using the separated data for correlation purposes, it may be used for training and testing algorithms, e.g., (a) to verify algorithm reliability against false negatives and/or false positives within a desired maximum error tolerance, or (b) to yield reliable conclusions that are maximized or are within acceptable ranges that balance indeterminate results with false positives and/or false negatives.

FIG. 1B

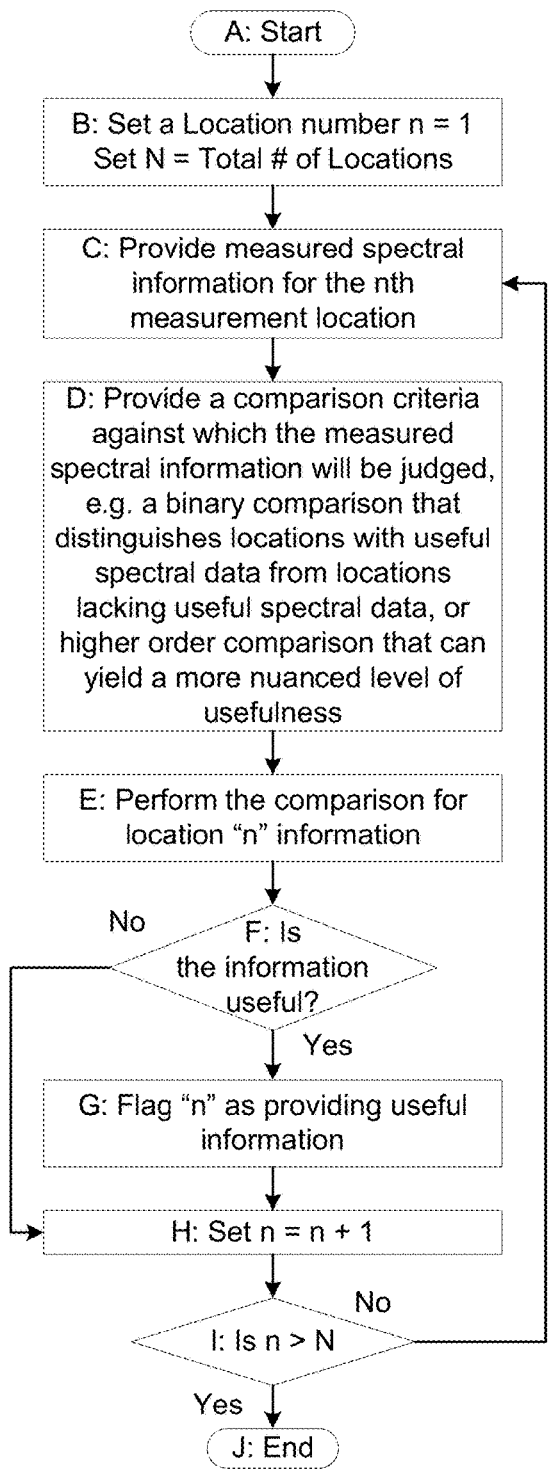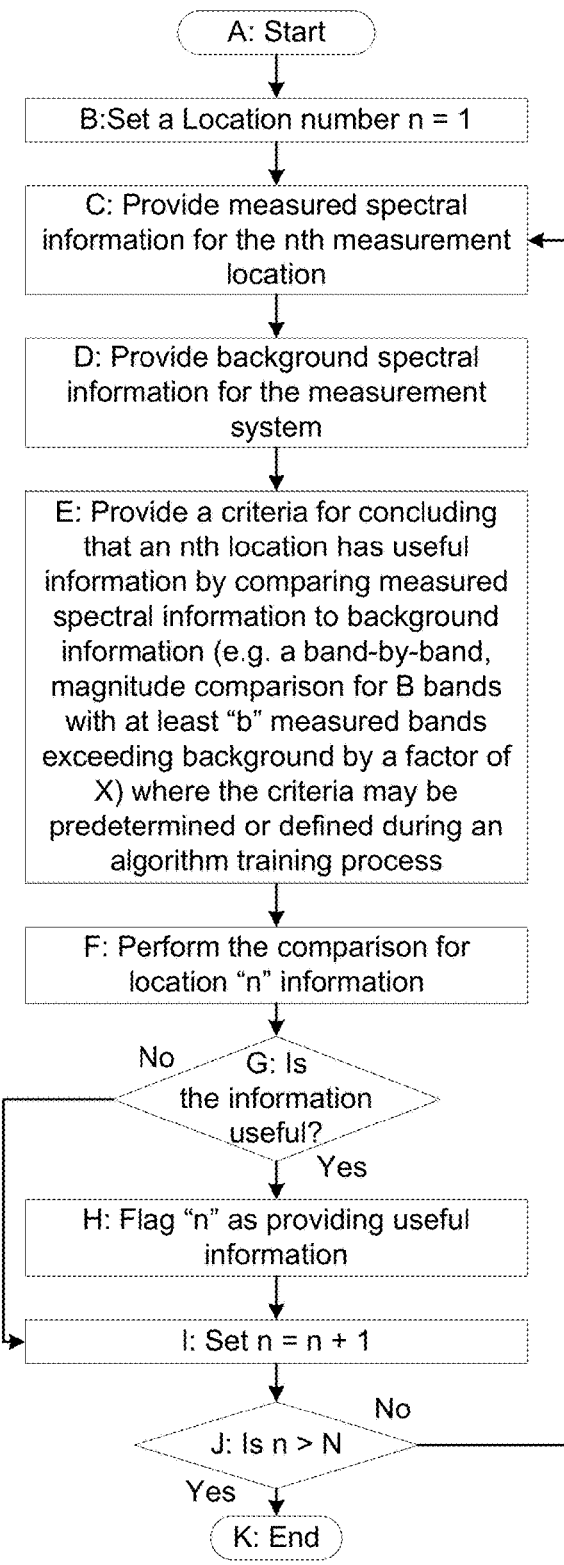
FIG. 2B1
FIG. 2B2

Predetermined Signature/Signal Information Examples

A: Provided on a wavelength-band-by-wavelength-band basis using raw or normalized data and from a plurality of locations from each of a plurality of different samples that are flagged with predetermined signature conclusions and possibly supplemental sample source information B: Provided on a wavelength-band-by-wavelength-band selected ratio basis using raw or normalized data from a plurality of locations from each of a plurality of different samples that are flagged with predetermined signature conclusions and possibly supplemental sample source information

FIG. 2C1

Predetermined Signature/Signal Information Form Examples

A: Band-by-band group of relationships (e.g. equations) bridging normalized emission values for different categories of predetermined signature conclusions (with or without use of supplemental samples)

B: Band-by-band low range and high range numbers with or without outliers removed C: Band-by-Band Values or Selected Band-by-Band Ratio Values 1. Raw data
2. A mode
3. Normalized data
4. A mean
5. A median
6. A midpoint of a range
7. A midpoint of a range with outliers removed
8. A low range number or high range number with or without outliers removed D: Band-by-band set of normalized detection values that are deemed closer to the predetermined known biohazard containing and/or to the known non-biohazard containing groups E: Band-by-band set of normalized ratio values that are deemed closer to the predetermined known biohazard containing and/or to the known non-biohazard containing groups F: Band-by-band values or selected ratio values along with at least one value indicative of range 1. 1 – 10 standard deviations
2. A high, or plus, range number
3. Both high and low range numbers
4. A low, or minus, range number
5. A full range number with or without outliers removed

FIG. 2C2

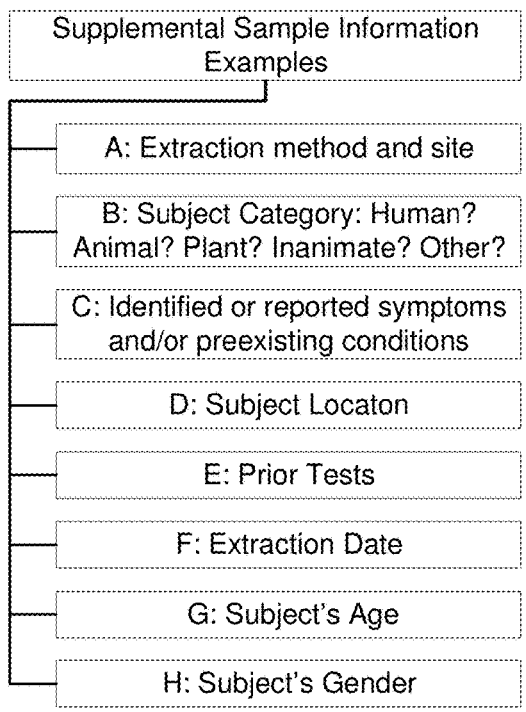
FIG. 2C3
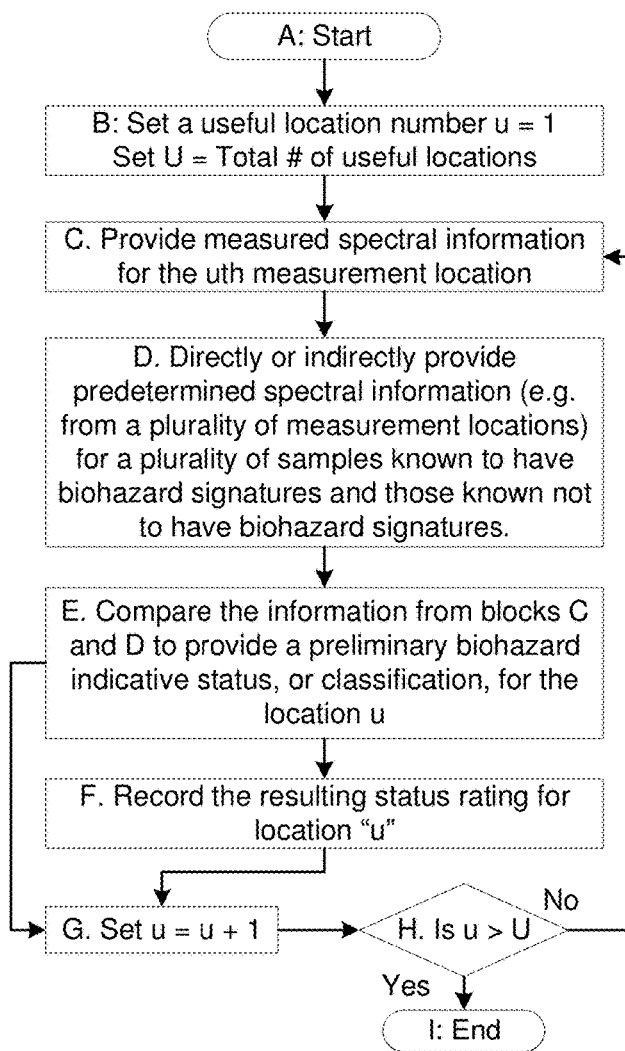
FIG. 2D1
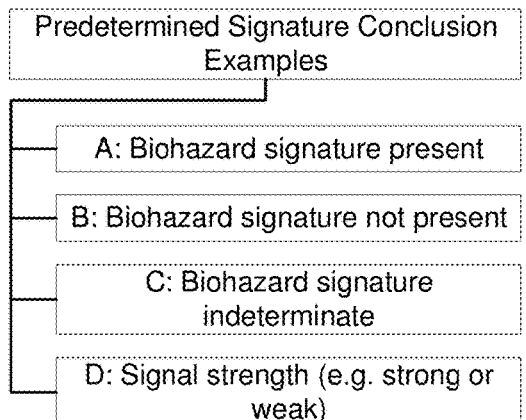
FIG. 2C4
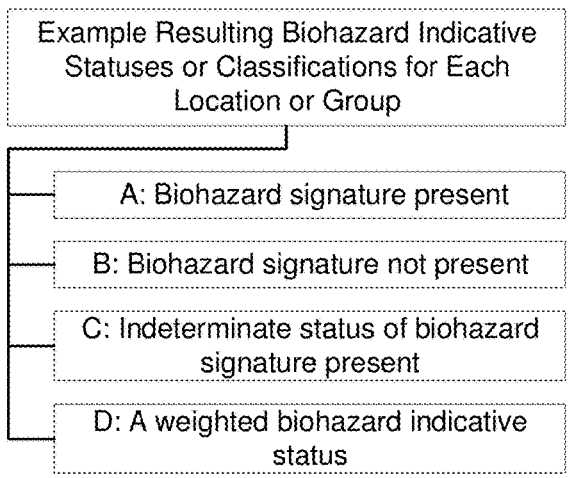
FIG. 2D2

Example Algorithms/Methods for Performing Block E of FIG. 2D1

A. Example 1: For each of at least a selected plurality of the bands b, comparing the measured spectral information to those of the samples with known signatures and determining if the spectral information of the measured sample is generally closer to that of the samples with predetermined biohazard signatures or those with non-biohazard signatures and labeling the band b with a corresponding biohazard status. Then combining the corresponding biohazard status for each selected band b to provide a biohazard indicative status or classification for the location (i.e. group of bands b, associated with location u).

B. Example 2: A process similar to that of Example 1 but using calculated ratio of spectral information associated with each selected band b and another band from the measured sample to a corresponding ratio of bands from the samples with known signatures and determining if the ratio of the measured sample is generally closer to that of the samples with predetermined biohazard signatures or those with non-biohazard signatures and labeling the band b with a corresponding biohazard status. Then combining the corresponding biohazard status for each selected band b to provide a biohazard indicative status or classification for the location.

C. Example 3: A process similar to those of Examples 1 or 2 but where higher order comparisons (i.e. comparisons that look at more than a biohazard signature presence or non-presence from the samples with predetermined biohazard signature status). In such higher order comparisons, the comparisons may be made in a single level that result in classification conclusions or they may occur in multiple levels with each level confirming, modifying, or fine tuning preliminary findings associated with the prior levels.

D. Example 4: A process that may use some features and data processing associated with Examples 1 – 3 but in addition, using a selected artificial intelligence (AI) or machine learning (ML) algorithm that is trained and verified with the information including the known attributes of the predetermined samples such that when the measured data associated with specific locations of samples undergoes analysis, the trained algorithm produces results that are consistent with training data and meets requirements associated with limiting false positives and false negatives.

E. Example 5: A process that uses the method of Example 4 but with the AI or ML algorithm including an instance-based algorithm such as, for example: a K Nearest Neighbor (KNN) algorithm, a Learning Vector Quantization (LVQ) algorithm, a Self-Organizing Map (SOM) analysis, a Locally Weighted Learning (LWL) analysis, or a Support Vector Machines (SVM) analysis.

F. Example 6: A process that uses the method of Example 4 but with the AI or ML algorithm including a dimensionality reduction algorithm, such as, for example: a Principal Component Analysis (PCA), a Principal Component Regression (PCR), a Partial Least Squares Regression (PLSR), or a Discriminant Analysis (DA).

G. Example 7: A process that uses the method of Example 4 but with the AI or ML algorithm including a regression analysis such as, for example: an Ordinary Least Squares Regression (OLSR) analysis, a Linear Regression analysis, a Logistic Regression analysis, a Stepwise Regression analysis, a Multivariate Adaptive Regression Splines (MARS) analysis, or a Locally Estimated Scatterplot Smoothing (LOESS) analysis.

FIG. 2D3

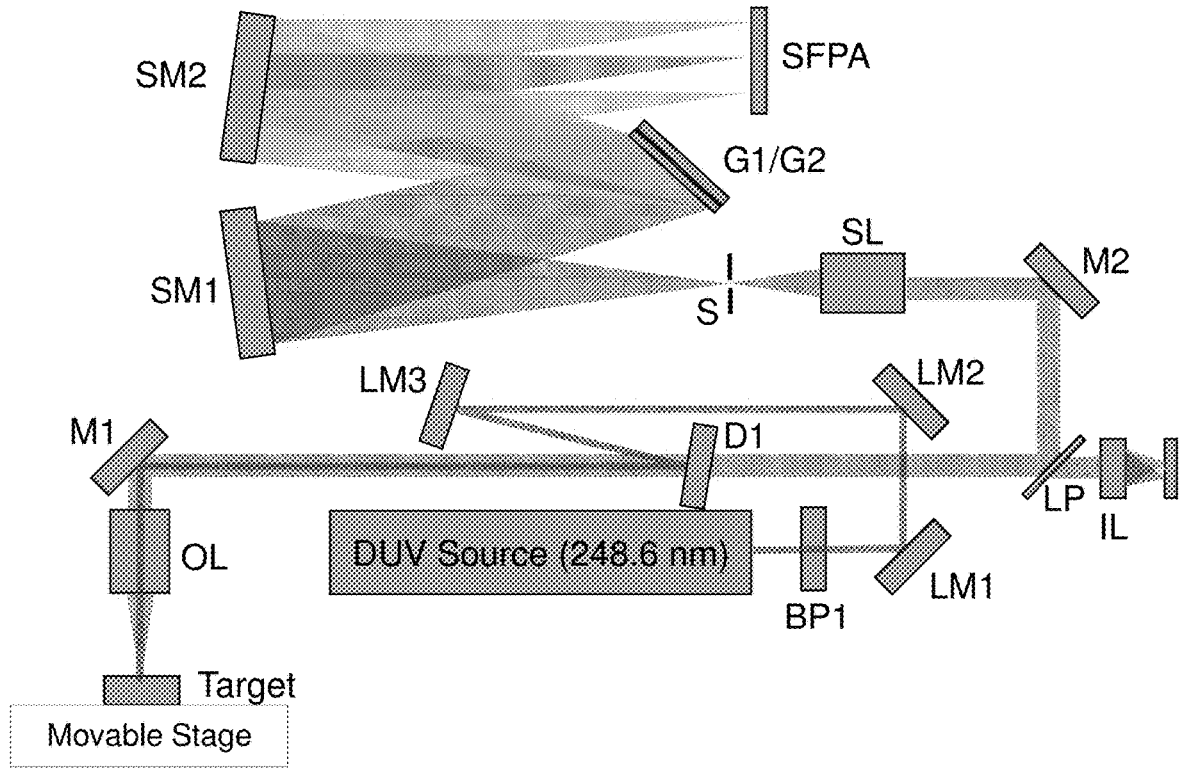

| Element | Description |
|---|---|
| Target | Static or Scanned Surface/Fluid |
| OL | Objective Lens |
| M1/M2 | Broadband UV-Vis Mirror |
| D1 | Dichroic for Laser Injection and Fluorescence/Raman Transmission |
| LP | Longpass for VIS/NIR Context Imaging |
| IL | Imaging Relay Lens |
| IFPA | Imaging Focal Plane Array for Contextual Imaging of Target |
| SL | Spectrometer Lens |
| S | Slit |
| SM1/SM2 | Spectrometer Mirrors |
| G1/G2 | UV Raman/Fluorescence Gratings |
| SFPA | Spectrometer Focal Plane Array |
| BP1 | Narrow Bandpass Filter for Laser Clean-Up |
| LM1/LM2/LM3 | Laser Mirror for 248.6 nm |

FIG. 25

METHODS AND SYSTEMS FOR DETECTION OF BIOHAZARD SIGNATURES IN COMPLEX CLINICAL AND ENVIRONMENTAL SAMPLES

RELATED APPLICATIONS

This application claims priority to the applications set forth in the following table with each such priority application being incorporated herein by reference:

| Docket No. App No. & App. Date Pat. No. & Pat. Date | Inventors, "Title" |
|---|---|
| HR-014-B 63/162,491 - Mar. 17, 2021 | Bhartia, et al., "Methods and Systems for Detection of Biohazard Signatures (e.g. Pathogen Signatures in Complex Clinical and Environmental Samples)" |
| HR-014-A 63/051,258 - Jul. 13, 2020 | Bhartia, et al., "Methods and Systems for Detection of Biohazard Signatures (e.g. Pathogen Signatures) in Complex Clinical and Environmental Samples" |

This application is also related to the following applications which are also incorporated herein by reference.

| Docket No. App No. & App. Date Pat. No. & Pat. Date | Inventors, "Title" |
|---|---|
| HR-003 60/616,269 - Oct. 5, 2004 | Hug, William et al., "Targeted Chemical Analysis Methods and Apparatus" |
| HR-007 11/245,486 - Oct. 5, 2005 7,525,653 - Apr. 28, 2009 | Hug, William et al., "Spectroscopic Chemical Analysis Methods and Apparatus" |
| HR-007-CIP1 12/545,772 - Aug. 21, 2009 8,395,770 - Mar. 12, 2013 | Hug, William et al., "Spectroscopic Chemical Analysis Methods and Apparatus" |
| HR-008 61/118,591 - Nov. 28, 2008 | Hug, William et al., "Native Fluorescence Detector for Naphthalene and Other Volatile Organic Compound Vapors" |
| HR-009 12/628,205 - Nov. 11, 2009 8,759,791 - Jun. 24, 2014 | Hug, William et al., "Native Fluorescence Detection Methods And Detectors For Naphthalene and/or Other Volatile Organic Compound Vapors |
| HR-009-CNT4F 16/688,894 - Nov, 19, 2019 10,890,533 - Jan 12, 2021 | Hug, William et al., "Spectroscopic Chemical Analysis Methods and Apparatus" |
| HR-009-CIP1-5 17/013,469 - Sep. 4, 2020 | Hug, William et al., "Native Fluorescence Detection Methods, Devices, and Systems for Organic Compounds" |
| HR-009-CIP2-3 16/820,309 - Mar. 16, 2020 10,895,533 - Jan. 19, 2021 | Hug, William et al., "Native Fluorescence Detection Methods, Devices, and Systems for Organic Compounds" |
| HR-013-B 16/904,471 - Jun. 17, 2020 11,022,490 - Jun. 1, 2021 | Reid, Michael et al., "Methods and Apparatus for Spectroscopic Identification and/or Calibrated Quantification of Surface Concentration of Materials" |

FIELD OF THE INVENTION

This invention relates to the field of spectroscopic methods and instruments for detecting biohazard signatures (e.g. biohazards themselves, materials produced by biohazards during an infection or infliction, or an immunological response to a biohazard exposure), and more particularly to the field of the rapid, reagentless detection of selected biological hazard signatures (e.g. related to SARS-CoV-2 or COVID-19 or their variants) in samples and even in complex samples with many interferent or confusant materials that may be taken from a particular sampling location in or on a body of a living subject, read directly from such subject without sample extraction, and/or read from samples extracted from environmental materials or directly from an environmental location without sample extraction. Potential environmental locations and/or subject locations at the time of sample extraction or direct reading include, for example, clinical settings (e.g. hospitals, clinics) or field operation settings (e.g. at ports of entry), transportation hubs, transportation carriers (cars, buses, trains, airplanes, ships and the like), government facilities, theatres, lecture halls, schools, churches, amusement parks, event locations, convention centers, sporting events, manufacturing locations, work facilities, restaurants, and lecture halls, as well as in other small, medium, or large events or gathering locations whether indoors or outdoors, as well as general environmental settings whether from surfaces, air, or water.

BACKGROUND OF THE INVENTION

Biohazards, and particularly biological pathogens, have been and will continue to cause local and worldwide health, social, and economic problems. Their spread has become quicker and more globalized with modern travel and connectivity. Pandemics from such biohazards have drastically impacted communities, countries, and relationships as a result of illness, personal loss, death, and fear of infection/illness. Many pathogens can have serious effects on those with weak immune systems or genetic susceptibility, while presenting a lower risk to individuals or groups with more effective immune systems. Periodically, pathogens can occur (e.g., via mutation or reintroduction) that are sufficiently different from anything previously experienced that infected persons are incapable of effectively fighting them which may in turn lead to local epidemic or even pandemic spread with potentially serious and widespread medical, social, and economic consequences.

While awaiting the development and distribution of effective treatments (e.g., vaccines or medical treatment, or cures), limiting the spread of such pathogens can minimize the impact of the pathogen on a broader population. While isolation or quarantining are effective ways of limiting such spread, without a clear understanding of who, or what, has been exposed, guaranteed effectiveness can only be achieved by excessive application of such quarantining with numerous associated negative impacts.

Present methods of detection include the nucleic acid based reverse transcriptase (RT) polymerase chain reaction (PCR) or the more recent evolution, real time RT-PCR, considered the gold-standard method for both viral and microbial detection, and a variety of immunoassay detection methods including enzyme-linked immunosorbent assay (ELISA) and related hybridization array methods. Although considered to be the gold standard, RT-PCR has many shortfalls, including: (1) need for highly skilled personnel to both extract and process samples; (2) need for reagents which have limited shelf lifetime and highly restrictive handling and storage requirements throughout the supply chain including storage at −15 C to −25 C in dark conditions; (3) typically long cycle time from sample collection to receipt of results by the patient or health-care worker, typically several days; (4) due to the high specificity of this method, mutated pathogenic strains go undetected until a new test and a new set of PCR reagents is developed, which can take months to develop and even more months to deploy; (5) high cost per test, typically between $30 and $100 for reagent kit only, not including labor and related cost for reagent kit handling, sample collection, and sample handling; and (6) RT-PCR does not identify if a patient has been previously exposed to some biohazards (e.g. SARS-CoV-2).

Although faster to process (<10 minutes) and potentially less expensive (<$20), the antibody testing method ELISA and related immunoassay tests measure the presence of the antigens IgM and IgG which can trigger on COVID-19 infections and other viral infections such as influenzas or strep. The ELISA method measures both IgM and IgG and is important since it can identify whether a patient is potentially in the process of infection or has had a prior infection. However, it does not indicate a patient is currently infected. Both RT-PCR and immunoassay tests are best taken together. Storage and handling restrictions are not as severe with ELISA test kits compared to RT-PCR test kits. As the test requires specificity to the pathogen, development of these antibodies require months after the emergence of a new pathogen.

Minimization of, or at least reduction of, negative impacts are possible particularly if improved, and more expansive testing can be performed which may provide for more rapid intervention, more appropriate isolation or non-isolation decisions, and more rapid development of solid epidemiological data on biohazard (e.g. viral) prevalence which may be used for the implementation and adjustment of measures to restrict viral spread.

A need exists for improved testing methods, apparatus, and systems for identifying the presence of selected biohazards or biohazard signatures on inanimate objects as well as on living subjects that may have been exposed, those that are currently infected, those that were previously infected, and/or those that have developed an immunity to the biohazard. Improvements may include one or more of: (1) reduced testing time, (2) reduced processing time for obtaining test results (e.g. from days to minutes or less), (3) results with fewer false positives, (4) results with fewer false negatives, (5) lower cost of testing equipment, (6) lower cost of obtaining samples and processing such samples (e.g. from many tens of dollars or even one hundred plus dollars per test to a few tens of dollars, a few dollars, or even a fraction of a dollar per test), (7) more portability of testing equipment, (8) removal of a need for test reagents let alone different reagents for different biohazard signatures, (9) ability to use a single sample to provide a data set or multiple data sets capable of providing results for multiple biohazards either in parallel, or in series, or even weeks, months, or years after sample reading occurred, (10) a testing method that does not degrade or destroy the sample, and (11) making testing methods less prone to operator error and even reduced operator skill requirements.

SUMMARY OF THE INVENTION

It is an object of some embodiments of the invention to provide an improved method, apparatus and/or system for identifying the presence of selected biohazards or biohazard signatures from samples (e.g., complex samples) wherein the improvement provides one or more of:

(a) reduced testing time,
(b) reduced processing time for obtaining test results (e.g., from days to minutes or less),
(c) results with fewer false positives compared to systems with similar processing times or testing cost,
(d) results with fewer false negatives compared to systems with similar processing times or testing cost,
(e) lower cost of testing equipment,
(f) lower cost of obtaining samples and processing such samples (e.g., from many tens of dollars or even one hundred plus dollars per test to a few tens of dollars, a few dollars, or even a fraction of a dollar per test),
(g) more portability of testing equipment,
(h) removal of a need for consumable test reagents, let alone different reagents for different biohazard signatures,
(i) ability to use a single sample to provide a data set capable of providing results for multiple biohazards either substantially in parallel (i.e. where processing associated with more than one biohazard analysis occurs with some temporal overlap and wherein the results for the multiple biohazards are provided more quickly than would be possible if the individual analyses were performed one after the other), or in series, or even weeks, months, or years after sample reading occurred,
(j) maintenance of sample integrity that allows additional testing or different testing to occur, and/or
(k) testing methods less prone to operator error and even having reduced operator skill requirements.

Other objects are more specifically directed to detecting presence of, or lack of presence of, SARS-CoV-2, the associated COVID-19 disease, and their variants.

Other objects and advantages of various aspects of the invention will be apparent to those of skill in the art upon review of the teachings herein. The various aspects of the invention, set forth explicitly herein or otherwise ascertained from the teachings herein, may address any one of the above objects alone or in combination, or alternatively may address some other object of the invention ascertained from the teachings herein. It is not intended that any specific aspect of the invention (that is explicitly set forth below or that is ascertained from the teachings herein) necessarily address any of the objects set forth above let alone address all of these objects simultaneously, but some aspects may address one or more of these objects or even all of these objects simultaneously.

In a first aspect of the invention, a method for identifying presence of a selected biohazard signature in a complex sample, includes: (a) providing excitation radiation onto a portion of a sample, wherein the excitation radiation is provided as a beam from a source within a housing, wherein the beam has a dimension that is substantially smaller than a sample dimension; (b) providing the emission radiation along at least one detection path within the housing (which may involve receiving emission radiation, from the portion of the sample that received excitation radiation, onto at least one optical element which directs the emission radiation along the at least one detection path within the housing); (c) directing excitation radiation to be incident upon different portions of a sample by relatively moving the beam and the sample; (d) for each of a plurality of different portions of the sample, detecting a group of emission signals, with each group including signals from a plurality of different wavelength bands, using at least one detector located within the housing at a location along the at least one detection path; (e) for the plurality of groups of emission signals associated with the plurality of different sample portions, distinguishing useful (or usable) signal groups from unusable signal groups, where useful signal groups are those containing at least one signal having a strength that is greater than a strength of a corresponding background signal by a predefined amount; (f) directly or indirectly providing both predetermined biohazard indicative signal information and predetermined non-biohazard indicative signal information related to the selected biohazard signature; (g) producing a biohazard indicative status (e.g., classification) for each useful signal group based at least in part upon a comparison of emission signal data for that group, directly or indirectly, with the predetermined biohazard indicative signal information and predetermined non-biohazard indicative signal information; and (h) forming a biohazard indicative conclusion based, at least in part, on a combination of (1) biohazard indicative statuses for a plurality of useful signal groups and (2) relative spacings between the portions of the sample associated with the plurality of useful signal groups.

In a second aspect of the invention, a method for determining the presence of a material of interest within a sample, includes: (1) providing excitation radiation from a source within a housing onto a sample; (2) receiving emission radiation, from the sample location arising from the excitation radiation, onto at least one optical element which directs the emission radiation along at least one detection path within the housing; (3) detecting emission radiation using at least one detector located within the housing at a location along the at least one detection path; and (4) determining whether or not the material of interest was present in the sample, wherein the method is characterized by: (a) the method of determining being a method for identifying presence of a selected biohazard signature in a complex sample; (b) the providing of excitation radiation being in the form of a beam of excitation radiation having a beam dimension that is at least an order of magnitude smaller than a sample dimension; (c) directing excitation radiation to be incident upon different portions of a sample by relatively moving the sample and the beam such that the excitation radiation successively impacts a plurality of different portions of the sample and such that a plurality of groups of emission signals are detected, with each group including signals from a plurality of different wavelength bands associated with a specific sample portion; and (d) wherein the determining, includes: (i) distinguishing useful signal groups from unusable signal groups, where useful signal groups are those containing at least one signal having a strength that is greater than a strength of a corresponding background signal by a predefined amount; (ii) directly or indirectly providing both predetermined biohazard indicative signal information and predetermined non-biohazard indicative signal information related to the selected biohazard signature; (iii) producing a biohazard indicative status (e.g., classification) for each useful signal group based at least in part upon a comparison of emission signal data for that group, directly or indirectly, with the predetermined biohazard indicative signal information and predetermined non-biohazard indicative signal information; and (iv) forming a biohazard indicative conclusion based, at least in part, on a combination of (1) biohazard indicative statuses for a plurality of useful signal groups and (2) relative spacings between sample positions associated with the plurality of useful signal groups.

Numerous variations of the first and second aspects are possible. Furthermore, numerous variations of such variations are also possible. Such variations include, for example: (1) the excitation radiation being or including radiation with wavelength below 300 nanometers; (2) the at least one optical element being located within the housing; (3) the at least one optical element being supported directly or indirectly by the housing; (4) the beam dimension being or including a beam width; (5) the sample dimension being or including a sample width; (6) the directing of excitation radiation including a method selected from the group consisting of: (a) operating a stage to move the sample relative to an exposure location of excitation radiation to provide excitation radiation to different portions of the sample, (b) operating at least one controllable scanning mirror for scanning the excitation radiation to different portions of the sample, (c) flowing the sample within a flow channel passed an exposure location such that different portions of the sample in turn receive excitation radiation based on the flow of the sample and relative positioning of the different portions of the sample within the flow channel, (d) moving an aperture that allows excitation radiation to strike a sample at a single location and emission radiation to reach a detector from the single location at any given time and moving the aperture to obtain emission data from the plurality of locations on the sample, (e) using a movable aperture that allows only emission radiation from a single location to reach a detector at any given time (i.e. the aperture defines an allowed path for emission radiation as opposed to an allowed path for excitation radiation), (f) a combination of any of at least two of (a)-(e); (7) the directing of excitation radiation including operating a stage to move the sample relative to an exposure location of excitation radiation to provide excitation radiation to different portions of the sample; (8) the directing of excitation radiation including operating at least one controllable scanning mirror for scanning the excitation radiation to different portions of the sample; (9) variation 8 wherein the at least one scanning mirror is selected from the group consisting of: (a) a galvanometer scanner, (b) a stepper motor scanning system, (c) a rotational scanning mirror system, (d) a tip/tilt scanning mirror system, (e) an oscillating mirror system, (f) a flying spot scanner, (g) a polygonal scanning mirror system, (h) a raster scanning system, (i) a dither mirror scanning system, (j) an oscillating mirror scanning system, and (k) a scanning system capable of two dimensional scanning; (10) the directing of excitation radiation including flowing the sample within a flow channel passed an exposure location such that different portions of the sample in turn receive excitation radiation based on the flow of the sample and relative positioning of the different portions of the sample within the flow channel; and (11) variation 10 with the sample dimension being a sample length within the flow channel. Some of the above variations may be combined with one another, mutatis mutandis, in a single method to the extent such combination does not completely remove all functionality provided by each of the combined elements or is not otherwise prohibited.

Numerous additional variations of the first and second aspects and of previous variations are possible where such additional variations focus on the type of biohazard that is subject to identification. Such additional variations, for example, include: (12) the selected biohazard posing a threat to a non-human living organism; (13) the selected biohazard posing a threat to a human; and (14) the biohazard including a pathogen and the biohazard signature being a pathogen signature.

Numerous additional variations of the first and second aspects and of previous variations are possible where such additional variations are focused on features set forth in the preamble of the first aspect but apply equally to any corresponding features of the second aspect as well as to variations of both. Such additional variations, for example, include: (15) the selected biohazard signature being selected from the group consisting of: (a) a molecular indicator of a biohazard, (b) a molecular indicator of a non-infecting presence of a biohazard, (c) a molecular indicator of an infecting presence of a biohazard, (d) a molecular indicator of a past infecting presence of a biohazard (e.g., an immunoassay) wherein the biohazard is selected from the group consisting of: (i) a virus, (ii) a fungus, (iii) a yeast, (iv) a mold, (v) a bacterium, (vi) a prion, and (vii) a biological toxin, e.g., ricin; (16) the selected biohazard being selected from the group consisting of: (a) a coronavirus, (b) a SARS-CoV-2 virus or variation thereof, that may cause coronavirus disease 2019, i.e. COVID-19, or a variation thereof, (c) an influenza virus (e.g. A, B, C, or D), (d) a hemorrhagic virus, e.g. an ebolavirus, a hantavirus, the Marburg, or the like; (17) the complex sample being a material selected from the group consisting of: (a) a nasal fluid, (b) saliva, (c) sputum, (d) rectal fluids, (e) rectal solids; (f) material from the surface of the skin, (g) skin tissue, (h) material from a wound site, (i) material from a fingernail or toenail, (j) material from an ear canal, (k) a fluid from or around an eye, (l) blood, (m) blood serum, (n) blood plasma, (o) respiratory tract material or fluid, (p) glandular exocrine secretions, and (q) secretions from an exposed portion of a patient's body, e.g., from the fingerprints or from palm prints; and (18) the complex sample including a material selected from the group consisting of: (a) air, (b) water, (c) material in the air that has been condensed from the air and then placed on a sample location, (d) material in the air that has been condensed directly on a sample location by lowering the temperature of the air, (e) material in the air that has been condensed onto a sample location by lowering the temperature of the air and by blowing or drawing the air past the sample location, (f) material transferred to a surface by touching, (g) material transferred to a surface by sneezing, (h) material transferred to a surface by coughing, (i) material found on the inside of a mask or face shield prior to usage, (j) material found on the inside of a mask or face shield after usage, (k) material found on the outside of a mask or face shield after usage, and (l) material extracted from an outer surface of a glove after usage.

Numerous additional variations of the first and second aspects and of previous variations are possible where such additional variations are focused on features set forth in element (a) of the first aspect but apply equally to any corresponding features of the second aspect as well as to variations of both. Such additional variations, for example, include: (19) the excitation radiation including radiation selected from the group consisting of: (a) ultraviolet radiation with a wavelength less than 275 nm, and (b) ultraviolet radiation with a wavelength less than 250 nm; (20) the excitation radiation being supplied in a form selected from the group consisting of: (a) CW radiation, (b) radiation supplied in pulses with durations greater than 100 ns (nanosecond), (c) radiation supplied in pulses with durations greater than 1 µs (microsecond), (d) radiation supplied in pulses with durations greater than 10 µs, (e) radiation supplied with a power density smaller than that which will cause adiabatic heating damage to the biohazard signature; and (f) radiation supplied at a power level, over a time, and with a number of repetitions (i.e. exposures) that will not substantially inhibit detection of the biohazard signature after N such exposures where N may be set to a number as small as two or greater than ten or more, wherein not substantially inhibiting detection is selected from the group consisting of (i) not reducing detection by more than 10%, (ii) not reducing detection by more than 20%, (iii) not reducing detection by more than 50%, (iv) not increasing presence of false negative conclusions by more than 1%, (v) not increasing presence of false negative conclusions by more than 2%, (vi) not increasing presence of false negative conclusions by more 5%, (vii) not increasing presence of false negative conclusions by more than 10%, (viii) not increasing presence of false negative conclusions by more than 25%; (21) the source of the UV excitation radiation being selected from the group consisting of: (a) any radiation source with a wavelength less than 250 nm, (b) an LED source with a wavelength less than 300 nm, (c) an LED source with a wavelength less than 275 nm, (d) an LED source with a wavelength less than 250 nm, (e) an LD (laser diode) with a wavelength less than 300 nm, (f) an LD source with a wavelength less than 275 nm, (g) an LD source with a wavelength less than 250 nm, (h) a CW laser source with a wavelength less than 300 nm, (i) a CW laser source with a wavelength less than 275 nm, (j) a CW laser source with a wavelength less than 250 nm, (k) a pulsed laser source with a wavelength less than 300 nm, (l) a pulsed laser source with a wavelength less than 275 nm, (m) a pulsed laser source with a wavelength less than 250 nm, (n) unpolarized ultraviolet source with a wavelength below 300 nm, (o) any of variations 20a-20n wherein no more than 10% of the excitation radiation is above the indicated wavelength, and (p) any of variations 20a-20o wherein no more than 20% of the excitation radiation is above the indicated wavelength; (22) the beam dimension being a width and having a size selected from the group consisting of: (a) less than 1 mm, (b) less than 0.5 mm, (c) less than 0.2 mm, (d) less than 0.1 mm, (e) less than 0.05 mm, (f) at least 10 times less than a corresponding width of the sample location, (g) at least 50 times less than a corresponding width of the sample location, (h) at least 100 times less than a corresponding width of the sample location; (23) the beam having a maximum width to minimum width ratio at or near a focal point selected from the group consisting of: (a) less than 5.0, (b) less than 2.0, (c) less than 1.5, (d) less than 1.25, and (e) less than 1.1; (24) the sample location being selected from the group consisting of: (a) a surface of material that is otherwise sterile but for the presence of the complex sample, (b) a metal surface that is otherwise sterile but for the presence of the complex sample, (c) a stainless-steel surface that is otherwise sterile but for the presence of the complex sample, (d) an otherwise sterile swab which has swabbed a surface for which the presence of the biohazard signature is to be determined, (e) a non-sterile surface for which the presence of the biohazard signature is to be determined, (f) an inside surface of a face mask or face shield that was worn by a subject for which the presence of the biohazard signature is to be determined, (g) an outside surface of a face mask or face shield that was worn by a subject for which the presence of the biohazard signature is to be determined, (h) a surface which has been cleaned for which the absence of the biohazard signature is to be confirmed, (i) a skin surface of a subject to be tested, (j) a surface within a wound on a subject to be tested, (k) a surface within a lesion, (l) a print region of a finger or toe; and (m) a palm of a hand.

Numerous additional variations of the first and second aspects and of previous variations are possible where such additional variations are focused on features set forth in element (b) of the first aspect but apply equally to any corresponding features of the second aspect as well as to variations of both. Such additional variations, for example, include: (25) the emission radiation that is being detected includes radiation selected from the group consisting of: (a) native fluorescence radiation, (b) Raman radiation, (c) phosphorescence, (d) fluorescence decay over time after excitation radiation exposure ceases, (e) native fluorescence radiation for a plurality of sample positions with a first spacing followed by further fluorescence radiation exposure at one or more intermediate positions to at least one selected pair of positions of the set of the plurality of positions where initial fluorescence radiation for the selected set of the plurality of positions provided a result that triggered the further radiation exposure at the one or more intermediate positions, and (f) native fluorescence radiation for a plurality of sample positions followed by Raman radiation at at least one position selected from the group consisting of: (a) at least one of the plurality of positions, and (2) at least one position intermediate to the plurality of sample positions where initial fluorescence radiation for at least one of the plurality of sample positions provided a result that triggered a more detailed analysis of the at least one position using the Raman radiation; (26) the emission radiation including native fluorescence radiation wherein the plurality of different wavelength bands for each group of emission signals includes at least N wavelength bands wherein N is selected from the group consisting of: (a) at least four, (b) at least eight, (c) at least fifteen, (d) at least thirty, (e) at least sixty, (f) at least one-hundred twenty, (g) at least two hundred fifty, (h) at least five hundred, (i) at least one thousand, and (j) at least two thousand; (27) the emission radiation including Raman radiation, wherein the plurality of different wavelength bands for each group of emission signals includes at least M wavelength bands wherein M is selected from the group consisting of: (a) at least four, (b) at least eight, (c) at least fifteen, (d) at least thirty, (e) at least sixty, (f) at least one-hundred twenty, (g) at least two hundred fifty, (h) at least five hundred, (i) at least one thousand, and (j) at least two thousand; (28) the at least one detection path including a single detection path; (29) variation 28 with the single detection path including at least one optical element that can be used to change wavelengths that reach a detector selected from the group consisting of: (a) at least one low pass filter, (b) at least one high pass filter, (c) at least one band pass filter, (d) at least one dichroic filter, (e) at least one tunable filter, (f) at least one acousto-optic tunable filter, (g) at least one diffraction grating, (h) at least one prism, (i) at least one diffractive element, and (j) at least one dispersive element; (30) the at least one detection path including a plurality of different detection paths, selected from the group consisting of: (a) a single path that is divided into multiple paths, (b) a single path that is divided into multiple paths by at least one dispersive element, (c) a single path that is divided into multiple paths by at least one non-dispersive element, (d) a single path that is divided by a series of non-dispersive elements to obtain a series of paths having different wavelengths, (e) a single path that is divided into multiple paths by at least one non-dispersive element wherein at least one of the multiple paths is divided into a plurality of additional paths by at least one dispersive element, (f) a single path that is divided into multiple paths by at least one non-dispersive element wherein a plurality of the multiple paths are each divided into a plurality of additional paths using a plurality of dispersive elements, (g) multiple paths for which at least one is divided into multiple additional paths, and (h) multiple paths for which a plurality is divided into multiple additional paths; (31) the detected emission radiation including wavelengths selected from the group consisting of: (a) greater than 250 nm, (b) greater than 275 nm, (c) greater than 300 nm, (d) less than 600 nm, (e) less than 500 nm, (f) less than 400 nm, (g) less than 380 nm, (h) within the range of 250 to 600 nm, (i) within the range of 270 to 600 nm, (j) within the range of 280 to 600 nm, (k) within the range of 280 to 550 nm, and (l) within the range of 300 to 500 nm; (32) the emission radiation being detected with a timing selected from the group consisting of: (a) during exposure but greater than 1 μs (microsecond) after the initiation of excitation radiation, (b) during exposure but greater than 5 μs after initiation of the excitation radiation, (c) during exposure but greater than 10 μs after initiation of the excitation radiation, (d) during exposure but greater than 20 μs after initiation of the excitation radiation, (e) greater than 1 μs (microsecond) after the extinction of excitation radiation, (f) greater than 5 μs after the extinction of excitation radiation, (g) greater than 10 μs after the extinction of excitation radiation, (h) greater than 20 μs after the extinction of excitation radiation, (i) at a set time after initiation of the excitation radiation, (j) at a plurality of different set times after initiation of the excitation radiation, (k) at a set time after extinction of the excitation radiation, (l) at a plurality of set times after extinction of the excitation radiation, and (m) a combination of the times set forth in a plurality of (a)-(l) of variation 32; (33) the at least one optical element including at least one element selected from the group consisting of: (a) at least one planar mirror, (b) at least one focusing mirror, (c) at least one lens, (c) at least one diffraction grating, (e) at least one prism, (f) at least one low pass filter, (g) at least one band pass filter, (h) at least one high pass filter, (i) at least one dichroic filter, (j) at least one modulator (e.g., an acousto-optic modulator), (k) at least one beam splitter, (l) at least one aperture, (m) at least one iris diaphragm, (n) at least one polarizer, (o) at least one fiber optic, (p) at least one UV opaque window, (q) at least one UV transmitting window, (r) at least one detector, (s) at least one diffractive element, and (t) at least one dispersive element.

Numerous additional variations of the first and second aspects, and of previous variations, are possible where such additional variations are focused on features set forth in element (c) of the first aspect but apply equally to any corresponding features of the second aspect as well as to variations of both. Such additional variations, for example, include: (34) variation 7, or any of variations 8-33 as they depend from variation 7, wherein movement provided by the stage is selected from the group consisting of: (a) relative movement of the beam of excitation radiation from one sample position to another sample position; (b) relative movement of the beam on a sample location to provide improved focusing of the beam of excitation radiation on the sample position; (c) relative movement of the sample position substantially perpendicular to an optical axis selected from the group consisting of: (i) an incident optical axis of the beam of excitation radiation, (ii) an emission optical axis extending from an exposed portion of the sample to a first of the at least one optical element, and (iii) an intermediate optical axis that is between the incident and emission optical axes; (d) relative movement of the sample position substantially parallel to an optical axis selected from the group consisting of: (i) an incident optical axis, (ii) an emission optical axis, and (iii) an intermediate optical axis; (e) relative movement of the sample position to allow focusing of emission energy onto a selected optical element; (f) the relative movement of any of 34(a)-34(e) wherein the sample position is moved; (g) the relative movement of any of 34(a)-34(e) wherein at least an excitation axis and an emission axis are moved, and (h) a combination of selected elements of 34(a)-34(g) wherein substantially means within an angular amount selected from the group consisting of: (i) within 10 degrees, (ii) within 5 degrees, (iii) within 2 degrees, and (iv) within 1 degree; (35) variation 34 wherein the stage provides independent X and Y axis movement in a plane substantially perpendicular to an optical axis, wherein the optical axis is selected from the group consisting of: (a) an incident optical axis, (b) an emission optical axis, (c) an intermediate optical axis, and (d) an axis perpendicular to a plane of the sample; (36) variation 34 wherein the stage provides rotary movement in a plane substantially perpendicular to an optical axis, wherein the optical axis is selected from the group consisting of: (a) an incident optical axis, (b) an emission optical axis, (c) an intermediate optical axis, and (d) an axis perpendicular to a plane of the sample; (37) variation 7, or any of variations 8-33 as they depend from variation 7 wherein the stage includes motion control selected from the group consisting of: (a) a stage capable of independent X movement, (b) a stage capable of independent Y movement, (c) a stage capable of independent Z movement, (d) a stage capable of rotary movement in an XY plane, (e) a hexapod stage, and (f) a stage providing motion control selected from a plurality of (a)-(e) of variation 37.

Numerous additional variations of the first and second aspects and of previous variations are possible where such additional variations are focused on features set forth in element (d) of the first aspect but apply equally to any corresponding features of the second aspect as well as to variations of both. Such additional variations, for example, include: (38) the at least one detector including a detector selected from the group consisting of: (a) a CCD array, (b) a plurality of CCD arrays located along at least partially different detection paths, (c) a cooled CCD array, (d) a plurality of cooled CCD arrays located along at least partially different detection paths, (e) a PN or PIN photodiode or photodiode array, (f) an avalanche photodiode or photodiode array, (g) a plurality of photodiodes located along at least partially different detection paths, (h) a photomultiplier tube (PMT), (i) a PMT array, and (j) a combination of any of (a)-(i) of variation (38).

Numerous additional variations of the first and second aspects and of previous variations are possible where such additional variations are focused on features set forth in element (e) of the first aspect but apply equally to any corresponding features of the second aspect as well as to variations of both. Such additional variations, for example, include: (39) the predefined amount is a ratio of measured signal strength to background signal selected from the group consisting of: (a) at least three; (b) at least five; (c) at least seven; (d) at least ten; and (e) at least fifteen. In some variations the ratio may, for example be defined as $MV_i/Noise_i > X$ or $(MV_i-Noise_i)/Noise_i > X$, wherein $MV_i$ is a measured emission value for wavelength band i, $Noise_i$ is a noise level value associated with wavelength band i, and X is a threshold value greater than 1 (such as a value between 2 and 15). In some variations data that is used in further processing may be or may not have background noise removed, e.g., by defining $UD_i = RD_i - Noise_i$, or $UD_i = RD_i$, where UDi=Usable Data for band i, and RDi=Raw Data for band i. In some variations prior to comparing usable spectrum data for each wavelength band to spectrum data from samples with positive or negative biohazard signatures it may be appropriate to normalize the data. Such normalization might, for example, define a normalization factor as a value that converts the band with the highest peak reading to a defined value (e.g. 100), and thereafter the readings for all bands are multiplied the same factor. For example, Target Value/$MV_P$=Normalization Factor, or where Target Value/$(MV_P-Noise_P)$=Normalization Factor, and where $MV_p$ is a measured emission value for the wavelength band having the highest peak value, and where $Noise_p$ is a noise level value associated with the wavelength band having the highest peak.

Numerous additional variations of the first and second aspects and of previous variations are possible where such additional variations are focused on features set forth in element (f) of the first aspect but apply equally to any corresponding features of the second aspect as well as to variations of both. Such additional variations, for example, include: (40) the predetermined biohazard indicative signal information and non-biohazard indicative signal information is provided on a band-by-band basis or band-by-band ratio basis for a plurality of samples known to contain the biohazard containing samples and for a plurality of samples known not to contain the biohazard wherein the information is provided in a form selected from the group consisting of: (a) raw band-by-band data for the each of the plurality of samples known to contain and known not to contain the biohazard, (b) normalized band-by-band data for the each of the plurality of samples known to contain and known not to contain the biohazard, (c) a plurality of selected band-to-band ratios for each of the plurality of samples known to contain and known not to contain the biohazard, (d) a band-by-band value taken from normalized data for each group of samples known to contain and known not to contain the biohazard, wherein the value is selected from the group consisting of: 1) a mean, 2) a mode, 3) a median, 4) a midpoint of a range, 5) a midpoint of a range with outliers removed, 6) a low range number with or without outliers removed, and 7) a high range number with or without outliers removed, (e) the band-by-band value of (d) along with at least one value indicative of range, wherein the at least one value indicative of range is selected from the group consisting of: 1) a standard deviation, 2) a plus range number, 3) a minus range number, 4) both a plus and minus range number, 5) a full range number with or without outliers removed, and 6) S standard deviations where S is a number between 1 and 10, (f) a band-by-band low range and high range value taken from normalized data with or without outliers removed, (g) a band-by-band group of equations or group of relationships bridging the normalized emission values for the predetermined known biohazard containing and non-biohazard containing groups, (h) a band-by-band set of normalized detection values for each of the groups of predetermined samples known to contain biohazard signatures and known not to contain biohazard signatures wherein the band-by-band set of normalized detection values are closer to the detection values for their respect group than they are to the values for the other group, (i) a plurality of values for selected band-to-band ratios for each of the predetermined known biohazard and non-biohazard containing groups wherein each of the values is selected from the group consisting of: 1) a mean, 2) a mode, 3) a median, 4) a mid-point of a range, 5) a midpoint of a range with outliers removed, 6) a low range number with or without outliers removed, 7) or a high range number with or without outliers removed, (j) the plurality of values of (i) along with at least one value indicative of ratio range, wherein the at least one value indicative of ratio range is selected from the group consisting of: 1) a standard deviation, 2) a plus range number, 3) a minus range number, 4) both a plus and minus ratio range number, 5) a full range number with or without outliers removed, and 6) S standard deviations where S is a number between 1 and 10, (k) a plurality of selected band-to-band ratios providing a low range value and a high range value taken with or without outliers removed, (l) a plurality of selected band-to-band ratio equations or relationships bridging the emission value ratios for the predetermined known biohazard containing and non-biohazard containing groups, (m) a selected band-to-band set of ratio values for each of the groups of predetermined samples known to contain biohazard signatures and known not to contain biohazard signatures wherein the band-by-band set of ratio values are closer to the ratio values for corresponding ratio values for their respective group than they are to the values for the other group, (n) central values (e.g., averages, means, or medians) and range related values (e.g., lower range limit and upper range limit with or without removal of outliers, a standard deviation, or a multiple of a standard deviation) for each band as obtained from the plurality of samples known to contain biohazard signatures and those known not to contain biohazard signatures, and (o) central values (e.g., averages, means, or medians) and range related values (e.g., lower range limit and upper range limit with or without removal of outliers, a standard deviation, or a multiple of a standard deviation) for each of a plurality of selected band-to-band ratios as obtained from the plurality samples known to contain the biohazard signatures and those known not to contain the biohazard signatures. In different variations predetermined biohazard indicative and non-biohazard indicative signal information may take different forms including, for example: raw spectrum data, data with background noise removed, normalized data, condensed spectrum data that has been processed using programmer defined algorithms, trained AI or ML algorithms, information that is the same for multiple systems or that is recreated and/or customized for different systems, information that is periodically reevaluated for a given instrument to verify, revalidate, or update operational algorithms. In some variations samples of known status may be run or rerun for the system periodically to re-establish, or to confirm a need to reestablish algorithm training or verification of instrument performance.

Numerous additional variations of the first and second aspects and of previous variations are possible where such additional variations are focused on features set forth in element (g) of the first aspect but apply equally to any corresponding features of the second aspect as well as to variations of both. Such additional variations, for example, include: (41) producing a biohazard indicative status for each useful signal group based at least in part upon a comparison of emission signal data for that group, directly or indirectly, with the predetermined biohazard indicative signal information and predetermined non-biohazard indicative signal information where the comparison is performed on a basis selected from the group consisting of: (a) for each of at least a selected plurality of the bands, comparing the measured spectral information to those of the samples with known biohazard and non-biohazard indicative signatures and determining if the spectral information of the measured sample is generally closer to that of the samples with known biohazard signatures or known non-biohazard indicative signatures and labeling the band with a corresponding biohazard status, and then combining the corresponding biohazard status for each selected band to provide a biohazard indicative status or classification for the sample location or position; (b) using calculated ratio of spectral information associated with each selected band and at least one other band from the measured sample to a corresponding ratio of bands from the samples with known biohazard and known non-biohazard indicative signatures and determining if the ratio of the measured sample is generally closer to that of the samples having the known biohazard signature or having the known non-biohazard signature and labeling the band with a corresponding biohazard status, and then combining the corresponding biohazard status for each selected band to provide a biohazard indicative status or classification for the sample location or position; (c) using a basis selected from (a) and (b) to produce higher order comparisons, such as those that produce comparables from combinations of spectral data readings or ratios from different wavelength bands, or the like; (d) using a selected artificial intelligence (AI) or machine learning (ML) algorithm that is trained and verified with the information including the attributes of the samples with known biohazard signature statuses such that when the measured data associated with specific locations of samples undergoes analysis, the trained algorithm produces results that are consistent with training data and meets requirements associated with limiting false positives and false negatives; (e) using basis (d) with the AI or ML algorithm including an instance-based algorithm selected from the group consisting of: a K Nearest Neighbor (KNN) algorithm, a Learning Vector Quantization (LVQ) algorithm, a Self-Organizing Map (SOM) analysis, a Locally Weighted Learning (LWL) analysis, or a Support Vector Machines (SVM) analysis; (f) using basis (d) with the AI or ML algorithm including a dimensionality reduction algorithm, selected from the group consisting of: a Principal Component Analysis (PCA), a Principal Component Regression (PCR), a Partial Least Squares Regression (PLSR), or a Discriminant Analysis (DA); and (g) using basis (d) with the AI or ML algorithm including a regression analysis selected from the group consisting of: an Ordinary Least Squares Regression (OLSR) analysis, a Linear Regression analysis, a Logistic Regression analysis, a Stepwise Regression analysis, a Multivariate Adaptive Regression Splines (MARS) analysis, or a Locally Estimated Scatterplot Smoothing (LOESS) analysis; (42) variation 41 wherein the biohazard indicative status (e.g., classification) for each useful signal group is selected from the group consisting of: (a) biohazard present, (b) no biohazard present, (c) indeterminate biohazard status, and (d) a weighted biohazard indicative status (e.g., based on a consistency of the band-to-band, or band-to-band ratio, or based on indicative status for each band or each selected band-to-band ratio, of a given useful signal group); (43) variation 41 wherein each band-to-band based indicative status (e.g., classification) or selected band-to-band ratio-based indicative status (e.g., classification) is provided as a rating dependent on how the emission signal data of a given useful signal group compares to the predetermined biohazard indicative signal information and the predetermined non-biohazard indicative signal information; (44) variation 41 wherein the basis is selected from the group consisting of (a) and (b), wherein the combining includes a sum of the number of bands or the number of selected ratios that are indicative of biohazard presence minus those indicative of no biohazard presence; (45) variation 44 wherein a positive sum provides a biohazard indicative status that points toward the biohazard being present while a negative sum provides a biohazard indicative status that points toward the biohazard not being present; (46) variation 44 wherein a positive sum provides provisional biohazard indicative status that points toward the biohazard being present while a negative sum provides provisional biohazard indicative status that points toward the biohazard not being present while a magnitude of the sum divided by the number of bands, or the number of selected ratios, provides a weighting to the provisional biohazard indicative status for the given useful signal group detection signal wherein the weighting is used in providing a biohazard indicative status for the given useful signal group; (47) variation 44 wherein the combining includes a sum of the ratings and a determination of whether the sum when compared to a first threshold value is indicative of likely biohazard presence or the sum when compared to a second threshold value that is indicative of unlikely biohazard presence; (48) variation 47 wherein the first and second threshold values are the same common threshold value and a sum equal to the common threshold value is classified as either likely or unlikely such that combination produces a binary result; and (49) variation 47 wherein the first threshold value and the second threshold values are different and sums having values between the first and second threshold values are deemed inconclusive about biohazard presence. In some other variations only selected wavelength bands may be used in making comparisons or summed readings from selected groups of bands may be used in making comparisons or creating ratios.

Numerous additional variations of the first and second aspects, and of previous variations, are possible where such additional variations are focused on features set forth in element (h) of the first aspect but apply equally to any corresponding features of the second aspect as well as to variations of both. Such additional variations, for example, include: (50) the minimum number of emission signal groups required to provide a determinate biohazard indicative status being selected from the group consisting of: (a) greater than 50, (b) greater than 100, (c) greater than 200, (d) greater than 400, (e) greater than 600, and (f) greater than 800; (51) variation 50 wherein the number of useful signal groups required to provide determinate biohazard indicative status is selected from the group consisting of: (a) greater than 10% of the emission signal groups, (b) greater than 20% of the emission signal groups, (c) greater than 40% of the emission signal groups, (d) greater than 60% of the emission signal groups, and (e) greater than 80% of the emission signal groups; (52) the forming of a biohazard indicative conclusion being based on steps selected from the group consisting of: (a) selecting a given useful signal group having a biohazard indicative status of likely biohazard presence, and successively looking at next nearest neighbor useful signal groups until either a count of likely biohazard presence exceeds a value N in which case a biohazard indicative conclusion of "biohazard present" is made, or a count of no likely biohazard presence exceeds M, in which case the selecting and looking restarts with a new useful signal group having a likely biohazard presence indication after resetting sums, and the process continues until either a conclusion of biohazard presence is reached or all acceptable useful signal groups have acted as a starting point with no conclusion of biohazard presence being reached in which case a conclusion of "no biohazard presence" is reached, wherein N is selected from the group consisting of: at least 3, at least 5, at least 7, at least 9, at least 11, at least 15, at least 25, and wherein M is selected from the group consisting of: 0, at least 1, at least 10% of N, no more than 10% of N, at least 20% of N, no more than 20% of N, at least 30% of N, and no more than 30% of N; (b) selecting a given useful signal group having a biohazard indicative status of likely biohazard presence, and successively looking at next nearest neighbor signal groups until either a count of likely biohazard presence exceeds a value N in which case a biohazard indicative conclusion of "biohazard present" is made, or a count of no likely biohazard presence exceeds M, a count of unusable signal groups exceeds R, or a count of groups having indeterminate biohazard statuses exceed S, or some combined sum associated with M, R, and/or S exceeds an amount T in which case the selecting and looking restarts with a new useful signal group having a likely biohazard presence indication after resetting sums, and the process continues until either a conclusion of biohazard presence is reached or all acceptable useful signal groups have acted as a starting point with no conclusion of biohazard presence being reached in which case a conclusion of "no biohazard present" is reached, wherein N is selected from the group consisting of: at least 3, at least 5, at least 7, at least 9, at least 11, at least 15, at least 25, and wherein M is selected from the group consisting of: 0, at least 1, at least 10% of N, at least 20% of N, and at least 30% of N, wherein R is selected from the group consisting of 0, at least 1, at least 10% of N, no more than 10% of N, at least 20% of N, no more than 20% of N, at least 30% of N, and no more than 30% of N, where S is selected from the group consisting of 0, at least 1, at least 10% of N, no more than at least 20% of N, at least 30% of N, and no more than 30% of N, wherein T is selected from the group consisting of 0, at least 1, at least 10% of N, no more than 10% of N, at least 20% of N, no more than 20% of N, at least 30% of N, and no more than 30% of N; and (c) selecting a given useful signal group having a biohazard indicative status of likely biohazard presence, and successively looking at next nearest neighbor signal groups until either a count of likely biohazard presence exceeds a value N (e.g. at least 3, 5, 7, 9, 11, 13 or more) in which case a biohazard indicative conclusion of "biohazard present" is made, or a count of no likely biohazard presence exceeds M (e.g. at least 0, 1, 2, 3, or more, or an amount that is a percentage of N, e.g. something between 2%-50%), a count of unusable signal groups exceeds R (e.g. at least 0, 1, 2, 3, or more, or an amount that is a percentage of N, e.g. something between 2%-50%), or a count of groups having indeterminate biohazard statuses exceed S (e.g. at least 0, 1, 2, 3, or more, or an amount that is a percentage of N, e.g. something between 2%-50%), or some combined sum associated with M, R, and/or S exceeds an amount T (e.g. at least 0, 1, 2, 3, or more or an amount that is a percentage of N, e.g. something between 2%-50%), wherein the count of one or more of M, R, or S is reset to 0 when a count of successive nearest neighbors have likely biohazard presence status exceeds T (e.g. where T is at least 2, 3, 4, or more or is some fraction of N), wherein if S is exceeded, the selecting and looking restarts with a new useful signal group, and reset sums, having a likely biohazard presence indication after resetting sums, and the process continues until either a conclusion of biohazard presence is reached or all acceptable useful signal groups have acted as a starting point with no conclusion of biohazard presence being reached in which case a conclusion of "no biohazard present" is reached; and (53) the biohazard indicative conclusion indicating the presence of the biohazard requires the presence of a condition selected from the group consisting of: (a) a plurality of neighboring biohazard indicative statuses each providing an indication of the likely presence (e.g., classification is positive) of the biohazard, wherein a number of the plurality is selected from the group consisting of: (i) at least three, (ii) at least five, (iii) at least seven, (iv) at least ten, and (vi) at least fifteen, (b) at least N % of a plurality of nearest neighbor biohazard indicative statuses, provide an indication of the likely presence of the biohazard (e.g., classification is positive), wherein a number of the plurality is selected from the group consisting of: (i) at least five, (ii) at least seven, (iii) at least ten, and (iv) at least fifteen, and wherein N is selected from the group consisting of: (i) greater than 50%, (ii) greater than 65%, (iii) greater than 80%, and (iv) greater than 90%, (c) a plurality of nearest neighbor biohazard indicative statuses each providing an indication of the likely presence of the biohazard (e.g., classification is positive), with a possible exception of one that may provide an indeterminate presence (e.g. classification is neither positive or negative) of the biohazard or an indication of no likely presence of the biohazard (e.g. classification is negative), wherein a number of the plurality is selected from the group consisting of: (i) at least five, (ii) at least seven, (iii) at least ten, and (iv) at least fifteen, (d) a plurality of neighboring biohazard indicative statuses (e.g. K nearest neighbor where K is a whole number greater than 1) each providing an indication of the likely presence of the biohazard (e.g. classification is positive), with a possible exception of the larger of 10% or one that may provide an indication of no likely presence of the biohazard (e.g. classification is negative), and the larger of 20% or one that may provide an indeterminant indication of the presence of the biohazard (e.g. classification is neither positive or negative), wherein a number of the plurality is selected from the group consisting of: (i) at least five, (ii) at least seven, (iii) at least ten, and (iv) at least fifteen, (e) M clusters of N biohazard likely indicative neighboring statuses from substantially non-overlapping sample positions (wherein substantially non-overlapping sample positions has a meaning selected from the group consisting of: (i) no detected emission radiation from one sample location is included in the detected emission radiation associated with a neighboring sample location, (ii) less than 1% of detected emission radiation that is detected from one location is common to detected emission radiation coming from one or more neighboring sample locations, (iii) less than 2% of detected emission radiation that is detected from one location is common to detected emission radiation coming from one or more neighboring sample locations, (iv) less than 5% of detected emission radiation that is detected from one location is common to detected emission radiation coming from one or more neighboring sample locations, (v) less than 10% of detected emission radiation that is detected from one location is common to detected emission radiation coming from one or more neighboring sample locations, (vi) less than 20% of detected emission radiation that is detected from one location is common to detected emission radiation coming from one or more neighboring sample locations), and wherein M is at least two and N is at least 3, and the sum of M and N is at least 10, (f) at least M biohazard indicative statuses associated with a plurality of N different portions of the sample that are proximate to one another wherein the portions are physically separated by at least R exposure widths and no more than S exposure widths, wherein M is selected from the group consisting of: (i) at least three, (ii) at least five, (iii) at least nine, (iv) at least fifteen, wherein N is selected from the group consisting of: (i) at least 50, (ii) at least 100, (iii) at least 200, (iv) at least 400, and (v) at least 800, wherein R is selected from the group consisting of: (i) no less than ¼, (ii) no less than ½, (iii) no less than ¾, (iv) no less than 1, and wherein S is selected from the group consisting of: (i) no more than 2, (ii) no more than 5, (iii) no more than 10, and (iv) no more than 20, (g) a supermajority of N non-overlapping biohazard present indicative statuses provide an indicative status (or classification) of likely positive presence, wherein the supermajority is selected from the group consisting of: (1) at least ⅔ of N, (2) at least ¾ of N, (3) at least ⅘ of N, (4) at least ⅚ of N, (5) at least 6/7 of N, (6) at least ⅞ of N, (7) at least ⅞ of N, and (8) at least 9/10 of N, and wherein N is selected from the group consisting of: (1) at least 5, (2) at least 7, (3) at least 11, (4) at least 15, and at least 25, and (h) a plurality (F out of FF) of neighboring biohazard present indicative statuses from useful signal groups based on fluorescence emission detections and a plurality (R out of RR) of neighboring biohazard present indicative statuses, from useful signal groups based on Raman emission detections that are from common locations with the F out of FF statuses, wherein (i) F/R is selected from the group consisting of: 1) at least 3/at least 2, 2) at least 5/at least 3, 3) at least 9/at least 7, 4) at least 15/at least 11, and (ii) FF and RR are selected from the group consisting of: 1) at least 20, 2) at least 50, 3) at least 100, 4) at least 200, 5) at least 400, and 6) at least 800. In some variations locations having unusable data may be used in the process of determining whether an unknown sample will be considered to have a positive biohazard signature status, for example, in some such variations such unusable data locations may be treated the same as locations with negative classifications while in others they may treated as locations with a fraction of a negative classification particularly when such variations include summing counts of such negative classification locations.

Numerous additional variations of the first and second aspects, and of previous variations, are possible where such additional variations are focused on features related to the collection of samples. Such additional variations, for example, include: (54) collection of sample material selected from the group consisting of: (a) scraping a region to collect sample material to be tested, and (b) swabbing a region to collect sample material to be tested on a swab; (55) variation 54 wherein swabbing is performed to collect a sample on a swab and wherein the swab is positioned so that different sample portions are located to receive excitation radiation during the exposing of the sample to excitation radiation; (56) variation 54 wherein swabbing is performed using a swab and wherein the swab is wiped against a substrate surface to transfer at least a portion of the material collected from the swabbing over at least a portion of the surface and thereafter locating the substrate surface so that different sample portions may receive excitation radiation; (57) variation 54 wherein swabbing is performed using a swab and wherein the swab is wiped against a substrate surface to transfer at least a portion of the material collected from the swabbing over at least a portion of the surface while the substrate surface is located at an exposure location; and (58) variation 54 wherein collected material is at least in part transferred to a transport media, that is located to receive excitation radiation in turn so that different portions of the sample may be exposed and emission radiation generated and detected.

Numerous additional variations of the first and second aspects, and of previous variations, are possible where such additional variations are focused on a source of the samples. Such variations, for example, include: (59) a region of sample collection including a region selected from the group consisting of: (a) a sinus passage of a subject that is being evaluated for the biohazard signature, (b) a mouth of a subject that is being evaluated for the biohazard signature, (c) a throat of a subject that is being evaluated for the biohazard signature, (d) a wound on a subject that is being evaluated for the biohazard signature, (e) a region of skin of a subject that is being evaluated for the biohazard signature, (f) an ear canal of a subject that is being evaluated for the biohazard signature, (g) an eye of a subject that is being evaluated for the biohazard signature, (h) a fingernail or toenail of a subject that is being evaluated for the biohazard signature, (i) blood from a subject that is being evaluated for the biohazard signature, (j) blood from a surface of an area being evaluated for the biohazard signature, (k) a sample of a blood extract (e.g. plasma or serum) from a subject being evaluated for the biohazard signature, (l) a fluid sample from the respiratory tract of a subject being evaluated for the biohazard signature, (m) a tissue sample from the respiratory tract of a subject being evaluated for the biohazard signature, (n) surface of the skin of a subject being evaluated for the biohazard signature, (o) a lesion on a subject being evaluated for the biohazard signature, (p) a sample of glandular exocrine secretions from a subject being evaluated for the biohazard signature, (q) a sample of secretions from an exposed portion of a subject's body, e.g. from the finger prints or from palm prints, and (r) a surface, a fluid, or a gas in a region being examined for the biohazard signature; and (60) excitation radiation is directed onto different sample portions that are on or within a body of a subject for which a biohazard signature is being sought.

Numerous additional variations of the first and second aspects, and of previous variations, are possible where such variations are focused on additional components held by the housing Such variations, for example, include: (61) the sample being located within the housing, (62) the housing additionally holding, directly or indirectly, a programmed processor for controlling the excitation radiation source, the relative moving of the beam of excitation radiation and the sample, and the at least one detector; and a memory for storing emission radiation detection signals and associated positioning information; (63) the housing additionally holding at least one programmed processor and at least one memory for providing at least a plurality of functions selected from the group consisting of: (a) controlling the excitation radiation source, (b) controlling the relative movement of the beam of excitation radiation and the sample, (c) controlling the at least one detector, (d) storing predetermined biohazard indicative signal information, (e) storing predetermined non-biohazard indicative signal information, (f) storing background signal information, (g) storing emission detection signals and associated positioning information, (h) processing information to produce useful detection signal information, (i) processing information to produce a plurality of biohazard indicative statuses, and (j) processing information to produce a biohazard indicative conclusion; and (64) the housing further holding, directly or indirectly, one or more mechanisms selected from the group consisting of: (a) a mechanism for disposing of a sample substrate after analyzing the sample, (b) a cleaning system for dispensing a cleaning solution (e.g. via spraying, jetting, or wiping) onto a surface to be cleaned, and for removing the cleaning solution (e.g. via rinsing, blowing, heating, or wiping), (c) a sterilization system for removing or deactivating biohazards (e.g. via UV exposure, ozone exposure, spraying a sanitizer, autoclaving), and (d) a mechanism for receiving, holding, and releasing a sealed sample.

Numerous additional variations of the first and second aspects, and of previous variations, are possible where such additional variations are focused on the providing a biohazard indicative result. Such additional variations, for example, include: (65) providing a biohazard indicative result based at least in part on the biohazard indicative conclusion; (66) variation 65 wherein the biohazard indicative result is selected from the group consisting of: (a) the result being the same as the biohazard indicative conclusion, (b) the result being less nuanced than the biohazard indicative conclusion, (c) the result being either an indication of biohazard presence or non-biohazard presence, (d) the result being an indication of biohazard presence, non-biohazard presence, or indeterminate biohazard presence, and (e) the result being an indication of biohazard presence, non-biohazard presence, possible biohazard presence, or indeterminate biohazard presence; (67) a conclusion of biohazard presence having an error (e.g., as compared to conclusions provided by RT-PCR (reverse transcriptase polymerase chain reaction) or real-time RT-PCT) selected from the group consisting of: (a) less than 30%, (b) less than 20%, (c) less than 10%, (d) less than 5%, (e) less than 2%, and (f) less than 1%; and (68) a conclusion of non-biohazard presence having an error (e.g., when compared to a non-biohazard conclusion resulting from an RT-PCR or real-time RT-PCT test) selected from the group consisting of: (a) less than 30%, (b) less than 20%, (c) less than 10%, (d) less than 5%, (e) less than 2%, and (f) less than 1%.

Numerous additional variations of the first and second aspects, and of previous variations, are possible where such additional variations are focused on a method including an imaging camera and/or a display. Such additional variations, for example, include: (69) providing an imaging camera that provides an image from a sample location selected from the group consisting of: (a) an image from visible reflected radiation, (b) an image from transmitted visible radiation, (c) an image from visible radiation created by excitation, (d) an image from selected visible reflected radiation, (e) an image from selected transmitted visible radiation, (f) an image from selected visible radiation created by excitation, (g) an image from UV reflected radiation, (h) an image from transmitted UV radiation, (i) an image from UV radiation created by excitation, (j) an image from selected UV reflected radiation, (k) an image from selected transmitted UV radiation, (l) an image from selected UV radiation created by excitation, (m) an image from IR reflected radiation (e.g. when an IR source, which may or may not be an excitation source, is provided), (n) an image from transmitted IR radiation, (o) an image from IR radiation created by excitation, (p) an image from selected IR reflected radiation, (q) an image from selected transmitted IR radiation, (r) an image from selected NIR radiation created by excitation, (s) an image from NIR reflected radiation, (t) an image from transmitted NIR radiation, (u) an image from NIR radiation created by excitation, (v) an image from selected NIR reflected radiation, (w) an image from selected transmitted NIR radiation; and further includes a display for visually viewing the provided image from the sample location; (70) providing a light source for providing visible light to the sample location to aid in viewing the sample location; and (71) variation 69 including a means for visualizing an exposure location on a sample (e.g., a symbol or image displaced on a display screen, such as a crosshair position or a light spot) and setting a starting exposure location (e.g., an input option, such as a touch screen, for a program that controls exposure and detection that allows for exposure location setting). In some embodiments different types of excitation radiation may be used either for analysis or imaging purposes to see, for example, if biological material is present at the sample location.

Numerous additional variations of the first and second aspects and of previous variations are possible where such additional variations are focused on supplying power to the system. Such additional variations, for example, include: (72) the housing, directly or indirectly, additionally holding a power source for operating components held within the housing; and (73) the housing additionally holding, directly or indirectly an input port for receiving external power for operating components within the housing.

Numerous additional variations of the first and second aspects and of previous variations are possible where such additional variations are focused on outputting signals from the system or inputting signals to the system. Such additional variations, for example, include: (74) the housing, directly or indirectly, supporting an output communication device selected from the group consisting of: (a) a port for receiving a cable, (b) a proximal end of a cable, (c) a wireless transmitter, (d) a display, (e) a light source, and (f) a sound source; and wherein the communication device provides for a function selected from the group consisting of: (a) transmitting data to an external processing system for manipulating the data, and (b) providing test result conclusions; and (75) the housing, directly or indirectly, supporting a input device selected from the group consisting of: (a) a port for receiving a cable, (b) a proximal end of a cable, (c) a wireless receiver, (d) a touch screen, (e) a key pad, (f) at least one button, (g) a least one switch, and (h) a microphone for receiving audio input; and wherein the input device provides for a function selected from the group consisting of: (a) receiving operator input, (b) receiving data, (c) receiving program updates, and (d) receiving operational commands from an external device.

Numerous additional variations of the first and second aspects, and of previous variations, are possible where such additional variations are focused on physical and operational parameters of the system. Such additional variations, for example, include: (76) a volume of the housing being selected from the group consisting of: (a) less than 500 liters, (b) less than 50 liters, (c) less than 20 liters, (d) less than 10 liters, (e) less than 5 liters, and (f) less than 2 liters; (77) a mass of the housing and its contents (excluding a sample) being selected from the group consisting of: (a) less than 50 Kg, (b) less than 25 Kg, (c) less than 10 Kg, (d) less than 5 Kg, (e) less than 3 Kg, and (f) less than 2 Kg; (78) the average power consumed by components within the housing during operation being selected from the group consisting of: (a) less than 500 W, (b) less than 200 W, (c) less than 100 W, (d) less than 50 W, and (e) less than 20 W; and (79) a time period for exposing different portions of a sample a plurality of times to excitation radiation and analyzing detected emission data to reach a biohazard indicative conclusion being selected from the group consisting of: (a) less than 20 minutes, (b) less than 10 minutes, (c) less than 5 minutes, (d) less than 2 minutes, (e) less than 1 minute, and (f) less than 30 seconds.

Still numerous additional variations to the first and second aspects of the invention are possible and include, for example, other variations (e.g., combinations of variations) as set forth in the dependent method claims provided herewith, and still further variations that will be understood by those of skill in the art from the teachings set forth herein or incorporated herein by reference.

In a third aspect of the invention, a method for identifying presence of a selected biohazard signature in a sample, includes: (a) exposing a sample to excitation radiation and reading resulting emission radiation for a plurality of wavelength bands from each of a plurality of locations on the sample; (b) on a location-by-location basis, performing a first level analysis to determine which emission radiation readings meet signal threshold requirements (e.g. relative to background noise readings); (c) for each emission radiation reading meeting signal threshold requirements, performing a second level membership analysis to assign a class membership to individual location readings indicative of potential relevance to biohazard signature presence, wherein positive membership is assigned if the readings are deemed closer to readings associated with samples known to contain the biohazard signature than to readings associated with samples known not to contain the biohazard signature, and wherein negative membership is assigned to locations when readings that are deemed closer to readings associated with samples known not to contain the biohazard signature than to readings associated with samples known to contain the biohazard signature; (d) defining minimum threshold spatial grouping criteria for locations with positive membership that is necessary to conclude that the sample is positive for presence of the biohazard signature; and (e) performing at least one additional level of analysis including a determination of whether the sample includes positive membership locations that taken together in conjunction with their relative spatial positions meet the minimum positive spatial threshold grouping criteria and if so determining that the sample is positive for the presence of the biohazard signature.

A first variation of the third aspect of the invention additionally includes use of baseline spectroscopic data from a plurality of baseline samples known to contain the biohazard signature and samples known not to contain a biohazard signature in performing the second level of analysis wherein the baseline spectroscopic data is created using a method, including: (a) using one or more test methods of acceptable reliability to determine whether a biohazard signature of interest is present within each of a plurality of the baseline samples; (b) exposing each baseline sample to excitation radiation and reading resulting emission radiation for a plurality of wavelength bands from each of a plurality of locations on each of the baseline samples; and (c) separating the baseline spectroscopic data from the baseline samples into at least two groups including one group known to contain the biohazard signature and one group known not to contain the signature, wherein information from the separated groups of baseline spectroscopic data is used in performing the second level analysis, wherein the information is selected from the group consisting of: (1) the data of the group known to contain the biohazard signature, (2) the group known to not contain the biohazard signature, (3) the data from both the group known to contain the biohazard signature and the group known not to contain the biohazard signature, (4) information that has been derived from the data of the group known to contain the biohazard signature, (5) information that has been derived from the group known to not contain the biohazard signature, (6) information that has been derived from the data from both the group known to contain the biohazard signature and the group known not to contain the biohazard signature. Another variation of the third aspect involves a further variation of the first variation wherein at least two of the at least two groups are used in performing the second level analysis.

Additional variations of the third aspect are possible and include, for example, use of an additional element (e.g. operation) between the exposing and reading of the plurality of locations of step (a) of the third aspect wherein the additional element is selected from the group consisting of: (1) using a movable stage to move a sample relative to sample excitation components and emission radiation detection components when obtaining emission data from the plurality of locations on the sample, (2) using a movable stage to move one or both sample excitation radiation components and/or emission radiation detection components relative to a sample that is held in a fixed position relative to a housing between obtaining emission data from the a plurality of locations on the sample, (3) using a scanning system that changes a path taken by excitation radiation and/or emission radiation when obtaining emission data from the plurality of locations on the sample, (4) using a flow of sample material past a fixed detection location when obtaining emission data from the plurality of locations on the sample, (5) using a movable aperture that allows excitation radiation to strike a sample at a single location and emission radiation to reach a detector from a single location and moving the aperture to obtain emission data from the plurality of locations on the sample, (6) using a movable aperture that allows excitation radiation to strike a sample at a single location and thus allows only emission radiation from such location to reach a detector at any given time and moving the aperture to obtain emission data from the plurality of locations on the sample, (7) using a movable aperture that allows only emission radiation from a single location to reach a detector at any given time and moving the aperture to obtain emission data from the plurality of locations on the sample, (8) using a multiple path transmission array in controlling which location on a sample provides emission radiation for detection and moving or rotating the transmission array to allow emission radiation from the plurality of sample locations to be detected.

Further variations of the third aspect are possible and include, for example, the variations noted above for the first and second aspects mutatis mutandis.

In a fourth aspect of the invention, a system for identifying a selected biohazard signature in a complex sample, includes: (a) a source of excitation radiation located within a housing for providing a beam onto a sample wherein the beam has a dimension substantially smaller than a dimension of the sample such that the beam is incident on a portion of the sample wherein the beam has an area that is selected from the group consisting of: (i) at least an order of magnitude smaller than an area of the entire sample, (ii) at least 20 times smaller than an area of the entire sample, (iii) at least 50 times smaller than an area of the entire sample, (iv) at least two orders of magnitude smaller than an area of the entire sample, (v) at least 200 times smaller than an area of the entire sample, (vi) at least 500 times smaller than an area of the entire sample; (b) at least one optional optical element for receiving emission radiation, from the sample arising from the excitation radiation, such that emission radiation travels along at least one detection path within the housing; (c) a means for directing excitation radiation onto a plurality of different portions of the sample by relatively moving the beam and the sample; (d) at least one detector located along at least one detection path for providing a group of detected emission data in a plurality of different wavelength bands for the plurality of different portions of the sample; (e) at least one memory for holding: (i) predetermined biohazard indicative signal information and predetermined non-biohazard indicative signal information; (ii) a plurality of groups of detected emission data for the plurality of different portions of the sample, (iii) identification of useful groups of detected emission data from the plurality of different portions of the sample; (iv) biohazard indicative statuses; (v) a biohazard indicative conclusion; (f) at least one controller programmed to: (i) operate the means for directing, the source of excitation radiation, and the detector to provide groups of detected emission data from the plurality of different portions of the sample; (ii) ascertain at least one of (1) useful groups of detected emission data and (2) unusable groups of detected emission data from the plurality of groups of detected emission data, where useful groups of detected emission data are those that have at least one emission signal that is greater than a background signal by a predefined amount; (iii) compare data associated with each useful group of detected emission data with the predetermined biohazard indicative signal information and predetermined non-biohazard indicative signal information to produce a biohazard indicative status (e.g., classification) for each of the useful groups of detected emission data; and (iv) form a biohazard indicative conclusion based at least in part on a combination of biohazard indicative statuses from the plurality of useful groups of detected information and a relative separation of the different portions of the sample associated with such useful groups.

In a fifth aspect of the invention, a system for determining the presence of a material of interest in a sample, including: (1) a source located in a housing for providing excitation radiation; (2) at least one optional optical element for receiving emission radiation from the sample location arising from the excitation radiation which directs the emission radiation along at least one detection path within the housing; (3) at least one detector located within the housing for detecting emission radiation; and (4) a memory and processor for determining whether or not the material of interest was present in the sample, characterized by: (a) the system being configured to identify presence of a selected biohazard signature associated with the material of interest in a complex sample; (b) the system being configured to provide excitation radiation in the form of a beam onto a sample wherein the beam has a dimension substantially smaller than a dimension of the sample such that the beam provides an exposure location on the sample that has an area that is selected from the group consisting of: (i) at least an order of magnitude smaller than an area of entire sample, (ii) at least 20 times smaller than an area of the entire sample, (iii) at least 50 times smaller than an area of the entire sample, (iv) at least two orders of magnitude smaller than an area of the entire sample, (v) at least 200 times smaller than an area of the entire sample, (vi) at least 500 times smaller than an area of the entire sample; (c) the system additionally including a means for directing excitation radiation to be incident upon a plurality of different portions of the sample; (d) the system being configured such that the at least one detector provides a group of detected emission data in a plurality of different wavelength bands for each of the plurality of different portions of the sample; (e) the memory and processor including at least one memory for holding: (i) predetermined biohazard indicative signal information and predetermined non-biohazard indicative signal information; (ii) a plurality of groups of detected emission data for each of the plurality of different portions of the sample, (iii) identification of useful groups of detected emission data and associated portions of the sample; (iv) biohazard indicative statuses; and (v) a biohazard indicative conclusion; (f) the memory and processor further including at least one controller programmed to: (i) operate the means for directing excitation radiation, the source of excitation radiation, and the at least one detector to provide groups of detected emission data from the plurality of different portions of the sample; (ii) ascertain at least one of: (1) useful groups of detected emission data and (2) unusable groups of detected emission data from the plurality of groups of detected emission data, where useful groups of detected emission data are those that have at least one emission signal that is greater than a background signal by a predefined amount; (iii) compare data associated with each useful group of detected emission data with the predetermined biohazard indicative signal information and predetermined non-biohazard indicative signal information to produce a biohazard indicative status (e.g., classification) for each of the useful groups of detected emission data; and (iv) form a biohazard indicative conclusion based on a combination of biohazard indicative statuses for the plurality of useful groups of detected information and a relative separation of the portions of the sample that gave rise to such useful groups.

Numerous variations of the fourth and fifth system aspects of the invention are possible and include for example the numerous variations as noted above for first and second method aspects, mutatis mutandis, as well as other variations set forth in the dependent system claims provided in the '491 and '258 priority applications, and still further variations that will be understood by those of skill in the art from the teachings set forth herein or incorporated herein by reference. One of skill in the art, from a review of the teachings herein, will understand that numerous ways and means for directing excitation radiation are possible and include, for example: (1) a stage to move the sample relative to a source of excitation radiation (e.g. an X, a Y, an X & Y, an X & Y & Z stage, a rotational stage or the like); (2) at least one controllable scanning mirror for scanning the excitation radiation; (3) a pump or slidable plug in a flow channel that can be used to push or pull the fluid through the channel wherein the plug may be moved by a magnet, a vacuum, gas pressure, a linear motor, or the like; (4) a movable aperture that allows excitation radiation to strike a sample at a single location at any given time; (5) a movable aperture that allows only emission radiation from a single location, at any given time, to reach a detector; or (6) a combination of two or more of (1)-(5). In some other variations, the at least one controllable scanning mirror may include: (a) a galvanometer scanner, (b) a stepper motor scanning system, (c) a rotational scanning mirror system, (d) a tip/tilt scanning mirror system, (e) an oscillating mirror system, (f) a flying spot scanner, (g) a polygonal scanning mirror system, (h) a raster scanning system, (i) a dither mirror scanning system, (j) an oscillating mirror scanning system, or (k) a scanning system capable of two dimensional scanning. In some variations, the means may also include motors or other actuators along with a programed computer, controller, or other electronic circuitry.

In a sixth aspect of the invention, a system for identifying a selected biohazard signature in a complex sample, includes: (a) means for providing excitation radiation onto a sample to produce emission radiation; (b) means for providing detection of spectrally differentiated emission radiation originating from each of a plurality of different locations on the sample; (c) at least one means for holding: (i) predetermined biohazard indicative signal information and/or predetermined non-biohazard indicative signal information; (ii) a plurality of groups of detected emission data for the plurality of different locations of the sample; (iii) identification of useful groups of detected emission data from the different sample locations; (iv) biohazard indicative statuses; and (v) biohazard indicative conclusions; (d) at least one means for: (i) operating the means for providing excitation radiation and the means for providing detection of spectrally differentiated emission radiation to provide groups of detected emission data from a plurality of different portions of the sample; (ii) means for distinguishing groups of emission data from the plurality of different locations including: (1) useful groups of detected emission data, (2) unusable groups of detected emission data, wherein useful groups of detected emission data are those that have at least one emission signal that is greater than a background signal by at least a defined amount; (iii) means for comparing data associated with each useful group of detected emission data with the predetermined biohazard indicative signal information and/or the predetermined non-biohazard indicative signal information to produce a biohazard indicative status or membership classification for each of the useful groups of detected emission data, wherein positive membership for a group is assigned if the detected emission data for the group is deemed closer to the information associated with samples known to contain the biohazard signature than to information associated with samples known not to contain the biohazard signature, and wherein negative membership is assigned to groups including detected emission data for those groups that are deemed closer to information associated with samples known not to contain the biohazard signature than to information associated with samples known to contain the biohazard signature; and (iv) means for forming a biohazard indicative conclusion based on a combination of biohazard indicative statuses from the plurality of useful groups of detected information and the relative separations of the different portions of the sample associated with such useful groups wherein a positive biohazard signature presence is concluded if a minimum threshold for spatial grouping of the positive membership groups is found.

A first variation of the sixth aspect of the invention additionally includes the means for comparing being configured to use baseline spectroscopic data from a plurality of baseline samples known to contain the biohazard signature and baseline samples known not to contain a biohazard signature, wherein the baseline spectroscopic data is created using a method, including: (a) using one or more test methods of acceptable reliability to determine whether a biohazard signature of interest is present within each of a plurality of the baseline samples; (b) exposing each baseline sample to excitation radiation and reading resulting emission radiation for a plurality of wavelength bands from each of a plurality of locations on each of the baseline samples; and (c) separating the baseline spectroscopic data from the baseline samples into at least two groups including one group known to contain the biohazard signature and one group known not to contain the signature.

A second variation of the sixth aspect of the invention additionally includes the means for comparing being configured to use information selected from a group consisting of: (1) data from samples known to contain the biohazard signature, (2) data from samples known to not contain the biohazard signature, (3) both data from samples known to contain the biohazard signature and data from samples known not to contain the biohazard signature, (4) information that has been derived from data from samples known to contain the biohazard signature, (5) information that has been derived from data from samples known to not contain the biohazard signatures, (6) information that has been derived from the data from both samples known to contain the biohazard signature and samples known not to contain the biohazard signature.

Additional variations of the sixth aspect are possible and include, for example, incorporation of a device to aid in controlling the exposure or the reading of emission radiation from selected locations selected from the group consisting of: (1) a movable stage to move a sample relative to sample excitation components and emission radiation detection components when obtaining emission data from the plurality of locations on the sample, (2) a movable stage to move one or both sample excitation radiation components and/or emission radiation detection components relative to a sample that is held in a fixed position relative to a housing between obtaining emission data from the plurality of locations on the sample, (3) a scanning system that changes a path taken by excitation radiation and/or emission radiation when obtaining emission data from the plurality of locations on the sample, (4) a flow of sample material past a fixed detection location when obtaining emission data from the plurality of locations on the sample, (5) a movable aperture that allows excitation radiation to strike a sample at a single location and emission radiation to reach a detector from a single location and moving the aperture to obtain emission data from the plurality of locations on the sample, (6) a movable aperture that allows excitation radiation to strike a sample at a single location and thus allows only emission radiation from such location to reach a detector at any given time and moving the aperture to obtain emission data from the plurality of locations on the sample, (7) a movable aperture that allows only emission radiation from a single location to reach a detector at any given time and moving the aperture to obtain emission data from the plurality of locations on the sample, (8) a multiple path transmission array to control which location on a sample provides emission radiation for detection and moving or rotating the transmission array to allow emission radiation from the plurality of sample locations to be detected.

Other variations to the sixth aspect of the invention are possible and include, for example, the numerous variations as noted above for other aspects of the invention, mutatis mutandis, as well as other variations set forth herein, with still further variations being understood by those of skill in the art from the teachings set forth herein or incorporated herein by reference. In particular, numerous hardware and software variations for the means called for in the sixth aspect of the invention are possible and will be understood by those of skill in the art upon review of the teachings herein and include those components, devices, and systems as noted herein with respect to the various other aspects and the embodiments of the invention set forth herein or as incorporated herein by reference. Examples include: (1) the means for providing excitation radiation being a source of EM radiation, such as a source of UV radiation, such as a laser, a semiconductor laser, a hollow cathode laser, an LED, or the like; (2) the means for providing detection being or including a photodiode (such as a CCD, PN, PIN, or avalanche), a photodiode array (such a CCD, PN, PIN, or avalanche array), a photomultiplier tube, or the like; (3) means for holding may include computer memory of desired speed and capacity, e.g. RAM, or a data storage device like ROM, EPROM, flash memory, a hard drive, an optical storage device, or the like; (4) means for operating the means for providing excitation radiation and the means for providing detection may include one or more controllers, one or more programmed computers, one or more other hardwired electronic devices, along with one or more power sources and wired or wireless connections as required; (5) means for distinguishing groups of emission data, means for comparing data, and the means for forming a biohazard indicative conclusion, may include one or more programmed computers or hard wired electronic circuit elements configured to provide the required functions under the control of, or implementing, appropriate programs or algorithms, such as those described herein or those derived from AI or machine learning algorithms and/or training. Of course, the above noted means, as necessary, may also include other optical elements, other mechanical elements, other electrical or electronic components, actuators, programmed computer or controllers, hardwired electronic circuits, input and output components, or the like.

Seventh to tenth aspects of the invention provide methods as respectively set forth in claims 1, 101, 201, and 301 of related U.S. Patent Application No. 63/051,258.

Examples of variations of the seventh to tenth aspects of the invention are set forth in the dependent method claims of related U.S. Patent Application No. 63/051,258.

Eleventh to fourteenth aspects of the invention provide systems as respectively set forth in claims 1001, 1101, 1201, and 1301 of related U.S. Patent Application No. 63/051,258.

Example variations of the eleventh to fourteenth aspects of the invention are set forth in the dependent system claims of related U.S. Patent Application No. 63/051,258.

In a fifteen aspect of the invention, a method for identifying presence of a SARS-CoV-2 or COVID-19 biohazard signature in a sample, includes: (a) exposing a sample to deep UV excitation radiation having a wavelength and reading resulting native fluorescence emission radiation in a plurality of wavelengths bands from each of a plurality of locations on the sample, wherein individual locations are exposed and read to produce emission readings, and then followed by movement of the sample relative to an exposure/emission location in preparation for reading a subsequent location, wherein the wavelength is selected from the group consisting of: (i) below 300 nm, (ii) below 275 nm, and (iii) below 250 nm, wherein the plurality of distinct bands are selected from the group consisting of: (i) more than 10 bands, (ii) more than 30 bands, (iii) more than 60 bands, (iv) more than 120 bands, (v) more than 200 bands, (vi) more than 400 bands, (vii) more than 600 bands, and (viii) more than 800 bands, and wherein the plurality of locations on the sample is selected from the group consisting of: (i) more than 200 locations, (ii) more than 350 locations, (iii) more than 500 locations, and (iv) more than 650 locations; (b) on a location-by-location basis, performing a first level analysis to determine which locations provide emission radiation that meets signal threshold requirements by exceeding background noise by a factor selected from the group consisting of: (i) at least 3, (ii) at least 5, and (iii) at least 7; (c) for each emission radiation location meeting signal threshold requirements, performing a second level membership analysis to assign a class membership to individual locations which have readings indicative of potential relevance to a SARS-CoV-2 or COVID-19 biohazard signature presence, wherein the second level membership analysis includes use of a KNN algorithm, with a K value selected from the group consisting of: (i) at least one, (ii) at least three, and (iii) at least five and wherein the class membership is divided into at least two categories selected from the group consisting of: (1) positive membership locations wherein emission radiation for the location is more closely aligned to biohazard signature presence than to biohazard signature non-presence, and (2) negative membership locations include those locations where the emission radiation for the location is closer to biohazard signature non-presence than to biohazard signature presence; and (d) performing at least one additional level of analysis involving spatial relationships between a plurality of locations having positive membership wherein a SARS-CoV-2 or COVID-19 biohazard signature presence for the sample is determined when the sample includes a number N of neighboring locations having positive membership with no more than M intervening locations having negative membership, wherein N is selected from the group consisting of: (i) at least 3, (ii) at least 7, (iii) at least 11, (iv) at least 15, and (v) at least 25, and wherein M is selected from the group consisting of: (i) 0, (ii) no more than 1, (iii) no more than 5% of N, (iv) no more than 10% of N, (v) no more than 20% of N, (vi) no more than 30% of N, and (vii) no more than 40% of N.

In a sixteenth aspect of the invention, a system for identifying a SARS-CoV-2 or COVID-19 signature in a complex sample, includes: (a) means for providing excitation radiation onto a sample to produce emission radiation, wherein the means for providing excitation radiation is selected from the group consisting of: (i) a laser, (ii) a semiconductor laser, and (iii) an LED, and may or may not include additional optical elements; and wherein the excitation radiation is in the form of UV excitation radiation and has a wavelength selected from the group consisting of: (i) below 300 nm, (ii) below 275 nm, and (iii) below 250 nm; (b) means for providing detection of spectrally differentiated emission radiation originating from each of a plurality of different locations on the sample, wherein the means for providing detection includes a wavelength separating element (e.g. one or more dispersive optical elements, e.g.

diffraction gratings or prisms, for splitting the emission radiation into a plurality of distinct bands, one or more filters, one or more tunable filters, and/or one or more apertures), at least one detector for providing a signal strength value for each distinct band (e.g. a CCD, CCD array, a photodiode, a photomultiplier tube), and at least one computer controlled system for relatively moving a sample with respect to an exposure and/or emission location; wherein the plurality of distinct bands is selected from the group consisting of: (i) more than 200 bands, (ii) more than 400 bands, (iii) more than 600 bands, and (iv) more than 800 bands; wherein the plurality of different locations is selected from the group consisting of: (i) more than 200 locations, (ii) more than 350 locations, (iii) more than 500 locations, and (iv) more than 650 locations; and wherein the computer controlled system for relatively moving is selected from the group consisting of: (i) a stage to move the sample relative to an excitation radiation exposure location to provide excitation radiation to different portions of the sample, (ii) at least one scanning mirror for scanning the excitation radiation to different portions of the sample, (iii) a flow channel capable of holding and flowing the sample passed an exposure location such that different portions of the sample in turn receive excitation radiation based on the flow of the sample and relative positioning of the different portions of the sample within the flow channel, (iv) a movable aperture that controls which portion of a sample receives excitation radiation; and (v) a movable aperture that controls a location on the sample that provides emission radiation to the at least one detector; (c) at least one memory for holding: (i) information from samples known to contain SARS-CoV-2 or COVID-19 signatures and samples known not to contain SARS-CoV-2 or COVID-19 signatures, (ii) a group of detected emission data for each of the plurality of different locations on the sample, (iii) identification of useful groups of detected emission data from the different locations on the sample, and (iv) a biohazard indicative classification for each sample location; (d) at least one means, selected from the group consisting of: (i) at least one electronic circuit, and (ii) at least one programmed controller, for: (a) operating the means for providing excitation radiation and the means for providing detection of the spectrally differentiated emission radiation to provide a group of detected emission data from each of a plurality of different locations on the sample; (b) ascertaining whether a group of spectra from each location meets a threshold value for usefulness, where useful groups of detected emission data are those that have at least one emission signal that is greater than a background signal by a factor selected from the group consisting of: (i) greater than 2, (ii) greater than 4, (iii) greater than 6, and (iv) greater than 8; (c) comparing, directly or indirectly, data associated with each useful group of detected emission data to information from samples known to contain SARS-CoV-2 or COVID-19 signatures and samples known not to contain SARS-CoV-2 or COVID-19 signatures to produce a biohazard indicative class membership for each of the useful groups of detected emission data, wherein the comparisons include use of a KNN algorithm, with a K value that is selected from the group consisting of: (i) at least one, (ii) at least three, and (iii) at least five, and wherein the class membership is divided into at least two categories selected from the group consisting of: (1) positive membership locations wherein emission radiation for the locations are more closely aligned to biohazard signature presence than to biohazard signature non-presence, and (2) negative membership locations include locations where the emission radiation for the locations is closer to biohazard signature non-presence than to biohazard signature presence; and (d) performing a proximity analysis of locations with SARS-CoV-2 or COVID-19 positive membership to determine if a sufficient level of proximity exists between the locations with positive membership to produce a biohazard indicative conclusion that a sample has a SARS-CoV-2 or COVID-19 signature presence or whether insufficient proximity exists so that a SARS-CoV-2 or COVID-19 signature is not present, wherein a SARS-CoV-2 or COVID-19 biohazard signature presence for the sample is determined when the sample includes a number N of neighboring locations having positive membership with no more than M intervening locations having negative membership, wherein N is selected from the group consisting of: (i) at least 3, (ii) at least 7, (iii) at least 11, (iv) at least 15, and (v) at least 25; and wherein M is selected from the group consisting of: (i) 0, (ii) no more than 1, (iii) no more than 5% of N, (iv) no more than 10% of N, (v) no more than 20% of N, (vi) no more than 30% of N, and (vii) no more than 40% of N.

Additional variations to the above aspects include detecting the presence, or lack of presence of, specific variations or variants of SARS-CoV-2, and/or specific variations or variants of the associated COVID-19 disease.

Further aspects of the invention will be understood by those of skill in the art upon review of the teachings herein. These other aspects of the invention may, for example, provide various combinations of the aspects presented above as well as provide other configurations, structures, functional relationships, and processes that have not been specifically set forth above.

BRIEF DESCRIPTION OF THE DRAWINGS

FIG. 1A provides a block diagram of a spectroscopic method according to a first embodiment of the invention for drawing a biohazard conclusion about a subject, location, or material based on analysis of a complex, in situ or in vitro, sample that is being analyzed to ascertain the presence, or likely presence, of a signature associated with the specific biohazard or signatures associated with biohazards of interest.

FIG. 1B provides a block diagram of a method of establishing baseline spectroscopic data for in situ or in vitro samples from a subject, location, or material that are known to contain a biohazard signature of interest and for samples known not to contain the biohazard signature of interest wherein such baseline spectroscopic data may be useful in implementing various embodiments of the invention involving the categorization of samples for which a biohazard signature determination is to be made.

FIG. 2B1 provides a flowchart of an example method for identifying the usefulness of spectral information for each of a plurality of sample measurement locations as may be used in Block I of FIG. 2A.

FIG. 2B2 provides a flowchart of a second example method for identifying the usefulness of spectral information for each of a plurality of sample measurement locations as may be used in Block I of FIG. 2A wherein the method may utilize a predefined criteria or may use a criteria that is fixed by an algorithm training process that helps provide optimized biohazard signature conclusions and wherein the method may use a wavelength-band-by-wavelength-band comparison of measured spectral data to background information where the measured data for a minimum number of bands exceeds background information data by a desired factor where X may be predetermined or defined during a training process.

FIG. 2C1 provides a block diagram illustrating two different predetermined signature/signal information examples.

FIG. 2C2 provides a block diagram of a number of example forms, or formats, that predetermined information may take.

FIG. 2C3 provides a block diagram of a number of examples of supplemental sample information that may accompany samples and even predetermined signature/signal information that may be used in enhancing, or fine tuning, conclusions that are reached by the method of FIG. 2A.

FIG. 2C4 provides a block diagram of four example signature conclusions that may accompany predetermined signature/signal samples.

FIG. 2D1 provides a flowchart of an example process that may be used in implementing Block J of FIG. 2A to provide a location-by-location classification or preliminary conclusion about potential biohazard signature presence for each such location but not for a sample as a whole.

FIG. 2D2 provides a block diagram of four example signature classifications that may be applied to each location.

FIG. 2D3 provides a block diagram providing seven example processes that may be used in implementing Block E of FIG. 2D1.

FIG. 3 provides a flowchart of a spectroscopic method for determining whether a biohazard signature is present in a sample according to a third embodiment of the invention where the method specifically uses a comparison of sample data with data for samples containing the biohazard signature and those not containing the biohazard signature.

FIG. 4 provides a schematic representation of a system according to a fourth embodiment of the invention that may be used for providing analysis of unknown samples for biohazard signature identification (i.e. determination of direct or indirect biohazard presence) wherein the system provides a majority of the components of an analytical instrument within a housing or package but where the instrument is provided with external control, power, data processing and analysis hardware, and an external stage for providing movement of an external sample relative to a fixed location of excitation radiation exposure and emission radiation generation so as to provide for a plurality of sample locations from which spectral information can be gathered and used along with spatial relationships of multiple sample locations in identification assessments.

FIG. 25 provides a schematic illustration of a system according to a twenty-fifth embodiment of the invention along with a table setting forth sample components.

DETAILED DESCRIPTION OF PREFERRED EMBODIMENTS OF THE INVENTION

Figure 2A:
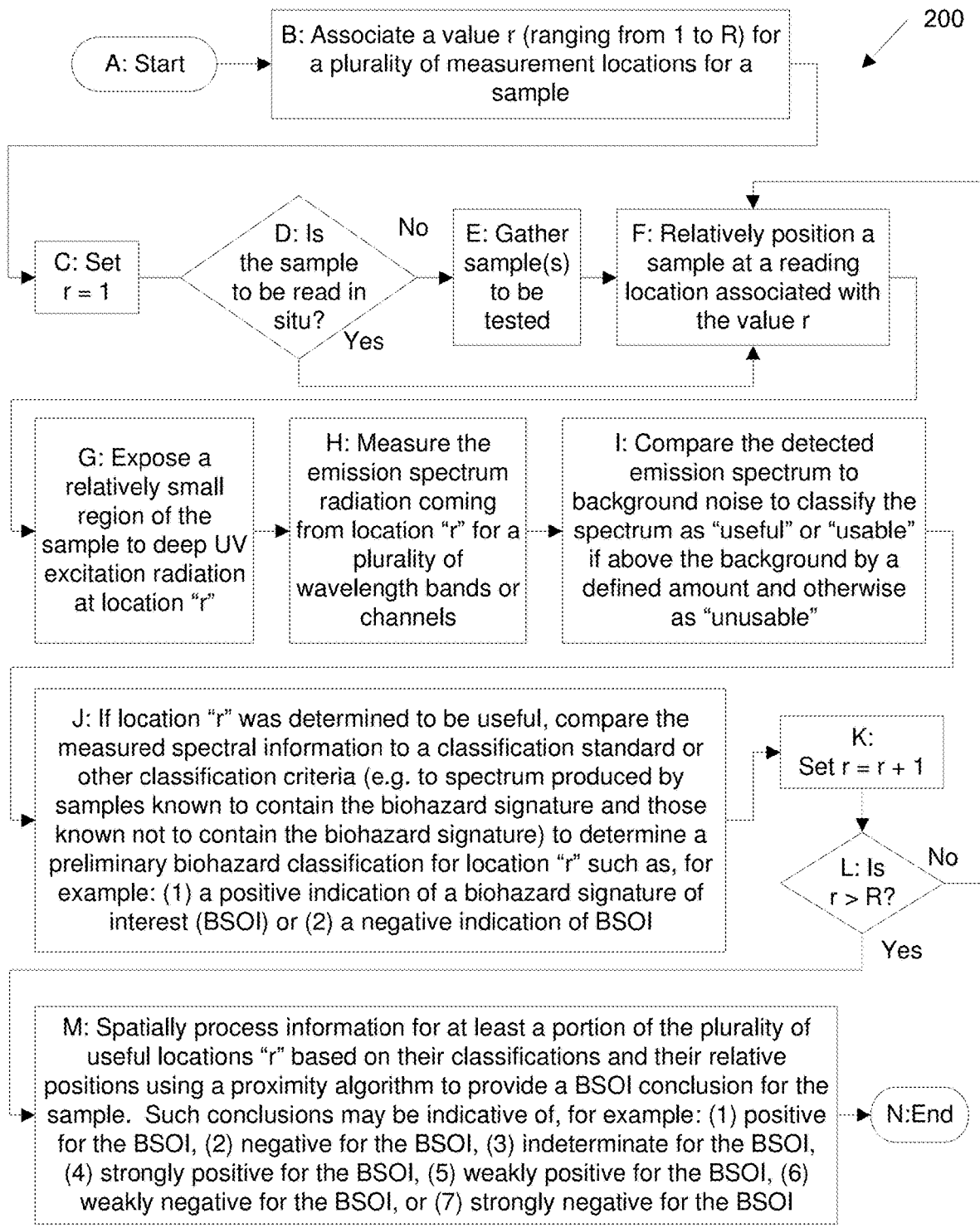
FIG. 2A provides a flowchart of a spectroscopic method for determining whether a biohazard signature is present in a sample according to a second embodiment of the invention.

Embodiments of the present invention provide spectroscopy methods, apparatus, subsystems, and/or systems for rapidly processing in situ or in vitro samples in, on, or taken from, subjects (e.g., human, animal, or plant), inanimate objects, locations, or materials for identifying the presence of one or more biohazard signatures of interest. The biohazard signature(s) being sought may take a variety of forms and may be associated with a presence of the biohazard such as a current presence of the biohazard; a current illness, disorder, infliction, infection, or the like, caused by or associated with the biohazard; a past illness, disorder, infliction, infection, or the like, caused by or associated with the biohazard; or an immunological response of a subject to a past illness, disorder, infliction, infection, or the like, caused by or associated with the biohazard; and possibly even a current state, or severity, of an illness, disorder, infliction, infection, or the like, caused by or associated with the biohazard. Biohazards of interest need not be limited to those that provide a direct risk to humans but also to those that directly infect, injure, or otherwise harm, animals such as pets, wild animals, farm animals, or livestock, or materials they feed on or that otherwise provide habitats for them. In some embodiments, biohazards of interest may infect, injure, or otherwise harm plants whether they be agricultural in nature, wild, or decorative.

Biohazard signatures may provide a direct molecular identification of a biohazard itself such as, for example, a direct detection of a specific bacteria or virus. In some embodiments, for example such a biohazard might be (a) a coronavirus, (b) a SARS-CoV-2 virus or variation thereof, that may cause coronavirus disease 2019, i.e., COVID-19, or a variation thereof, (c) an influenza virus (e.g., A, B, C, or D), and (d) a hemorrhagic virus, e.g., an ebolavirus, a hantavirus, the Marburg virus, or the like. Biohazard signatures may not directly identify a bacterium, a virus, a fungus, a yeast, a mold, a prion, or a biological toxin (e.g., like ricin) though that may be the case in some embodiments. In some embodiments, the biological signature instead might be an identifier of an action or effect that the biohazard has or had on a subject's body such as, for example, a molecular indicator of a non-infecting presence of a biohazard, a molecular indicator of an infecting presence of a biohazard, and a molecular indicator of a past infecting presence of a biohazard (e.g., an immunoassay).

Different embodiments may use different types of complex materials as samples and such samples may be extracted in different ways or taken from different parts of a subject's body or from an inanimate surface or volume. In some embodiments, samples may include material that is extracted from various sources which may include, for example: (a) a nasal fluid from a sinus passage of a subject that is being evaluated for the biohazard signature, (b) saliva or other material from a mouth of a subject that is being evaluated for the biohazard signature, (c) sputum or other material from a throat of a subject that is being evaluated for the biohazard signature, (d) rectal solids or fluids extracted from or dispensed from a rectum or colon of a subject, (e) material present in or on a wound on a subject that is being evaluated for the biohazard signature, (f) skin or material present on a region of skin of a subject that is being evaluated for the biohazard signature, (g) material from an ear canal of a subject that is being evaluated for the biohazard signature, (h) fluid from around an eye of a subject that is being evaluated for the biohazard signature, (i) a nail (e.g. a fingernail or toenail) of a subject that is being evaluated for the biohazard signature, (j) blood from a subject that is being evaluated for the biohazard signature, (k) blood from a surface of an area being evaluated for the biohazard signature, (l) a sample of a blood extract (e.g. plasma or serum) from a subject being evaluated for the biohazard signature, (m) a fluid sample from the respiratory tract of a subject being evaluated for the biohazard signature, (n) a tissue sample from the respiratory tract of a subject being evaluated for the biohazard signature, (o) material from a lesion on a subject being evaluated for the biohazard signature, (p) a sample of glandular exocrine secretions from a subject being evaluated for the biohazard signature, (q) a sample of secretions from an exposed portion of a subject's body, e.g. from the finger prints or from palm prints, and (r) a sample taken from, or read, directly from a surface, a fluid, or a gas in a region being examined for the biohazard signature. Looked at from a different perspective, samples may include different materials and be extracted in a variety of different ways with the material or method of extraction potentially being captured as part of a sample history or diagnostic variable. Such variables may or may not form part of the process of interpreting biohazard signature presence or in training an algorithm to provide improved biohazard signature identification. In some embodiment variations, the material, for example, may come from one or more of: (a) air, (b) water, (c) material in the air that has been condensed from the air and then placed on a sample location, (d) material in the air that has been condensed directly on a sample location by lowering the temperature of the air, (e) material in the air that has been condensed onto a sample location by lowering the temperature of the air and by blowing or drawing the air past the sample location, (f) material transferred to a surface by touching, (g) material transferred to a surface by sneezing, (h) material transferred to a surface by coughing, (i) material found on the inside of a mask or face shield prior to usage, (j) material found on the inside of a mask or face shield after usage, (k) material found on the outside of a mask or face shield after usage, or (l) material extracted from an outer surface of a glove after usage. Samples may be collected in a number of different ways with the method of collection potentially being captured as part of a sample history or diagnostic variable, where such collection may include, for example: (a) scraping a region to collect sample material to be tested, (b) swabbing a region to collect sample material to be tested on a swab, (c) evaporating a liquid to leave a sample of higher concentration, (d) extracting a fluid by suction using a syringe or a syringe with a needle; or (e) wiping, and the like.

In some embodiments, samples may be placed within a housing of an analytical instrument, in others an in vitro sample may be placed at a target location in proximity to an analytical instrument, while in still other embodiments, the sample may remain in an in vivo or in situ state while an analytical instrument or working head of an analytical instrument is located in proximity to such in vivo or in situ target location. In some embodiments, samples may be read directly from an extraction material or tool, or they may be transferred from an extraction tool or material to a target surface or material, for example: (a) in some embodiments, when a swab is used to collect a sample, the swab itself may function as a target surface for incident exposure radiation and resulting emission radiation production, (b) in some other embodiments, a swab may be used for collection which in turn may be subjected to a solvent to separate the sample material from the swab with the resulting solution (i) being subjected to excitation radiation, (ii) being condensed and then subjected to excitation radiation, or (iii) being condensed and allowed to spread on a target surface and allowed to dry prior to exposure to excitation radiation; and (c) in some other embodiments, a swab may be directly wiped against a target surface to transfer part of a sample to the target surface which is then subjected to excitation radiation.

In some embodiments, a sample may be located on a surface at the time of exposure to excitation radiation, such as, for example: (a) a surface of material that is otherwise sterile but for the presence of the complex sample, (b) a metal surface that is otherwise sterile but for the presence of the complex sample, (c) a stainless-steel surface that is otherwise sterile but for the presence of the complex sample, (d) an otherwise sterile swab which has swabbed a surface for which the presence of the biohazard signature is to be determined, (e) a non-sterile surface for which the presence of the biohazard signature is to be determined, (f) an inside surface of a face mask or face shield that was worn by a subject for which the presence of the biohazard signature is to be determined, (g) an outside surface of a face mask or face shield that was worn by a subject for which the presence of the biohazard signature is to be determined, (h) a surface which has been cleaned for which the absence of the biohazard signature is to be confirmed, (i) a skin surface of a subject to be tested, (j) a surface within a wound on a subject to be tested, (k) a surface within a lesion, (l) a print region of a finger or toe; or (m) a palm of a hand.

FIG. 1A provides a block diagram of a spectroscopic method according to a first embodiment of the invention for drawing a biohazard conclusion about a subject, location, or material based on analysis of a complex, in situ or in vitro, sample that is being analyzed to ascertain the presence, or likely presence, of a signature associated with the specific biohazard or biohazards of interest. The method involves, in some implementations, (1) a first step of sample exposure and emission radiation data gathering from a plurality of sample locations, (2) a second step of removal of spectral data that is not sufficiently above background noise, (3) a third step of classification of spectral data coming from different locations on a sample as biohazard positive or negative, and (4) a fourth step of performing spatial analysis of the biohazard classified information wherein a proximity grouping of multiple readings with biohazard signature relevance is used, alone or in combination with other data or analysis, in determining a biohazard signature presence for the sample and thus a biohazard signature presence conclusion for the subject, location, or material.

In some embodiments, the conclusion concerning the biohazard signature presence or lack thereof may form an output of the system, while in other embodiments, such a conclusion may be used as an input for information that will be provided wherein the information may be more nuanced or less nuanced. In some embodiments, the biohazard indicative result may (a) be the same as the biohazard indicative conclusion, (b) be less nuanced than the biohazard indicative conclusion, (c) be either an indication of biohazard presence or non-biohazard presence, (d) be an indication of biohazard presence, non-biohazard presence, or indeterminate biohazard presence, or (e) be an indication of biohazard presence, non-biohazard presence, possible biohazard presence, or indeterminate biohazard presence. In some embodiments, the conclusion may be targeted to having a false positive error (e.g., as compared to conclusions provided by RT-PCR (reverse transcriptase polymerase chain reaction) or real-time RT-PCT) that is (a) less than 30%, (b) less than 20%, (c) less than 10%, (d) less than 5%, (e) less than 2%, or possibly even (f) less than 1%. In some embodiments, the conclusion may be targeted to having a false negative error (e.g., when compared to a non-biohazard conclusion resulting from an RT-PCR or real-time RT-PCT test) that is (a) less than 30%, (b) less than 20%, (c) less than 10%, (d) less than 5%, (e) less than 2%, or possibly even (f) less than 1%.

The activities of exposing and data gathering of step 1 of FIG. 1A may involve applying excitation radiation, receiving emission radiation, and gathering data from tens, hundreds, or even thousands of locations. The excitation radiation may take a variety of forms and may be from narrow band or broadband sources. The excitation radiation is preferably in the UV range, e.g., with a wavelength, or upper wavelength limit of less than 350 nm (nanometers), less than 300 nm, less than 275 nm, or even less than 250 nm. The sources of such radiation may include LEDs, LDs (laser diodes), CW laser sources, pulsed laser sources, unpolarized ultraviolet sources. In different embodiments, the upper limit on excitation radiation wavelength may be a hard limit or a soft limit. In the case of a hard limit, essentially no excitation radiation (i.e., less than 1%) is above the upper limit. In the case of a soft limit, for example, less than 20% of the excitation radiation has a wavelength above the upper limit or perhaps while in others, less than 10% of the excitation radiation has a wavelength above the upper limit. In some embodiments, filtering or use of wavelength separation components may be used to limit the quantity of excitation radiation above the upper limit that is allowed to reach a sample.

In some embodiments, excitation radiation supplied in pulses may have temporal pulse widths (or times) that are greater than 100 ns (nanosecond), greater than 1 μs (microsecond), or even greater than 10 μs. In some embodiments, power density of excitation radiation may be limited to an amount that will not cause adiabatic heating damage or other damage to the material giving rise to the biohazard signature. In some embodiments, excitation radiation may be supplied at a power level, over a time, and with a number of repetitions that will not substantially inhibit repeated detection of the biohazard signature. In some embodiments, not substantially inhibiting detection means detection upon N repeated similar exposures will not result in a detection reduction that is greater than 50%, more preferably not greater than 20%, and even more preferably not greater than 10%, where N is selected from the group consisting of at least 2, more than 5, more than 10, or even more than 20. In other embodiments, the power level, time, and number of repetitions used in applying excitation radiation will not result in an increased presence of false negatives or false positive conclusions beyond an acceptable level (e.g., no more than 25%, preferably no more than 10%, more preferably no more than 5%, even more preferably no more than 2%, and more preferably by no more than 1%, and most preferably less than 1%).

In some embodiments, the excitation radiation may be supplied over a broad area (e.g., more than 20% of the sample area, more than 50% of the sample area, and even all of the sample area) in which case a means is used to ensure, i.e. a means for ensuring, that emission radiation reaching a detector or plurality of detector elements comes from only a relatively small region of the sample (e.g. at any given time only excitation radiation from localized portion of the sample reaches a detector, or radiation from a plurality of different localized regions of the sample reach a corresponding plurality of different detector elements). In other embodiments, the excitation radiation may take a form that provides a relatively small exposure region (e.g., less than $1/100$th or even less $1/1000^{th}$ of the surface area of the sample) at any given time. In some such embodiments, the excitation may be provided in the form of a beam or exposure spot having a width of: (a) less than 1 mm, (b) less than 0.5 mm, (c) less than 0.2 mm, (d) less than 0.1 mm, (e) less than 0.05 mm, (f) less than $1/10$ of a corresponding width of the sample location, (g) less than $1/50$ of a corresponding width of the sample location, or even (h) less than $1/100$ of a corresponding width of the sample location. In some embodiments, such a beam or spot size may be substantially circular in nature (i.e. minimum to maximum diameter ratio is between 0.95 and 1.05), or it may have an elongated form with a maximum width in one axis and a minimum width in a perpendicular axis, where for example the ratio of the two near a focal point might be (a) less than 5.0, (b) less than 2.0, (c) less than 1.5, (d) less than 1.25, and (e) less than 1.1. In other embodiments, the beam shape may take on different forms. In some embodiments, the means for ensuring may include one or more optical elements such as apertures, lenses, fiber optics, mirrors, absorbers, and the like. An aperture or set of two or more apertures that are displaced along an optical axis may be configured such that only radiation coming from a relatively small portion of the sample area can reach a particular detector or a particular cell of a detector.

The emission radiation is measured over a desired range of wavelengths, in the form of resulting emission spectra, e.g., in relative power vs. wavelength, or signal strength vs. wavelength). The emission radiation may be measured over a predetermined set of wavelengths where anticipated fluorescence, Raman, Rayleigh, phosphorescence radiation may be read. For example, the emission radiation may range from 250 nm or less to 700 nm or more. In other embodiments, the emission radiation may be read over a narrower range of wavelengths with either end truncated or with one or more intermediate portions of the spectral range not read or at least not utilized. The desired range of wavelengths to be analyzed may be divided into a number of channels or bands (e.g. from tens of bands to hundreds of bands, or even one or multiple thousands of bands) with each channel or band of a desired wavelength width (e.g. each having a width as large as tens of nanometers or more to a width as small as tenths of nanometers or less). In some embodiments, the width of each band may be constant while in others, the width, or effective width, may vary from band to band. The gathered information may be normalized, processed to yield band-to-band ratio information, or processed in some other manner to allow direct or indirect comparison to data from other locations or to data from readings taken from samples with known biohazard signature classifications.

In some embodiments, relative positioning of the sample and an exposure location or emission location may include: (a) relative movement of the beam of excitation radiation from one sample position to another sample position; (b) relative movement of the beam on a sample location to provide improved focusing of the beam of excitation radiation on the sample position; (c) relative movement of the sample position substantially perpendicular to an optical axis selected from the group consisting of: (1) an optical axis perpendicular to a plane containing a surface of the sample that is being read, (2) an incident optical axis of the beam of excitation radiation, (3) an emission optical axis extending from an exposed portion of the sample to a first of the at least one optical element, and (4) an intermediate optical axis that is between the incident and emission optical axes; (d) relative movement of the sample position substantially parallel to an optical axis selected from the group consisting of: (1) an optical axis perpendicular to a plane containing a surface of the sample that is being read, (2) an incident optical axis of the beam of excitation radiation, (3) an emission optical axis extending from an exposed portion of the sample to a first of the at least one optical element, and (4) an intermediate optical axis that is between the incident and emission optical axes; (e) relative movement of the sample position to allow focusing of emission energy onto a selected optical element; (f) the relative movement wherein the sample position is moved, and (g) the relative movement wherein at least an excitation axis and an emission axis are moved. In some embodiments, substantially, in an angular sense, as used above, means (a) within 10 degrees of a target value or axis, (b) more preferably within 5 degrees of a target value or axis, (c) even more preferably within 2 degrees of a target value or axis, or (d) most preferably within 1 degree.

In some embodiments, where a stage provides relative movement of a sample and an exposure location, the stage may be configured to provide X and Y movement substantially perpendicular to an optical axis. In other embodiments, such a stage may be configured to provide a single linear axis of movement (X or Y) or rotational or angular movement about a fixed axis where the fixed axis may be parallel to an optical axis. In other embodiments, such stages may also provide one or more of Z movement (parallel to an optical axis), radial movement in conjunction with rotational motion, or angular motion in a plane containing the Z axis, or even hexapod motion.

The first level analysis of step 2 of FIG. 1A may involve the removal of data associated with detection locations when the data does not meet threshold requirements or as a result of other considerations. The first level analysis might result in a requirement to retake all data from a given sample if too many readings are removed from further consideration (e.g., data associated with more than 95%, more than 80%, more than 65%, or even move than 50% of the sample locations is removed). Such an event might result in testing or inspection of the instrument, repositioning of the sample in the instrument, or the like. Such a result might trigger a conclusion that a new sample must be retaken to obtain a conclusive result within a desired error tolerance. Such additional activities may be limited to situations where a conclusion that the presence of a biohazard signature is negative (as may be reached in a subsequent step) or the conclusion is not otherwise positive (e.g., indefinite or indeterminate). In some embodiments, locations with removed data (i.e., unusable data) may be ignored in subsequent steps or may be used in such steps particularly in proximity determinations as two or more consecutive locations with positive classifications might have a different interpretation than multiple locations with positive classifications that are themselves separated by one or more locations with unusable data.

The second level analysis of step 3 of FIG. 1A may provide a binary classification of the data from any specific location being either positive for the biohazard or negative for the biohazard or alternatively it may provide a more nuanced classification for each location. Because of the complex nature of the samples being read, regardless of the classification system being used, further analysis will be performed based on the classifications assigned to the data from multiple locations of a given sample as will be discussed below with regard to analysis provided in Step 4 of FIG. 1A. The nature of the additional analysis may be dependent on the classification system being used and may or may not be varied based on an overview of the results obtained by the analysis of step (3). In one implementation, a negative or positive membership classification may be assigned to the spectral information from a given location on a sample being tested by comparing the spectrum to spectra associated with a plurality of samples known to contain the biohazard signature of interest and/or spectra associated with a plurality of samples known not to contain the biohazard signature of interest.

In different implementations, the classification of the second level analysis may provide classifications other than that of a binary separation. Whether a binary classification is used or a more nuanced system, the classification may be achieved in numerous ways, e.g., based on a priori methods, empirical methods, including trained artificial intelligence or machinine learning algorithms. For example, in some implementations, the biohazard indicative status for a given location and its useful signal group (e.g., classification) may consist of a plurality of: (a) biohazard present, (b) no biohazard present, (c) indeterminate biohazard status, and (d) a weighted biohazard indicative status (e.g., based on a consistency of the band-to-band, or band-to-band ratio, based on indicative status for each band or each selected band-to-band ratio of a given useful signal group).

In some implementations, a band-to-band based indicative status (e.g., subclassification) or selected band-to-band ratio-based indicative status (e.g., subclassification) may yield a classification for the location as whole that provides a rating dependent on how the emission signal data of a given useful signal group compares to the predetermined biohazard indicative signal information and the predetermined non-biohazard indicative signal information. In some implementations, a sum of the number of bands indicative of biohazard presence minus the sum of the number of bands indicative of biohazard not present may yield a value that is positive or negative to yield a positive or negative classification. In some such embodiments, a magnitude of the difference may further yield a strength factor to associate with the classification. In some embodiments, a comparison for a given band may be based on a comparison of a normalized value provided by the sample which is undergoing evaluation with normalized values from the predetermined biohazard indicative samples (or averaged normalized values and possibly standard deviations) and with normalized values from the predetermined non-biohazard indicative samples (or averaged normalized values and possibly standard deviations) for that band wherein the comparison will result in the band being provided a subclassification status based on which data set it more closely approximates or being assigned a neutral classification status if it is not closer to one or the other or is not closer to one or the other by an amount that exceeds a defined significance value. In some variations, not all bands may be used in the comparison while in others, some bands may be grouped together to form grouped bands that are used to yield the grouped subclassifications that are then used in determining an overall classification. In some variations, band-to-band comparisons may not be performed but ratios of values, or of normalized values, associated with selected bands may be determined and compared to yield subclassifications. In some variations, all possible ratios may be used and comparisons made while in others, only selected ratios or groups of ratios may be used to yield subclassifications or grouped subclassifications. The selection of bands to compare, groups of bands to compare, ratios to compare, or groups of ratios to compare may be determined a priori, or by empirical observation such as by use of a machine learning algorithm, training of the algorithm using samples with known biohazard presence or non-presence, testing results against other samples having known biohazard presence or non-presence but which are treated as samples to be evaluated, with the effectiveness of the trained algorithm being determined by how accurately the algorithm properly identifies the signature status of such samples. Such methods may also be used to evaluate other process variables and parameters in optimizing the process. One such machine learning algorithm might take the form of a KNN algorithm with different values of K evaluated along with some of other variables noted above or that would be apparent to those of skill in the art.

In embodiments where subclassifications are determined, or group classifications are determined, primary combining of such subclassifications and/or group classifications may yield a simple binary classification for each sample location or the combination may yield a more nuanced classification for each sample location. For example, in some embodiments, if the primary combination is a summing process, a positive sum may provide a provisional biohazard indicative status for a location that points toward the biohazard being present while a negative sum may provide a provisional biohazard indicative status for a location that points toward the biohazard not being present, while a magnitude of the sum or the magnitude of the sum divided by the number of bands, or the number of selected ratios, used in reaching the sum may provide a weighting to the provisional biohazard indicative status (or classification) for the location for the given useful signal group detection signal. A secondary combination or merging of the resulting classifications for each location may then be used to yield a result for the sample as a whole which again may be a simple binary status (e.g. positive or negative for biohazard signature presence), trinary status (e.g. positive, indeterminate, or negative for biohazard signature presence), quaternary status (e.g. positive, sample analyzed results were indeterminate, negative, or sample errors prevented status determination), or an even more nuanced status. The secondary combination may result from a simple use of positive and negative statuses from the individual locations from which a positive, negative, or more nuanced status for a sample as a whole may be ascertained or the secondary combination may be based on not only the positive and negative statues for the individual location but also on a weighting associated with those statuses whereby a positive, negative, or more nuanced status for a sample as a whole may be identified.

In some embodiments, a primary combination, or a second combination, may use threshold values to draw positive or negative conclusions only when criteria are sufficiently indicative of such conclusions along with indeterminate conclusions, or even faulty sample or faulty analysis conclusions, when certain threshold levels are not met. For example, if an insufficient number of, or percentage of, locations for a given sample have useful spectral values (i.e. a threshold value for the number of useful locations is not met) due to them not being sufficiently above background values, it may be possible to draw a positive biohazard present conclusion, if warranted by the analysis, but not a negative biohazard present conclusion. For example, if a sum of biohazard present subclassifications minus a number of biohazard not present subclassifications yield a positive number less than a certain value, TP, or a negative number above a certain value, TN, it may be most appropriate to provide an indeterminate classification than either a positive or negative classification as TP would function as a minimum positive threshold value for a positive classification and TN would function as a minimum negative threshold value for a negative classification to be applied. Similar thresholding values may be applied to secondary combinations analysis as well. In some embodiments, the optimal values may be set a priori or empirically, or even determined using a machine learning process where different thresholding values could be tested to determine an impact on determined false positives and/or negatives. In some embodiments, TP and TN may be the same amounts while in other embodiments, they may be different amounts.

As noted above, some embodiments may make use of trained artificial intelligence algorithms or machine learning algorithms. Such algorithms may take on a variety of forms such as (a) Instance-Based Algorithms which include, for example: (i) K Nearest Neighbor (KNN) algorithms, (ii) Learning Vector Quantization (LVQ) algorithms, (iii) Self-Organizing Map (SOM) algorithms, (iv) Locally Weighted Learning (LWL) algorithms, and/or (v) Support Vector Machines (SVM) algorithms which include, for example: (b) Dimensionality Reduction Algorithms which include, for example: (i) Principal Component Analysis (PCA) algorithms, (ii) Principal Component Regression (PCR), (iii) Partial Least Squares Regression (PLSR) algorithms, (iv) Sammon Mapping algorithms, (v) Multidimensionality scaling (MDS) algorithms, (vi) Projection Pursuit algorithms, (vii) Linear Discriminant Analysis (LDA) algorithms, (viii) Mixture Discriminant Analysis (MDA) algorithms, (ix) Quadratic Discriminant Analysis (QDA) algorithms, and (x) Flexible Discriminant Analysis (FDA) algorithms. In some embodiments, two or more of the above methods may be used in combinations especially where use of a Dimensionality Reduction Algorithm is followed by use of an Instance-Based Algorithms. In still other embodiments, other averaging or comparison approaches may be used or even repeated use of one or more of the above methods with different parameters (e.g., K values in KNN, where K may be as low as 1 or as high 20 or more and wherein a first pass may be set to a lower value than that used in a second or even a third pass) followed by comparison of the results to provide more nuanced classifications.

The third level analysis of step 4 of FIG. 1A may be based on a binary classification method being used in step 3 or on a more nuanced classification method being used in step 3. The analysis of step 4 provides a spatial analysis that looks for one or more groups of spatially connected similarly classified spectra to provide a conclusion regarding the sample overall (e.g. positive or negative; positive, negative, or indefinite; or positive, negative, indefinite, or faulty). The number of spatially connected locations and any allowed breaks in spatial connectivity may be based on the level of nuance in the classification and/or the specific method and parameters used in performing the analysis with the primary goal being the provision of a sample conclusion that is reliable within a certain tolerance of allowed false positive and false negative conclusions and with secondary goals of providing the conclusion within cost, timing, equipment, and staffing requirements. The spatial analysis of step 4 may be performed using one or more of the methods noted for use in step 3 or some other method. As a first example, reaching a positive conclusion (e.g., biohazard signature present) for the sample as a whole may require P1 positive classification locations within proximity of each other with no more than N1 negative classifications located therebetween. Alternatively, a positive conclusion may be reached by evaluation of a plurality of different parameters or relationships wherein a positive conclusion may result from a single one of the parameters or relationships meeting a first threshold level or a positive conclusion may result from multiple parameters or relationships existing at second threshold levels which may be lower than the level required for a single one of the parameters or relationships. For example, in addition to, or as an alternative to the first example for reaching a positive conclusion, instead of looking for a single set of P1 positives with no more than N1 intermediate negatives, the sample readings may be evaluated to determine if S2 subsets of the data exist with each having at least P2 positives and no more than N2 intermediate negatives, wherein S2 is greater than 1 (e.g. 2, 3, 4 or more), P2 is less than P1, and with N2 being less than, the same as, or more than N1. In some embodiments, a region of "indefinite" status might exist where a number of spatially correlated positively classified locations is less than that required to provide a positive conclusion but more than that necessary to provide reasonable negative conclusion where a repetition of the test may be recommended. Similarly, a conclusion of a "faulty" test might be given if insufficient useable data is obtained to yield a positive, negative, or indefinite conclusion. In some embodiments, locations with unusable data may be considered directly or indirectly in algorithms used in defining whether sufficient proximity in the samples with positive classifications exists. For example, in some embodiments, unusable locations may count as a location with a partial negative classification (e.g. 1/8, 1/4, 1/2, even 2/3 of a location with a negative classification).

In embodiments where more nuanced classifications exist, other criteria for reaching a positive sample conclusion, or some other sample conclusion, may be defined and used. For example, a lower number of correlated spatially connected positive locations might be necessary to draw a positive sample conclusion than would be required if spatially connected locations were only moderately positive or had a mixture of positive, moderately positive, and indefinite classifications. In some embodiments, data may be processed in whole with associated results further analyzed to reach positive, negative, or other sample conclusions. In other embodiments, analysis may be performed and halted once a conclusion is reached (e.g., a biohazard signature present or positive conclusion has been reached) even if all the data for all locations has not been completely processed. For example, an analysis may begin based on arbitrary starting points (e.g., locations with positive classifications), and the analysis may be halted when a sufficient number of spatially correlated locations have been compared to reach a positive conclusion for the sample or a sufficient number of locations have been processed to rule out all but a single conclusion.

Parameters and methods utilized in the third level analysis (i.e., step 4 of FIG. 1A) may be selected and fine-tuned by performing repeated analyses with different methods and different parameters using samples having biohazard signatures that are known to exist and known not to exist and comparing the predictive results of the various methods and parameters against the known status of each such sample. Methods and parameters can then be implemented that provide reliable results that are within false positive and false negative target limits and that provide results within other constraints that may involve, for example, one or more of sample gathering time, testing and analysis time, operator skill availability, testing equipment cost, operational cost, and the like.

The method of FIG. 1A may be implemented by a variety of different systems according to various examples which are set forth hereafter and variations thereof which will be apparent to those of skill in the art upon review of the teachings herein. Generally, such systems may provide: (1) a means for implementing a first step of providing exposure and emission radiation data gathering for a plurality of different locations on a sample, that include using a narrow beam or broad exposure light source (e.g. a UV light source such as a laser or an LED) for providing excitation radiation to the sample, optical elements (e.g. apertures, quartz windows, mirrors, lenses, prisms, diffraction gratings, filters, or the like) for allowing emission radiation to reach, be focused on, and possibly to be of desired wavelength composition when it reaches a detector or different cells or regions of a detector (e.g. CCD arrays, photodiodes, photomultiplier tubes, and the like) to provide in parallel or in series band-by-band readings of emission radiation coming from each of the plurality of selected locations on the sample; (2) a means or subsystem for relatively moving the sample and an exposure location to provide for collection of such emission radiation, wherein the means for relatively moving may include, e.g. a stage for moving the sample, a stage for moving the optical elements, one or more scanning mirrors, a liquid flow channel and a pump, a moving aperture, and the like and may work in combination with actuators such as rotary or linear, electrical or pneumatic motors; (3) a controller, a programmed computer and memory, or hardwired electronic circuit elements to provide correlated operation of the various components and for storage of detected emission radiation data and associated location information; (4) a power source (e.g. a cord for connecting to a wall outlet, a battery, a fuel cell, or the like); (5) input means (e.g. a keyboard, a touchscreen, buttons, switches, a microphone, a camera, wired or wireless communication systems, and the like) and output means (e.g. a screen, printer, lights, speaker, wired or wireless communication systems, and the like); (6) means for comparing detected spectral radiation and background noise to remove or otherwise separate spectral data that is not sufficiently above background noise to allow useful analytic determination to be made wherein the removal may occur during or after data gathering where the means for comparing may include a programmed computer or hard wired electric circuit elements which may execute user defined algorithms or trained machine learning algorithms (which may or may not be running on the same computer system(s) or electronic components that provide for control and operation of the other systems components, that compare the magnitude of background noise with detected emission data information; (7) means for classifying spectral data coming from each of a plurality of different locations on a sample in different categories such as biohazard positive or negative status wherein such classification may be performed by a comparison of detected emission radiation from useful or usable locations to emission radiation associated with samples having known signature conclusions where the means for classifying may include a programmed computer and a memory or hardwired electronic circuit elements which implement a programmer defined comparison algorithm or implement an artificial intelligence algorithm or machine learning algorithm that has been subjected to training and which may or may not be running on the same computer(s) or electronic system components that provide for control and operation of the other systems components; and (8) means for performing a spatial analysis that compares the biohazard classified information from individual measurement locations to determine if a sufficient level of spatial clustering or proximity grouping of status readings having biohazard signature relevance exist so as to provide a biohazard signature presence conclusion and if not, then possibly determining whether sufficient data exists to confidently provide a biohazard signature not present conclusion or a biohazard indeterminate conclusion for the sample and thus a conclusion for the subject, location, or material of interest wherein the means for performing may include a programmed computer and a memory or hardwired electronic circuit elements which implement a programmer defined spatial analysis and conclusion algorithm or which implement an artificial intelligence algorithm or machine learning algorithm that has been subjected to training and which may or may not be running on the same computer(s) or electronic system components that provide for control and operation of the other systems components.

It is anticipated that some embodiments implementing the methods of FIG. 1A and its alternatives as well as some system embodiments implementing such methods may result in physical and operating parameters meeting some or all of the following conditions: (1) implementation in an analytical instrument having a volume less 500 liters, less than 50 liters, less than 20 liters, less than 10 liters, less than 5 liters, and/or less than 2 liters; (2) implementation in an analytical instrument having a mass of the housing and its contents (excluding a sample) being less than 50 Kg, less than 25 Kg, less than 10 Kg, less than 5 Kg, less than 3 Kg, and/or less than 2 Kg; (3) an analytical instrument with an average power consummation during use of less than 500 W, less than 200 W, less than 100 W, less than 50 W, and/or less than 20 W; and (4) a time period for exposing different portions of a sample a plurality of times to excitation radiation and analyzing detected emission data to reach a biohazard indicative conclusion of less than 20 minutes, less than 10 minutes, less than 5 minutes, less than 2 minutes, less than 1 minute, and/or less than 30 seconds.

In some embodiments implementing the method of FIG. 1A, a system may use optical elements that include, for example, one or more of: (a) one or more planar mirrors, (b) one or more focusing mirrors, (c) one or more lenses, (d) one or more diffraction gratings, (e) one or more prisms, (f) one or more low pass filters, (g) one or more band pass filters, (h) one or more high pass filters, (i) one or more dichroic filters, (j) one or more tunable filters, (k) one or more acousto-optic tunable filters, (l) one or more modulators (e.g., acousto-optic modulators), (m) one or more beam splitters, (n) one or more apertures, (o) one or more iris diaphragms, (p) one or more polarizers, (q) one or more fiber optics, (r) one or more UV opaque windows, (s) one or more UV transmitting windows, (t) one or more detectors, (u) one or more diffractive elements, and/or (v) one or more dispersive elements. In some embodiments, a signal detector may be used or a plurality of different detectors may be used where the detectors may include one or more of: (a) a CCD array, (b) a plurality of CCD arrays located along at least partially different detection paths, (c) a cooled CCD array, (d) a plurality of cooled CCD arrays located along at least partially different detection paths, (e) a photodiode, (f) an avalanche photodiode, (g) a plurality of photodiodes located along at least partially different detection paths, (h) a photo multiple tube (PMT), (i) a PMT array, and/or (j) a combination of any of (a)-(i).

In some embodiments, a system implementing the method of FIG. 1A may use a single detection path that is split into multiple paths by one or more wavelength splitting components. In other embodiments, a single detection path may be used with a rotating beam splitting element that serially directs, or one or more switchable filtering elements that serially pass, selected emission radiation of different bands onto a single sensor element. In some embodiments, the single detection path directs emission radiation onto at least one optical element that can be used to change wavelengths that reach a detector selected from the group consisting of: (a) one or more low pass filters, (b) one or more high pass filters, (c) one or more band pass filters, (d) one or more dichroic filters, (e) one or more tunable filters, (f) one or more acousto-optic tunable filters, (g) one or more diffraction gratings, (h) one or more prisms, (i) one or more diffractive elements, and/or (j) one or more dispersive elements.

In some embodiments, a system implementing the method of FIG. 1A may direct the emission radiation along a plurality of different detection paths, that include, for example: (a) a single path that is divided into multiple paths, (b) a single path that is divided into multiple paths by at least one dispersive element, (c) a single path that is divided into multiple paths by at least one non-dispersive element, (d) a single path that is divided by a series of non-dispersive elements to obtain a series of paths having different wavelengths, (e) a single path that is divided into multiple paths by at least one non-dispersive element wherein at least one of the multiple paths is divided into a plurality of additional paths by at least one dispersive element, (f) a single path that is divided into multiple paths by at least one non-dispersive element wherein a plurality of the multiple paths are each divided into a plurality of additional paths using a plurality of dispersive elements, (g) multiple paths for which at least one is divided into multiple additional paths, and (h) multiple paths for which a plurality is divided into multiple additional paths;

In some embodiments of the method of FIG. 1A, a system may include a housing that directly or indirectly holds a plurality of system components. For example, the housing may hold directly or indirectly (i.e. supported by at least one intermediate component that the housing holds), at least one of the optical elements exemplified above. In some embodiments, the housing may directly or indirectly support an output communication device that includes, for example, one or more of: (a) a port for receiving a cable, (b) a proximal end of a cable, (c) a wireless transmitter, (d) a display, (e) a light source, and/or (f) a sound source wherein the communication device provides for a function selected from the group consisting of: (a) transmitting data to an external processing system for manipulating the data, and/or (b) providing test result conclusions. In some embodiments, the housing may directly or indirectly support an input device that includes, for example, one or more of: (a) a port for receiving a cable, (b) a proximal end of a cable, (c) a wireless receiver, (d) a touch screen, (e) a key pad, (f) at least one button, (g) a least one switch, and/or (h) a microphone for receiving audio input wherein the input device provides for a function selected from the group consisting of: (a) receiving operator input, (b) receiving data, (c) receiving program updates, and/or (d) receiving operational commands from an external device. In some embodiments the housing may directly or indirectly hold or support a power source for operating components held within the housing, wherein the power source may include, for example, one or both of at least one battery and/or a fuel cell. In some embodiments, the housing may hold, directly or indirectly an input port for receiving external power for operating components within the housing. In some embodiments, the housing may hold, directly or indirectly, a programmed processor for controlling the excitation radiation source, the relative moving of the beam of excitation radiation and the sample, the at least one detector; and/or a memory for storing emission radiation detection signals and associated positioning information. In some embodiments, the housing may hold, directly or indirectly, at least one programmed processor and at least one memory for providing one or more functions such as, for example: (a) controlling the excitation radiation source, (b) controlling the relative movement of the beam of excitation radiation and the sample, (c) controlling the at least one detector, (d) storing predetermined biohazard indicative signal information, (e) storing predetermined non-biohazard indicative signal information, (f) storing background signal information, (g) storing emission detection signals and associated positioning information, (h) processing information to produce useful detection signal information, (i) processing information to produce a plurality of biohazard indicative statuses, and/or (j) processing information to produce a biohazard indicative conclusion. In some embodiments, the housing may, directly or indirectly, hold at least one additional mechanism including, for example: (a) a mechanism for disposing of a sample substrate after analyzing the sample, (b) a cleaning system for dispensing a cleaning solution (e.g. via spraying, jetting, or wiping) onto a surface to be cleaned, and for removing the cleaning solution (e.g. via rinsing, blowing, heating, or wiping), (c) a sterilization system for removing or deactivating biohazards (e.g. via UV exposure, ozone exposure, spraying a sanitizer, autoclaving), and/or (d) a mechanism for receiving, holding, and releasing a sealed sample.

In some embodiments, the housing may hold, directly in directly, an imaging camera that is configured to provide images of a sample that may include, for example, one or more of: (a) an image from visible reflected radiation, (b) an image from transmitted visible radiation, (c) an image from visible radiation created by excitation, (d) an image from selected visible reflected radiation, (e) an image from selected transmitted visible radiation, (f) an image from selected visible radiation created by excitation, (g) an image from UV reflected radiation, (h) an image from transmitted UV radiation, (i) an image from UV radiation created by excitation, (j) an image from selected UV reflected radiation, (k) an image from selected transmitted UV radiation, (l) an image from selected UV radiation created by excitation, (m) an image from IR reflected radiation, (n) an image from transmitted IR radiation, (o) an image from IR radiation created by excitation, (p) an image from selected IR reflected radiation, (q) an image from selected transmitted IR radiation, (r) an image from selected NIR radiation created by excitation, (s) an image from NIR reflected radiation, (t) an image from transmitted NIR radiation, (u) an image from NIR radiation created by excitation, (v) an image from selected NIR reflected radiation, and/or (w) an image from selected transmitted NIR radiation. In some embodiments, the housing may also directly or indirectly support a display for visually viewing the provided image or images while in other embodiments, a communication system may be used to transmit the image for display by a separate device. In some embodiments, the housing may hold a separate light source for visibly illuminating the sample location. In some embodiments, the imaging system may also provide for overlaid imagery to allow visualizing of an actual or intended exposure location on a sample (e.g., crosshair positioning on a display screen or a light spot on a display screen) possible to aid in setting a starting exposure location.

FIG. 1B provides a block diagram of a method of establishing baseline spectroscopic data for in situ or in vitro samples from a subject, location, or material that are known to contain a biohazard signature of interest and for samples known not to contain the biohazard signature of interest wherein such baseline spectroscopic data may be useful in implementing various embodiments of the invention involving the categorization of samples for which a biohazard signature determination is to be made. The process of FIG. 1B includes four primary steps.

Step 1 provides for testing a plurality of different samples using one or more testing methods of acceptable reliability which are used to determine whether a biohazard signature of interest is present. Such tests may include, for example, the use of PCR or RT-PCR. The samples may be grouped by different attributes including subject characteristics, collection location attributes, collection method attributes, sample storage methods, and the like. Examples of such attributes include animal source (e.g. human, other animal, or specific type of other animal), plant type source, material sources, fresh samples vs different types of stored or treated samples, samples gathered by similar methods, sources having similar gender, sources having similar age, sources have similar blood type, samples extracted from similar body regions or secretions, and sources or samples having different common traits. Such attributes may be evaluated for relevance and, if necessary, taken into consideration when applying specific baseline data to specific samples that are to be analyzed.

Step 2 provides for the exposing of a plurality of locations of each sample to excitation radiation and reading emission radiation coming from each such location in a plurality of different wavelength bands. Such emission spectrums may be read, for example, in relative power vs. wavelength, or signal strength vs. wavelength). Corrective factors may be used to adjust the relative power or signal strengths when known differences in power loss occur in the optical path for each wavelength band or detector sensitivity varies. Such corrective factors may bring the readings to values corresponding to an absolute standard or to a relative standard. Though excitation radiation may be provided in a form that is different from that used in the process of FIG. 1A, it is preferred that the excitation radiation used in the process of FIG. 1B be of the same form as that which will be used when obtaining spectroscopic data for samples for which a biohazard signature determination is to be made. Similarly, though it is possible that different excitation radiation exposure parameters be used in the process of FIG. 1B as compared to those used in the process of FIG. 1A and different emission radiation collection and processing methods be used in FIG. 1B as opposed to those used in FIG. 1A, it is preferred that such exposure parameters and collection methods be similar to those that will be used in obtaining data from samples for which a biohazard signature determination is to be made. The gathered information may be normalized, processed to yield band-to-band ratio information, or processed in some other manner to allow direct or indirect comparison to data from other locations or to data from samples to be tested for biohazard signature inference.

Step 3 calls for the separation of the samples into two or more groups, e.g., biohazard signature positive and biohazard signature negative. The two original groups may be further divided into two or more groups, for example, a group for algorithm training (or calibration) and a group for testing or trained algorithm verification. Further divisions are also possible based on other common factors or different factors associated with the data such as those noted in the discussion of step 2 above.

Step 4 calls for using the data from the separated sample groups, or using such data after further processing or clean up, as a basis for comparison and classification of spectrum data taken from samples for which a biohazard signature classification is to be determined such as discussed above with regard to step 3 of FIG. 1A (e.g. using a supervised classification algorithm and/or an unsupervised classification algorithms such as PCA (Principal Component Analysis and its derivatives) or KNN (K-Nearest Neighbors)) or one or more other correlation methods involving a comparison of data gathered from a sample to be classified and data associated with samples having positive biohazard signature statuses and negative biohazard signature statuses. If necessary, prior to using the separated data for correlation purposes, it may be used for training and testing algorithms to verify algorithm reliability against false negatives and/or false positives within a desired error tolerance. In some embodiments, a balance may be struck between level of false positives, level of false negatives, and level of indeterminate testing results with a hope of minimizing each but at least bringing each into an acceptable range.

In variations of the processes of FIGS. 1A and 1B, different processing orders may be used, some of which may reverse the orders of some of the illustrated steps or provide for parallel processing of certain steps for one sample or for one location while different steps for different samples or different locations are being processed. In still other variations, additional processing steps may be included and/or some steps may take on a modified form.

FIG. 2A provides a flowchart of a spectroscopic method for determining whether a biohazard signature is present in a sample according to a second embodiment of the invention. As with FIGS. 1A and 1B, alternative embodiments exist which may add in additional steps, may remove or modify some steps, may change the order of operation of some steps and/or provided parallel processing of some steps.

The process of FIG. 2A begins with Block A and then moves to Block B which calls for associating a value of "r" to each of a plurality of measurement locations on the sample where "r" ranges from 1 to R wherein exposure and measurement will occur for a first location r=1, then for a second location r=2, and so on until a final measurement is made at the location where r=R. The value R may range from tens to hundreds to even thousands. For example, R may be initially set to a number greater than 10, greater than 50, greater than 100, greater than 200, greater than 400, or even greater than 800. Next, in Block C, "r" is set to a value of one, r=1, and then in Block D, an inquiry is made as to whether the sample is (or samples are) to be read in situ as opposed to being extracted and then read. If the answer is "yes", the process jumps to Block F whereas if the answer is "no", the process moves forward to Block E. In Block E, a sample is (or samples are) gathered. From Block E, the process moves to Block F wherein the sample is positioned for reading a location corresponding to the value of "r". If the process moved directly from Block D to Block F, the relative positioning of the sample would involve locating the exposure and detection elements, and possibly other elements, in proximity to the sample location that is to be measured (e.g., in proximity to a particular location on or in the body of the subject, on or in an environmental location, at a location in a facility, or on or in a machine where the sample is to be read).

After positioning the sample, the process moves to Block G which calls for a relatively small portion of the sample at location "r" to be subjected to excitation radiation (e.g. deep UV radiation). In some alternative embodiments, the location of exposure may be a large portion of the sample, or even the entire sample, if steps are taken to ensure that emission radiation reaching a particular detector is limited to emission radiation coming from the region around position "r".

During the exposure of Block G or perhaps slightly after the exposure, Block H is initiated and the emission spectrum information coming from location "r" is read such that radiation is detected in a plurality of bands or channels. The number of bands or channels may range from under ten to over two thousand and may be different depending on the particular biohazard signature being looked for, the anticipated complexity of the sample, the type of emission radiation being detected, and other assumptions made, or complexities anticipated. In some embodiments, the number of wavelength bands may be at least four, at least eight, at least fifteen, at least thirty, at least sixty, at least 120, at least 250, at least 500, at least 1000, or even at least 2000. The number of bands used and the width of each band may be selectable in a given instrument or it may be fixed within the design of the instrument (i.e. the physical design, a programmed design, or by a trained AI algorithm).

In some embodiments, emission radiation is limited to native fluorescence radiation while in other embodiments, other emission radiation may be used. In still other embodiments, multiple types of emission radiation may be detected simultaneously, for a given location, or in series. For example, in some embodiments, fluorescence may be used for initial data gathering because of the speed of generation and detection, which may be followed by Raman emission radiation detection for particular locations where the fluorescence emission radiation yielded a result that made finer, but slower, analysis relevant. Such a second stage detection may occur immediately, for a given location "r". Alternatively, it may occur after multiple locations have undergone first stage detection, or even all locations have undergone first stage detection. In still other embodiments, additional stages of detection may occur using additional types of emission radiation (e.g. phosphorescence or Rayleigh scattering). In some embodiments, second or subsequent stage detection may occur using the same type of emission radiation as the initial stage with detection occurring at locations intermediate to the initial measurement locations or using different excitation radiation or different detection bands.

In some embodiments, the number of the wavelength bands, the width of individual wavelength bands, continuous wavelength range of the bands, and/or a discontinuous set of the wavelength regions may be selected for a single type of emission radiation or for multiple types of emission radiation such as, for example: (1) native fluorescence, (2) Raman, (3) phosphorescence, and (4) Rayleigh scattering. In different embodiments, detected emission radiation, for example, may range from (a) greater than 250 nm, (b) greater than 275 nm, (c) greater than 300 nm, (d) less than 600 nm, (e) less than 500 nm, (f) less than 400 nm, (g) less than 380 nm, (h) within the range of 250 to 600 nm, (i) within the range of 270 to 600 nm, (j) within the range of 280 to 600 nm, (k) within the range of 280 to 550 nm, or (l) within the range of 300 to 500 nm. In other embodiments, other wavelengths of emission radiation may be detected and individual wavelength bands may or may not have the same widths.

The timing of emission radiation detection may be different in different embodiments or may vary within a single embodiment if multiple detections will occur. For example, the timing of detection may occur (a) during exposure but greater than 1 µs (microsecond) after the initiation of excitation radiation, (b) during exposure but greater than 5 µs after initiation of the excitation radiation, (c) during exposure but greater than 10 µs after initiation of the excitation radiation, (d) during exposure but greater than 20 µs after initiation of the excitation radiation, (e) greater than 100 µs after initiation, (f) greater than 1 ms (millisecond) after initiation of excitation radiation, (g) greater than 10 ms after initiation of excitation radiation, (h) greater than 1 µs (microsecond) after the extinction of excitation radiation, (i) greater than 5 µs after the extinction of excitation radiation, (j) greater than 10 µs after the extinction of excitation radiation, (k) greater than 20 µs after the extinction of excitation radiation, (l) greater than 100 µs after extinction of excitation radiation, (m) greater than 1 ms after extinction of the excitation radiation, (n) at a set time after initiation of the excitation radiation, (o) at a plurality of different set times after initiation of the excitation radiation, e.g. to provide a buildup profile, (p) at a set time after extinction of the excitation radiation, or (q) at a plurality of set times after extinction of the excitation radiation, e.g. to provide a radiation decay profile.

After measurement, detected emission radiation for each location is compared to background noise, as set forth in Block I, so that a determination can be made for each location as to whether or not the measured data exceeds background by a sufficient amount to provide useful data for analysis. It is anticipated that measured data that is too close to background noise will not provide useful signals and will lead to identification conclusions having higher rates of false positives and/or false negatives. Different metrics for sufficient differences are possible. For example, in some embodiments, the determination may require measured data to exceed background noise by a factor that is a multiple of the background, e.g. MD>=N*BD, where MD is the magnitude of the measured data, N is a factor greater than 1, and BD is the magnitude of the background noise. In some embodiments, N may be as small as 2 or 3 or less while in other embodiments, N may be set at a higher value, e.g. 4, 5, 7, 10 or more. For locations where MD does not meet the requirement, the locations may be ignored in the data analysis or the missing data may be accounted for when performing the spatial processing of Block M. For example, in some embodiments, for proximity determination, the unusable data locations may simply be treated as locations with negative classifications while in others, they may be treated in a different manner. If too many locations have insufficient MD, in some embodiments, the sample may be rejected as indeterminate, and a new sample may be required. For example, in some embodiments, the number of useful signal groups required to provide a determinate biohazard indicative status may be as small as 5% of the measured locations while in others, more than 10%, more than 20%, or even 40% may be required. Still others may require something greater than 60% or even 80%. Others may require different amounts or different criteria for determining the amounts. A smaller number may be required if a positive (i.e. biohazard signature present) conclusion can be reached while a larger number may be required to draw a determinate negative conclusion. In still other embodiments, a proximity requirement for useful signal groups may be mandatory or preferred.

After Block I is completed, the process moves to Block J which calls for the locations with sufficient MD to have their spectral results compared to spectral results associated with samples of known biohazard signature status for the purpose of producing a preliminary classification concerning the possibility of biohazard presence at each such location. Such comparisons and associated determinations may be performed through preset algorithms or through artificial intelligence based, or machine learning enhanced, algorithmic training and processing. The resulting preliminary conclusions, or classifications, may be binary in nature, e.g., positive presence or negative presence for each location; they may be trinary in nature, e.g. positive presence, negative presence, or indeterminate presence for each location; or they may be of a higher order output. For example, in some embodiments, the preliminary conclusion or classification applied to each location may be one of seven or more classifications: (1) a positive indication of a biohazard signature of interest (BSOI), (2) a negative indication of BSOI, (3) an indeterminate indication of BSOI, (4) a strong positive indication of BSOI, (5) a weak positive indication of BSOI, (6) a weak negative indication of BSOI presence, (7) a strong negative indication of BSOI presence, or (8) no conclusion with regard to BSOI presence. In some variations, even locations with insufficient MD may be allocated a preliminary conclusion that may be used in subsequent processing.

In some variations of the process of FIG. 2A, instead of performing the process of Blocks G-J as set forth in the flowchart (i.e. the reading of an individual location followed by determination of usability and then comparison and classification performed for that location after which a next location is read, usability is determined, and then comparison and classification performed and so on until all locations are read, determined, compared and classified). Blocks G-J may be performed in a full group approach (i.e. all locations may be read under Blocks G and H, then all locations may be reviewed under Block I to determine usability, and then all locations may undergo the comparison and classification of Block J). In other embodiments, other intermediate approaches between the whole group approach and the individual location approach may be implemented. In still other variations, the individual location approach may include one or more additional decision branches that insert additional steps when certain conditions are met. For example, after reading a location, after performing a usability analysis, or after performing a comparison and possibly reaching a preliminary classification conclusion for the location, a triggering condition may be recognized that calls for performing additional spectroscopy data gathering on the location before moving to a next measurement location. If a decision is made to perform additional spectroscopic data gathering, the method may immediately initiate an additional exposure of the location, or exposure of a nearby location, using the same or different excitation radiation, where detected emission radiation may be of the same type as initially obtained (e.g., native fluorescence) or may be of a different type (Raman, phosphorescence, or Rayleigh). In still other embodiments, a determination for a need to gather more spectroscopic data from a given location may be made immediately but initiation of additional data gathering may be delayed until all preliminary data gathering for each preplanned location has been completed, or determination of a need for further spectroscopic data gathering for a given location may be delayed until all preliminary data gathering for each preplanned location has been completed.

From Block J, the process of FIG. 2A moves forward to Block K where the value of "r" is incremented by 1, i.e., r=r+1. From Block K, the process moves to Block L where an inquiry is made as to whether the value "r" has exceeded "R", and if so, the process moves forward to Block M, and if not, the process loops back to Block F so that at least one additional location may undergo examination (i.e. exposure, emission radiation production and detection and preliminary analysis).

In the process of FIG. 2A, after Block L, the process moves to Block M which provides a next, and perhaps final, processing step. In Block M, the preliminary conclusion of Block J for each location is further processed to determine whether a sufficient number of nearby locations have positive, or relatively positive, preliminary conclusions of biohazard signature presence. It is believed positive biohazard indicators in a sample with a true biohazard signature presence are likely be located in proximity to one another as opposed to being thinly spread throughout a sample. The spatial analysis may take on a variety of forms that may require, for example, (1) a minimum number of consecutive readings showing preliminary biohazard conclusions or classifications, and/or (2) a certain number, or ratio, of N consecutive readings to have positive biohazard preliminary conclusions or classifications. The spatial processing of information may occur for only a portion of the plurality of locations "r" if a conclusion of positive presence is found prior to processing all of the locations. In this step, the preliminary biohazard conclusions for individual locations are converted to a biohazard conclusion for the sample as a whole. Such biohazard conclusions may be of binary, trinary, or higher order nature. Such conclusions may be indicative of, for example: (1) positive for the BSOI, (2) negative for the BSOI, (3) indeterminate for the BSOI, (4) strongly positive for the BSOI, (5) weakly positive for the BSOI, (6) weakly negative for the BSOI, or (7) strongly negative for the BSOI.

In the embodiment of FIG. 2A, after completion of Block M, the process moves forward to Block N where the process ends.

In addition to the variations discussed above, numerous additional variations of the process are possible. Some such variations may involve the insertion of one or more additional steps before, between, or after those explicitly set forth in FIG. 2A, some may involve the reordering of some steps, some may involve the combining of separate steps or the splitting of steps into substeps, and/or some may involve the use of alternative steps that yield similar results in different ways. Some variations may involve inclusions of one or more additional levels of analysis prior to reaching a final biohazard signature conclusion. In still other alternative embodiments, a maximum number of data gathering locations may be set, but the data gathering may be terminated prior to exposing and reading all locations by performing the analyses of Blocks J and M as locations are read such that if a definitive conclusion is reached prior to reading all locations, the process may terminate such that the system may provide a timelier result or such that the system may begin processing another sample.

FIG. 2B1 provides an example method for identifying the usefulness of spectral information for each of a plurality of sample measurement locations as may be used in Block I of FIG. 2A or more specifically as part of a full group approach to processing the data. The process of FIG. 2B1 starts with Block A and then moves to Block B which calls for setting a location number n equal to 1 and setting a total number of locations to consider equal to a value N which corresponds to the total number of locations from which spectroscopic data was gathered. From Block B, the process moves to Block C which calls for providing the measured spectroscopic data or information for the nth location that was obtained in the operation of Blocks G and H of FIG. 2A.

From Block C, the process moves to Block D which calls for providing criteria against which the measured spectral information can be compared, judged, or classified as being useful or usable information as opposed to not being useful or being unusable. In other embodiments, the criteria may enable a more nuanced judgement concerning usefulness or lack thereof. In Block E, comparison of the measured information from location "n" is made against the judging criteria of Block D to provide a binary labeling or categorization of the information from location "n". In some variations, the judgement or comparison may result in different binary classification or categorization while in others, the judgement may yield a more nuanced classification concerning a level of usefulness. In some embodiments, the criteria may involve an estimate or expectation of certain required signal strength for at least some wavelength bands and a comparison or analysis to ensure that the signal strength level is met. In other embodiments, criteria may involve a certain level of measurement differential between selected wavelength bands. In other embodiments, the signal strength might need to exceed an anticipated or detected electronic noise level in the detection system wherein the required differential is a set amount while in others, it may be a multiple of the anticipated or detected electronic noise level where the multiple is an amount greater than one and most preferably an amount that strikes an acceptable balance between false negatives and/or false positives in comparison to the percentage of samples or location readings that must be rejected as lacking sufficient usefulness. In some embodiments, anticipated noise level may be substantially constant across all wavelength bands (e.g., within 2%, within 5%, within 10%, or within 20%) or it may vary based on groups of wavelength bands, or even be band-to-band specific.

From Block E, the process moves forward to Block F where the inquiry is made as to whether the information was determined to be useful or not in Block E. If useful, the process moves forward to Block G, but if unusable, the process skips Block G and moves forward to Block H. At Block G, the flag for location "n" is set to "useful". After Block G, in the event Block G was not skipped, the process moves forward to Block H, wherein "n" is incremented by 1, i.e., "n=n+1". From Block H, the process moves forward to Block I which calls for a determination of whether "n" is greater than "N", i.e. "n>N?". If not, the process loops back to Block C, and if yes, the process moves to Block J and ends. When the process is completed, all locations "n" will be effectively and properly labeled as "useful" or "unusable". In alternative embodiments, different labeling and/or inquiries may have been made and performed to yield a similar or more nuanced result. For example, in some alternatives, only "unusable" locations may be labeled while in others, both "useful" and "unusable" may be labeled, and in still others, labeling may be replaced with a deletion of data associated with "unusable" locations.

FIG. 2B2 provides a second example method for identifying the usefulness of spectral information for each of a plurality of sample measurement locations as may be used in Block I of FIG. 2A or more specifically as part of a full group approach to processing the data wherein the method may utilize a predefined criteria or may use a criteria that is fixed by an algorithm training process that helps provide optimized biohazard signature conclusions and wherein the method may use a wavelength-band-by-wavelength-band comparison of measured spectral data to background information where the measured data for a minimum number of bands exceeds background information data by a desired factor where X may be predetermined or defined during a training process.

The process of FIG. 2B2 is similar to that of FIG. 2B1 with the primary difference being the insertion of an additional Block D that calls for the providing of background spectral information for the measurement system which can be compared to the measured data for each location "n", and the associated incrementing of Blocks D-J of FIG. 2B1 to Blocks E-K of FIG. 2B2 along with specific modification to Block E of FIG. 2B2.

Block E of FIG. 2B2 specifically calls for providing background spectral information as part of a criteria against which the measured spectral information can be compared, judged, or classified in determining if the measured spectral information of Block C can be considered useful or must be considered unusable. The criteria may be applied in a global manner or on a wavelength-band-by-wavelength-band basis using the measured information and the supplied background spectral information to provide a binary labeling or categorization of the information from location "n". In some embodiments, the criteria may involve a certain level of compared differential between the measured and background spectral information. In other embodiments, the measured signal strength at a location "n" for one or more wavelength bands may need to exceed an electronic noise level included in the provided background spectral information by a specific amount while in others, it may be a multiple of such electronic noise level where the multiple is an amount greater than one and most preferably an amount that strikes an acceptable balance between false negatives and/or false positives in comparison to the percentage of samples or location readings that must be rejected as lacking sufficient usefulness. In some embodiments, anticipated noise level may be substantially the same across all wavelength bands (e.g., within 2%, within 5%, within 10%, or within 20%) or it may vary based on groups of wavelength bands, or even be band-to-band specific.

From Block E, the process moves to Blocks F-K of FIG. 2B2 in a manner analogous to that noted for Blocks E-J of FIG. 2B1.

FIG. 2C1 provides a block diagram illustrating two different general forms that predetermined signature/signal information may take. In the first example, illustrated in Block A, the information is provided on a wavelength-band-by-wavelength-band basis using raw or normalized data and from a plurality of locations from each of a plurality of different samples that are flagged with predetermined signature conclusions and possibly supplemental sample source information. The information from samples with known biohazard signatures of interest may be used as part of a basis for concluding that a measured sample location with similar information is also indicative of biohazard signature presence as is to be performed in Block J of FIG. 2A or by the example process of FIG. 2D1. The information from samples known to lack a biohazard signature of interest may be used as part of a basis for concluding that a measured sample location with similar information is also indicative of no biohazard signature presence. A comparison of a measured spectrum against the predetermined sample can be used to yield a preliminary classification but alone is likely to be insufficient to yield a positive or negative conclusion for a sample as whole. In the second example, illustrated in Block B, the information is provided on a wavelength-band-by-wavelength-band selected ratio basis using raw or normalized data from a plurality of locations from each of a plurality of different samples that are flagged with predetermined signature conclusions and possibly supplemental sample source information. Like the data in Block A, the data in Block B may be used in the process of determining a classification status for specific useful sample locations. In other variations, the predetermined signature/signal information may be provided in other forms or in additional forms, some examples of which are provided in FIG. 2C2.

FIG. 2C2 provides a block diagram of a six different more detailed example forms A.-F. that the predetermined information may take along with eight different variations of information that may be included in form C. and five different variations that may be included in form F. Numerous other forms and variation examples are possible and will be apparent to those of skill in the art upon review of the teachings herein.

Figure 3:
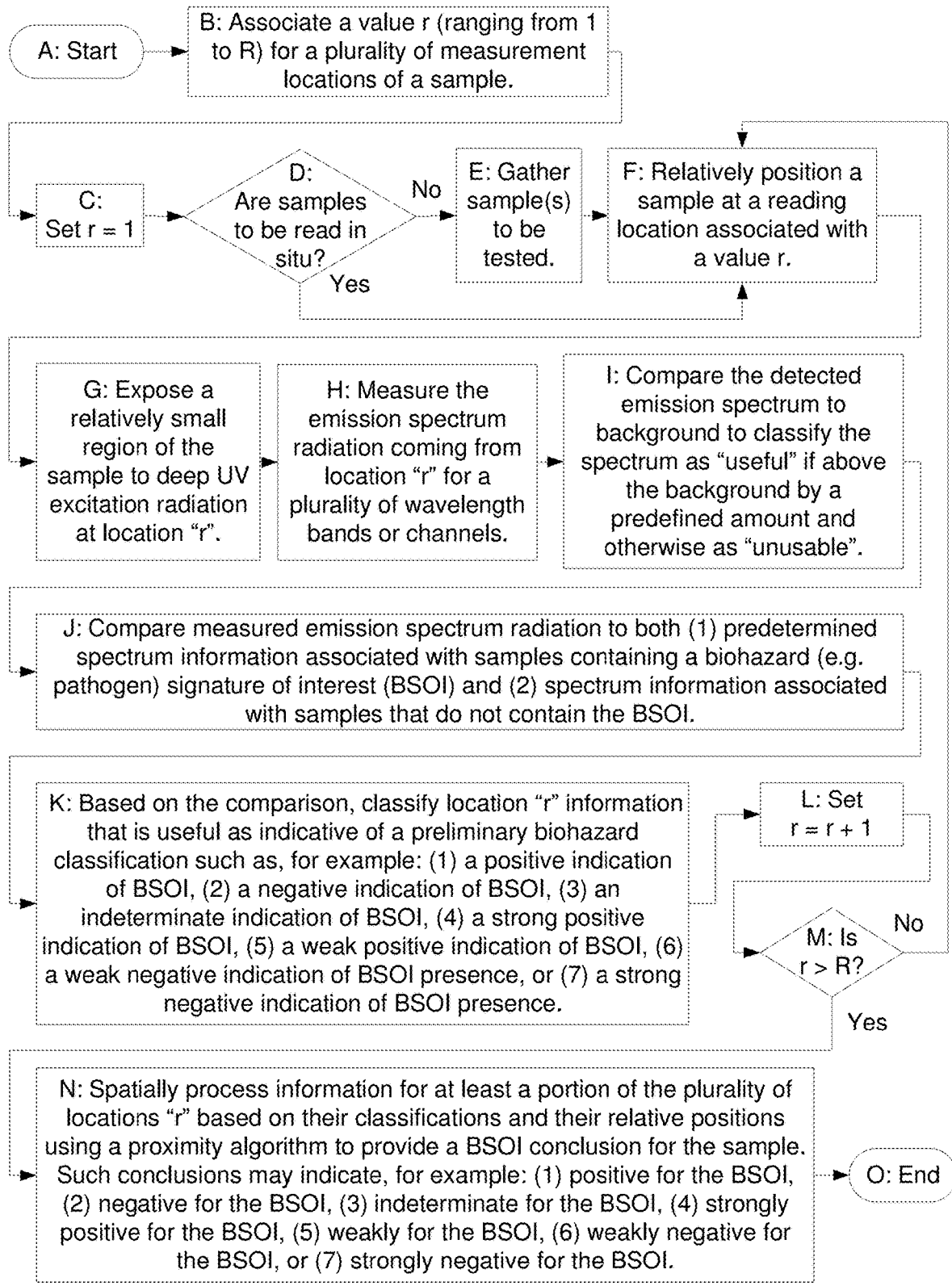

FIG. 2C3 provides a block diagram of a number of examples, A-H, of supplemental sample information that may accompany samples and even predetermined signature/signal information that may be used in enhancing, or fine tuning, conclusions that are reached by the method of FIG. 2A.

Figure 4:
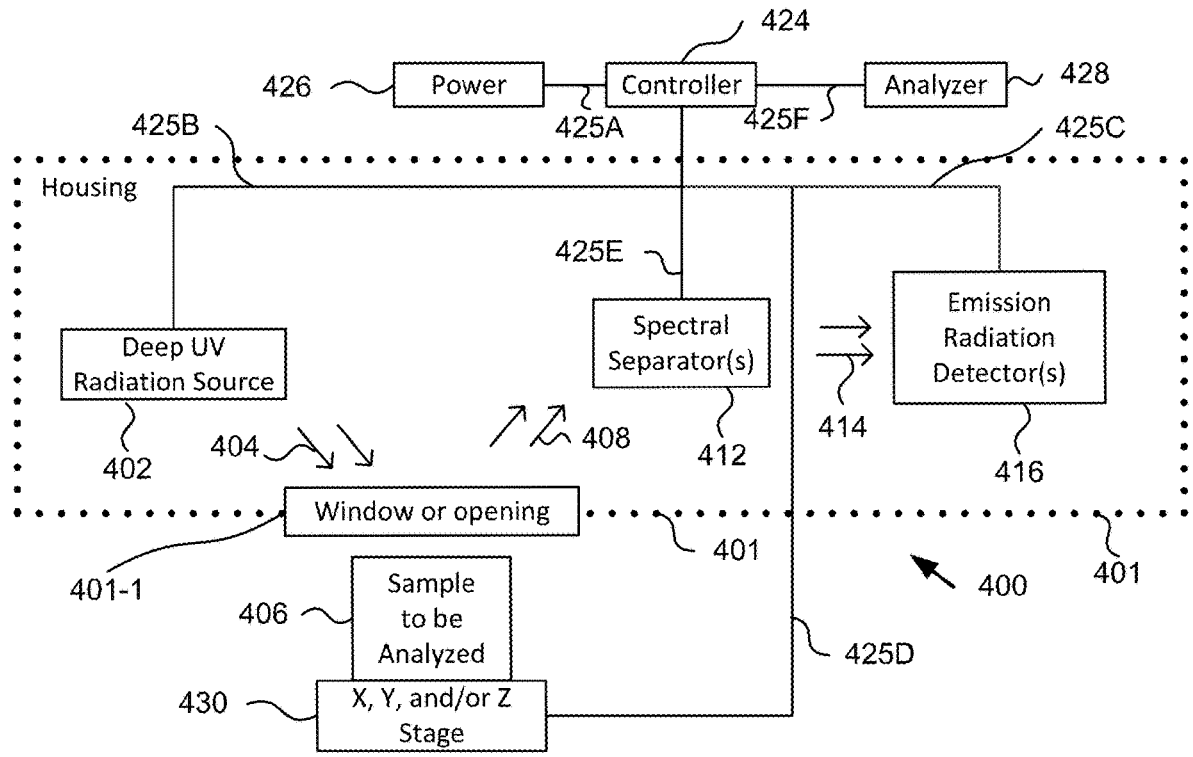

FIG. 2C4 provides a block diagram of four example signature conclusions that may accompany predetermined signature/signal samples, similar categories may also be used for classifying measured samples after comparison to the predetermined information. In other embodiments or variations, different, fewer, or additional conclusions may accompany the predetermined information.

FIG. 2D1 provides a flowchart of an example process that may be used in implementing Block J of FIG. 2A or more specifically as part of a full group approach to processing the data to provide a location-by-location classification or preliminary conclusion about potential biohazard signature presence for each such location but not for a sample as a whole. The process of FIG. 2D1 begins with Block A and then moves to Block B which sets a useful location number variable, u, to a value of 1, i.e., u=1, and sets a total number of useful locations (e.g., as determined by Block I of FIG. 2A) to a value of U. From Block B, the process moves to Block C which calls for providing the spectral information for location u while Block D calls for the direct or indirect providing of predetermined spectral information for a plurality of samples that are known to have one or more selected biohazard signatures as well as from samples known not to have the biohazard signatures. From Block D, the process moves forward to Block E which calls for the comparison of the measured spectral data (from a location on the sample whose biohazard signature classification is to be determined) to the data from the samples known to have biohazard signatures and those known not to have biohazard signatures to provide a classification, or preliminary biohazard indicative status, of a location "u" of the sample. From Block E, the process moves to Block F which records the status or classification derived from Block E after which the process moves to Block G which increments the location number by 1, i.e., sets u=u+1. After the incrementing of Block G, the process moves to the inquiry of decision Block H which asks whether location u is greater than U, i.e. u>U?. If the answer is no, the process loops back to Block C and begins the analysis for a next location, whereas if the answer was yes, the process moves to Block I and ends.

FIG. 2D2 provides a block diagram of the four example biohazard signature classifications that may be applied to each location. The indicated classifications include: (A) the data for a location is indicative of the presence of the biohazard signature of interest, (B) the data for a location is indicative of the absence of the biohazard signature of interest, (C) the data for a location is indeterminate as to whether a biohazard signature of interest is present (which may result from data being inadequate to complete processing or the data though processed properly does not yield a result that sufficiently favors an (A) or (B) classification), and (D) the data is provided with a classification that shows a weighting or possibly a probabilistic indication for biohazard signature status. In other variations, other classifications may be used.

FIG. 2D3 provides a block diagram setting forth seven example processes that may be used in implementing the comparison and classification called for in Block E of FIG. 2D1.

In Block A (Example 1), for each of at least a selected plurality of the bands for each measurement location on a sample, the process includes comparing the measured spectral information to that of the predetermined samples having known biohazard signatures statuses determining if the spectral information of the measured sample is generally closer to that of the samples having biohazard present conclusions or those with known non-biohazard present conclusions and labeling the respective bands with a corresponding biohazard status and then combining the corresponding biohazard statuses for each selected band b to provide a biohazard indicative status or classification for the specific location (i.e. group of bands associated with location u).

In Block B (Example 2), a process similar to that of Example 1 is implemented but using a calculated ratio of spectral information associated with each selected band b and another band from the measured sample that is compared to corresponding ratios associated with the predetermined samples having known biohazard present conclusions and known non-biohazard present conclusions, determining if the ratio of the measured sample is generally closer to that of the samples with known biohazard present conclusions or the samples with known non-biohazard present conclusions, labeling the band b with a corresponding biohazard status, repeating for all selected bands, and then combining the corresponding biohazard statuses for each selected band associated with a location to provide a biohazard indicative status, or classification, for that location.

In the process of Block C (Example 3), a process similar to that of Example 1 or 2 may be used but with a higher order comparison (i.e., a comparison that looks at more than a biohazard signature presence or non-presence from the samples with known biohazard signature conclusions). In such higher order comparisons, the comparisons may be made in a single level with resulting classifications reached or they may occur in staged levels with each level confirming, modifying, or fine tuning the preliminary findings associated with the prior levels. In such higher order comparisons, the predetermined samples may have more than two categories or attributes identified, e.g. they may not only have positive or negative biohazard identifications, they may also have alternative designations, such as biohazard signature rankings or strengths; they may also have other attributes, for example, associated with one or more of: the subjects from which they were gathered; the method of gathering, the body location from which the sample was taken, the facility, the time and date of gathering, and the like. In other such higher order comparisons, the conclusions reached may yield more than two classification results.

In the process of Block D (Example 4), features and data processing associated with Examples 1-3 may be used, but in addition, they use a selected artificial intelligence or machine learning algorithm for at least part of the analysis based in part on information from the samples having known biohazard statuses and possibly other attributes. The information from the samples that have known biohazard statuses may be used, at least in part, as training data and verification data such that when the measured data associated with specific locations from unknown samples is processed, the trained algorithm produces results that are consistent with the training data and meet or exceed requirements allowed for false positives, false negatives, and sensitivity. In such embodiments, the artificial intelligence (AI) or machine learning (ML) algorithms are preferably of the supervised type with respect to training samples being labeled with biohazard signature conclusions obtained from other methods. In other implementations, the AI or ML algorithms may be supervised with regard to other attributes or may be unsupervised with regard to the other attributes.

In the process of Block E (Example 5), a method similar to that of Example 4 is used but wherein the AI or ML algorithm specifically includes an instance-based artificial intelligence algorithm such as, for example: a K Nearest Neighbor (KNN) algorithm, a Learning Vector Quantization (LVQ) algorithm, a Self-Organizing Map (SOM) algorithm, a Locally Weighted Learning (LWL) algorithm, or a Support Vector Machines (SVM) algorithm.

In the process of Block F (Example 6), a method similar to that of Example 4 is used but wherein the AI or ML algorithm specifically includes a dimensionality reduction algorithm such as, for example: a Principal Component Analysis (PCA), a Principal Component Regression (PCR), a Partial Least Squares Regression (PLSR), or a Discriminant Analysis (DA).

In the process of Block G (Example 7), a method similar to that of Example 4 is used but wherein the AI or ML algorithm specifically includes a regression analysis such as, for example: an Ordinary Least Squares Regression (OLSR) analysis, a Linear Regression analysis, a Logistic Regression analysis, a Stepwise Regression analysis, a Multivariate Adaptive Regression Splines (MARS) analysis, or a Locally Estimated Scatterplot Smoothing (LOESS) analysis.

Additional alternative embodiments are possible for implementing the comparison and classification called for in Block E of FIG. 2D1 with some such additional embodiments including combinations of the features selected from the above seven alternatives or using such methods in a stacked manner to provide enhanced conclusions (e.g., conclusions with lower false positive and/or false negative errors), improved sensitivity, or more nuanced conclusions.

Figure 2E:
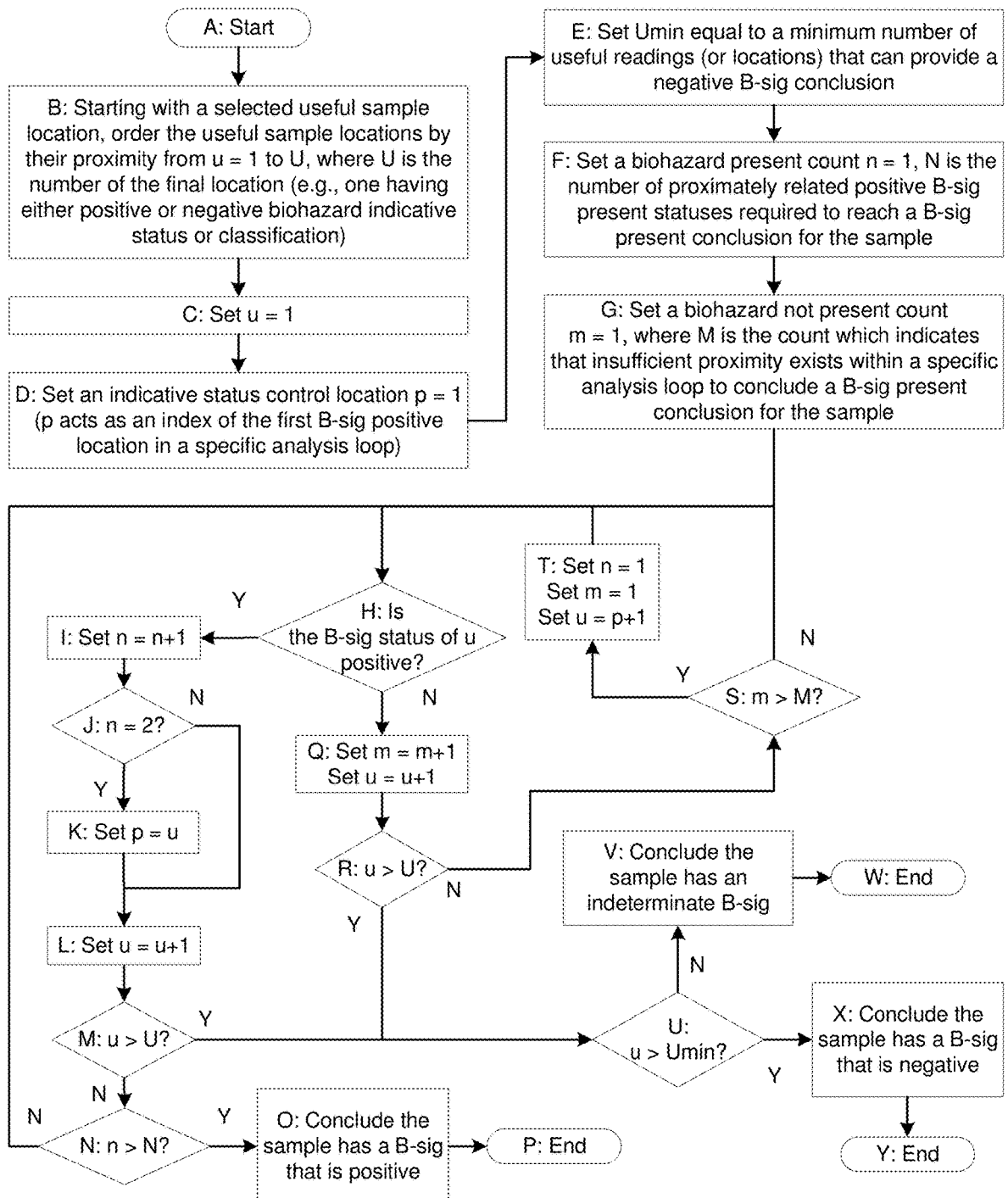
FIG. 2E provides a flowchart of an example process, or set of substeps, that may be used in implementing the spatial comparison part and conclusion derivation part of Block M of FIG. 2A.

FIG. 2E provides a flowchart of an example process, or set of substeps, that may be used in implementing the spatial comparison and conclusion derivation part of Block M of FIG. 2A. In the example of FIG. 2E, the method for forming a biohazard signature (B-sig) conclusion yields a positive, negative, or indeterminate biohazard signature presence conclusion based on each useful sample location being provided with a positive or negative classification (i.e. a B-sig positive of B-sig negative classification). In other embodiment variations, more nuanced classifications may be used and/or a fewer number, a greater number, and/or different conclusions may be obtained. The process of FIG. 2E begins with Block A and then moves to Block B.

Block B starts with a selected useful sample location (e.g. having a B-sig positive or B-sig negative classification or status) and orders the useful sample locations by their proximity from u=1 to U, where U is the number of the final location. From Block B, the process moves, respectively, to Blocks C-G which each involve setting and/or defining variable values and/or limits.

Block C sets a current location value, u, to 1, i.e. u=1.

Block D sets an indicative status control location, p, to 1, i.e. p=1, where p acts as an index of the first B-sig positive location in a given analysis loop.

Block E sets a variable Umin equal to a number of useful readings that are capable of providing a negative B-sig conclusion for a sample. This variable may be set by a user, a programmer defined algorithm, or may be defined as result of the training of a machine learning algorithm. In variations of the present embodiment, the use of, and decisions based on, Umin may be eliminated. In other alternatives, other steps and decisions may be used in determining whether an indeterminate biohazard status should be given.

Block F sets an initial biohazard present count n=1 and defines N as the number of B-sig present statuses that are required to be in proximity to one another to reach a B-sig present conclusion in a given specific loop analysis.

Block G sets an initial biohazard not present count, m, to a value of 1, i.e. m=1, and sets a maximum allowed intervening value count to M which represents a maximum number of intervening locations with negative classifications that may exist between N proximal locations with positive values to draw a B-sig present conclusion for the sample as a whole.

In the present embodiment, sufficient proximity of locations with positive B-sig classification is defined as N such locations existing without more than M intervening locations having non-positive (e.g., negative) B-sig classifications. In variations of the present embodiment, different values of N and M may be used which may be fixed values defined by a programmer, values tied to the spacing between adjacent locations, values tied to the number of locations read, or values derived from algorithm training that is intended to bring false positive and false negative conclusions and possibly sensitivity levels within an acceptable tolerance. For example, in some embodiments, N may take a value in the range of 5, or lower, to 30, or higher, while M may take a value ranging from 1 to 30, or higher, where the value of M may be tied to the value of N by a factor (e.g., M=N×0.05, or less, to M=N×1.5 or more). In other embodiments, other methods of validating or confirming sufficient proximity may be used which may involve a single grouping with sufficient proximity or multiple groups with each meeting less rigid proximity requirements.

After setting the control parameters by the operations of Blocks B-G, the process moves to Block H which makes the inquiry as to whether the B-sig status, or classification, of the current location u is positive. If the answer is yes, the process moves to Block I. If the answer is no, the process moves to Block Q.

Block I calls for incrementing the biohazard present count, n, by 1, i.e. n=n+1. Then the process moves to the inquiry of decision Block J, which asks if n=2. If the answer is no, the process skips the step of Block K and jumps to Block L. If the answer is yes, the process moves to Block K and sets the value of p, the initial location value of a positive B-sig value for the present loop analysis, to the current value of u, i.e. p=u. The intent of the value of p is to record and hold the starting location of the first location with a positive B-sig value for the current loop analysis wherein the current loop exists either until a determination of a B-sig positive conclusion is reached for the sample, the current loop exceeds M intervening no biohazard present locations prior to counting N proximal biohazard present locations, or the process ends because the number of useful locations was exceeded.

From either Block K, or from a no answer to the inquiry of Block J, the process moves forward to Block L which increments the current location value, u, by one, i.e. u=u+1. From Block L, the process moves to the inquiry of Block M where the question is posed as to whether u>U. If the answer is yes, the process moves to Block U because the current location count has exceeded the useful location count. If the answer is no, the process moves to decision block N where the question is posed as to whether n>N. If the answer is no, the process loops back to Block H where a determination can be made as to whether the next location contains a positive B-sig classification or not. If the answer to the question of Block N is yes, the process moves to Block O where a conclusion is made that the sample possesses the biohazard signature (i.e. biohazard signature is positive) because a sufficient number of proximally located B-sig classified locations were present in the current processing loop. From Block O, the process moves forward to Block P and ends. In other embodiments, additional processing may occur, for example, to provide a strength factor to the conclusion if such information is believed useful.

Before addressing Blocks U-Y, we turn back to Blocks Q-T. As noted above, Block Q is accessed by a negative response to the inquiry of Block H. In Block Q, the value of intervening locations m (i.e. locations with negative B-sig classifications within the current processing loop) is incremented by one, i.e. m=m+1 and the value of the location count is also incremented by one, i.e. u=u+1. From Block Q, the process moves forward to the inquiry of Block R where the question is posed as to whether u>U. If the answer is yes, the process moves forward to Block U (as did the process from a yes answer to the inquiry of Block M). Block U will be discussed further below. If the answer to the inquiry of Block R is no, the process moves to the inquiry of Block S, which poses the question as to whether m>M. The purpose of this inquiry is to determine whether to stay in the present analysis loop or to end the present loop to begin a new loop. If the answer to the inquiry of Block S is no, the process loops back to Block H. If the answer to the inquiry of Block S is yes, the process moves to Block T which resets several process values, thus effectively ending the current analysis loop. The steps of Block T result in setting the value of n to 1, the value of m to 1, and the value of u back to the value of p+1; i.e. n=1, m=1, and u=p+1.

Turning back to the inquiry of Block U, which is accessed from positive answers to the inquiries of Blocks M or R, the question is posed as to whether u>Umin to determine if there were sufficient useful or usable readings to reach a negative biohazard signature present conclusion. According to the assumptions in this embodiment, it is believed that in some situations, sufficient information may be extractable to reach a positive biohazard signature conclusion while not necessarily being able to reach a reasonable conclusion of non-biohazard signature presence. If the answer to the inquiry of Block U is yes, the process moves forward to Block X where a conclusion is reached that the sample has a negative B-sig classification and then the process moves to Block Y where the process ends. If the answer to the inquiry of Block U is no, the process moves forward to Block V where a conclusion is reached that the B-sig conclusion for the sample is indeterminate which may require the taking of another sample in hopes of reaching a definitive conclusion for a patient. In some variations, an indeterminate result may be used in combination with one or more additional indeterminate results to provide trending information particularly when the timing of the samples is known and where a B-sig strength factor can be associated with the results (e.g. how close a count n got to the value N in any signal analysis loop for each sample) wherein an increasing or decreasing trend in strength factors over time may be useful in making further assessments.

In addition to the process set forth in FIG. 2E, and the variations discussed above, other embodiments for moving the process from known biohazard location-by-location classifications to a biohazard signature status conclusion for samples as a whole are possible. Examples of such alternative processes are set forth herein next.

In a first such alternative, the forming of a biohazard indicative conclusion may be based on the following steps: selecting a given useful signal group (i.e. location) having a biohazard indicative status of likely biohazard presence, and successively looking at next nearest neighbor useful signal groups until either a count, n, of likely biohazard presence exceeds a value N (e.g. at least 3, 5, 7, 9, 11, 13, 15, 17 or more) in which case a biohazard indicative conclusion of "biohazard present" is made, or a count, m, of no likely biohazard presence exceeds M (e.g. at least 0, 1, 2, 3, or more), in which case the selecting and looking restarts with a new useful signal group having a likely biohazard presence indication, along with a reset of values of n and m, and the process continues until either a conclusion of biohazard presence is reached or all acceptable useful signal groups have acted as a starting point with no conclusion of biohazard presence being reached in which case a conclusion of "no biohazard presence" is reached. The process of this above alternative is similar to that of FIG. 2E with the primary exception that it does not consider a possible indeterminate status conclusion. In some variations of this embodiment, locations that were determined to not contain useful data may be ignored or counted as locations with no biohazard presence and thus be included when incrementing m.

In a second such alternative, the forming of a biohazard indicative conclusion may be based on the following steps which consider all measured locations and their classification as positive, negative, indeterminate, or unusable and uses each such classification in drawing a conclusion. The process starts by selecting a given useful signal group having a biohazard indicative status of likely biohazard presence, and successively looking at next nearest neighbor signal groups until either a count of likely biohazard presence, n, exceeds a value N (e.g. at least 3, 5, 7, 9, 11, 13 or more) in which case a biohazard indicative conclusion of "biohazard present" is made, or a count of no likely biohazard presence, m, exceeds M (e.g. at least 0, 1, 2, 3, or more, or an amount that is a percentage of N, e.g. something between 2%-50%), a count of unusable signal groups, r, exceeds R (e.g. at least 0, 1, 2, 3, or more, or an amount that is a percentage of N, e.g. between 2%-50%), or a count of groups having indeterminate biohazard statuses, s, exceeds S (e.g. at least 0, 1, 2, 3, or more, or an amount that is a percentage of N, e.g. between 2%-50%), or some combined sum, t, associated with M, R, and/or S exceeds an amount T (e.g. at least 0, 1, 2, 3, or more, or an amount that is a percentage of N, e.g. between 2%-50%) in which case the selecting and looking restarts with a new useful signal group having a likely biohazard presence indication along with the resetting of values for m, n, r, and s, and the process continues until either a conclusion of biohazard presence is reached or all acceptable useful signal groups have acted as a starting point with no conclusion of biohazard presence being reached in which case a conclusion of "no biohazard presence" is reached.

In a third such alternative, the forming of a biohazard indicative conclusion may be based on the following steps which considers all measured locations and their classification as positive, negative, indeterminate, or unusable and treats such classification when producing a biohazard status conclusion for the sample. The process starts with selecting a given useful signal group having a biohazard indicative status of likely biohazard presence, and successively looking at next nearest neighbor signal groups until either a count of likely biohazard presence, n, exceeds a value N (e.g. at least 3, 5, 7, 9, 11, 13 or more) in which case a biohazard indicative conclusion of "biohazard present" is made, or a count of no likely biohazard presence, m, exceeds M (e.g. at least 0, 1, 2, 3, or more, or an amount that is a percentage of N, e.g. between 2%-50%), a count of unusable signal groups, r, exceeds R (e.g. at least 0, 1, 2, 3, or more, or an amount that is a percentage of N, e.g. between 2%-50%), or a count of groups having indeterminate biohazard statuses, s, exceeds S (e.g. at least 0, 1, 2, 3, or more, or an amount that is a percentage of N, e.g. between 2%-50%), or some combined sum, t, associated with M, R, and/or S exceeds an amount T (e.g. at least 0, 1, 2, 3, or more, or an amount that is a percentage of N, e.g. between 2%-50%), wherein the count of one or more of M, R, or S is reset to 0 when a count of successive nearest neighbors having likely biohazard presence status exceeds U (e.g. where U is at least 2, 3, 4, or more or is some fraction of N), wherein if any of M, R, S, or T is exceeded the selecting and looking restarts with a new useful signal group, and reset sums, having a likely biohazard presence indication, and the process continues until either a conclusion of biohazard presence is reached or all acceptable useful signal groups have acted as a starting point with no conclusion of biohazard presence being reached in which case a conclusion of "no biohazard presence" is reached.

In other alternatives, the forming of a biohazard indicative conclusion may be based on meeting one of more of the following alternative criteria. A first alternative set of criteria includes a plurality of neighboring biohazard indicative statuses, each providing an indication of the likely presence of a biohazard signature (e.g., classification is positive), wherein a number of the plurality is selected from the group consisting of: (i) at least three, (ii) at least five, (iii) at least seven, (iv) at least ten, (vi) at least fifteen, and (vii) at least twenty-five.

A second alternative set of criteria includes at least N % of a plurality of nearest neighbor biohazard indicative statuses providing an indication of the likely presence of the biohazard (e.g., classification is positive), wherein a number of the plurality is selected from the group consisting of: (i) at least five, (ii) at least seven, (iii) at least ten, and (iv) at least fifteen, (v) at least twenty-five and wherein N is selected from the group consisting of: (i) greater than 50%, (ii) greater than 65%, (iii) greater than 80%, and (iv) greater than 90%.

A third alternative set of criteria includes a plurality of nearest neighbor biohazard indicative statuses, each providing an indication of the likely presence of the biohazard (e.g., classification is positive), with a possible exception of one that may provide an indeterminate presence (e.g. classification is neither positive or negative) of the biohazard or an indication of no likely presence of the biohazard (e.g. classification is negative), or be associated with locations determined to be unusable, wherein a number of the plurality is selected from the group consisting of: (i) at least five, (ii) at least seven, (iii) at least ten, (iv) at least fifteen, and (v) at least twenty-five.

A fourth alternative set of criteria includes a plurality of neighboring biohazard indicative statuses being determined to provide an indication of the likely presence of the biohazard using a trained K nearest neighbor machine learning algorithm to provide location-by-location classification where K is a whole number greater than or equal to one (e.g. 1, 2, more than 2, more than 4, or more than 6) with a possible exception of the larger of X % or at least M that may provide an indication of no likely presence of the biohazard (e.g. classification is negative), and the larger of Y % or at least P that may provide an indeterminant indication of the presence of the biohazard (e.g. classification is neither positive or negative), wherein a number of the plurality is, for example: (i) at least five, (ii) at least seven, (iii) at least ten, (iv) at least fifteen, or (v) at least twenty-five; wherein X is, for example: (i) at least 5%, (ii) at least 10%, or (iii) at least 20%; wherein M is, for example: (i) at least 1, (ii) at least 2, (iii) at least 3; wherein Y is, for example: (i) at least 7.5%, (ii) at least 15%, or (iii) at least 30%; and wherein P is, for example: (i) at least 2, (ii) at least 4, or (iii) at least 6.

A fifth alternative set of criteria includes at least M clusters (e.g., M=1, 2, 3, 4, 5, or more) of N or more biohazard likely indicative statuses (e.g., N=11, 9, 7, 5, 3) or any of one or more alternative (M,N) combinations (e.g. (1,11), (2,9), (3,7), (4,5), (5,3), and the like) from substantially non-overlapping sample positions.

A sixth alternative set of criteria includes at least M biohazard indicative statuses associated with a plurality of N different portions of the sample that are proximate to one another (e.g., neighboring locations are physically separated by at least R exposure widths and no more than S exposure widths); wherein M is, for example: (i) at least 3, (ii) at least 5, (iii) at least 9, (iv) at least 15, or (v) at least 25; wherein N is selected from, for example: (i) at least 50, (ii) at least 100, (iii) at least 200, (iv) at least 400, and (v) at least 800, wherein R is, for example: (i) no less than ¼, (ii) no less than ½, (iii) no less than ¾, (iv) no less than 1, or (v) no less than 5/4; and wherein S is, for example: (i) no more than 2, (ii) no more than 5, (iii) no more than 10, and (iv) no more than 20.

A seventh alternative set of criteria includes a majority (i.e., greater than 50%) or a supermajority of (e.g., greater than ⅔, ¾, ⅘, ⅚, ⅞, 8/9, 9/10, or the like) N non-overlapping measurement locations possessing biohazard present indicative statuses (i.e. classifications) in proximity to one another where N is at least 5 neighboring locations, at least 10 neighboring locations, at least 20 neighboring locations, or at least 50 neighboring locations.

An eighth set of alternative criteria includes at least F out of FF neighboring biohazard classifications from useful locations providing likely biohazard present statuses based on fluorescence emission detections and at least R out of RR neighboring biohazard classifications from useful locations providing likely biohazard present statuses based on Raman emission detections locations where potential R locations are common with the F locations and wherein (i) F>=R, (ii) F/R (i.e. F divided by R) is, for example: (1) >=3/2, (2) >=5/3, (3) >=7/4, (4) >=15/11, and (iii) FF and RR are selected from the group consisting of: (1) at least 20, (2) at least 50, (3) at least 100, (4) at least 200, (5) at least 400, and (6) at least 800.

Numerous variations to the processes of FIGS. 2A-2E are possible with some having been discussed above while others will be apparent to those of skill in the art upon review of the teachings herein.

FIG. 3 provides a spectroscopic method for determining whether a biohazard signature is present in a sample according to a third embodiment of the invention that is similar to that of FIG. 2A with major exception that Blocks J-N of FIG. 2A are shifted to Blocks K-O with a new Block J being inserted which specifically calls for a comparison of data for individual sample locations to be compared to data associated with samples of known biohazard signature status with some indicative of biohazard presence and others indicative of no biohazard presence. As with FIGS. 1A, 1B, and 2A, alternative embodiments exist which may add in additional steps, may remove or modify some steps, may change the order of operation of some steps and/or provide parallel processing of some steps.

FIG. 4 provides a schematic representation of a system 400 according to a fourth embodiment of the invention that may be used for providing analysis of samples 406 for biohazard signature identification (i.e. determination of direct or indirect biohazard presence) wherein the system provides a number of the components (e.g. a deep UV radiation source 402, at least one spectral separator 412, and at least one emission radiation detector 416, and a window or opening 401-1 for passing excitation radiation 404 and emission radiation 408) within or as part of an analytical instrument housing or package 401 but where the instrument is provided with an external controller 424, power 426, and data processing and analysis hardware 428 and an external stage 430 for providing movement of an external sample relative to a fixed location of excitation radiation exposure and emission radiation generation so as to provide for a plurality of sample locations from which spectral information can be gathered and used along with spatial relationships of multiple sample locations in identification assessments. In operation, the excitation radiation 404 is passed from the source 402 through the window or opening 401-1 to strike a sample 406 supported by the stage 430. The sample in turn produces emission radiation 408 which passes back through the window or opening to at least one spectral separator 412 which in turn causes emission radiation in distinct bands 414 to reach the at least one detector 416. Power is supplied to the controller via link 425A. The controller in turn supplies control signals and power to the source 402 via link 425B, to the spectral separator (if needed) via link 425E, to the at least one detector via link 425C, and to the stage 430 via link 425D. Measurement and other operational information is in turn provided back along these links to the controller and then to the analyzer 428 via link 425F. The system makes use of hard coded or programmed control and analysis algorithms and/or trained artificial intelligence algorithms along with inputs to provide system control and outputs to provide results and other operational information. In some variations, the controller and analyzer may be part of a single processor or computer system with common inputs and outputs while in other embodiments, they may exist as separate processors or computer systems with separate or common inputs and outputs. Numerous other alternatives to the system of FIG. 4 are possible, including, for example, use of other power and signal transmission links, use of alternative components and/or additional components for achieving desired functionality, and use of other component configurations and relationships.

Figure 5:
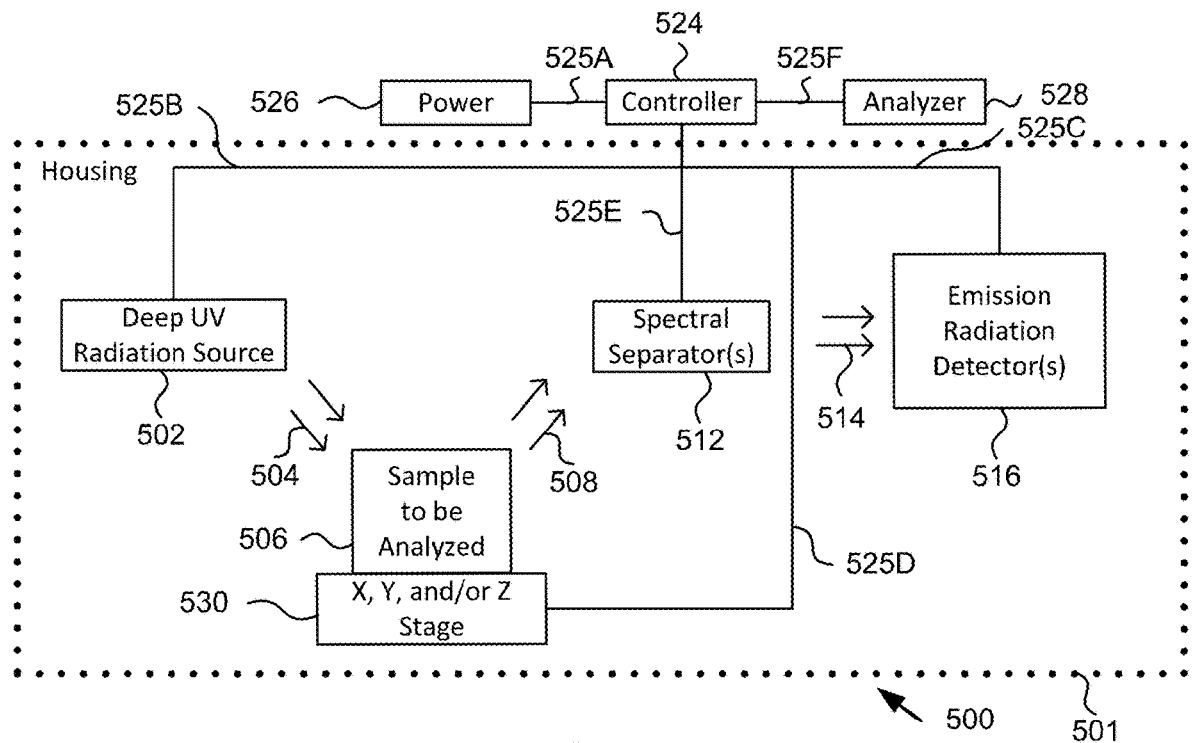
FIG. 5 provides a schematic representation of a system according to a fifth embodiment of the invention that is similar to that of FIG. 4 with the exception that the external stage and sample reading location is replaced with an internal stage that holds a sample that is placed within a housing of the analytical instrument.

FIG. 5 provides a schematic representation of a system according to a fifth embodiment of the invention that is similar to that of FIG. 4 with the exception that the external stage and sample reading location is replaced with an internal stage 530 that holds a sample 506 that is placed within the analytical instrument itself via a door, slot, opening or other input passage (not shown). Similar components of FIGS. 4 and 5 are provided with similar reference numbers, but FIG. 4 uses numbers in the 400 series while FIG. 5 uses numbers in the 500 series. Numerous alternatives to the embodiment of FIG. 5 are possible and include those noted for FIG. 4 as well as for the other embodiments set forth herein, mutatis mutandis, so long as such alternatives do not completely remove the functionality or all the uniqueness of the embodiment of FIG. 5. In some variations, for example, the sample may be sealed or enclosed before insertion into the instrument so as to minimize risk of contaminating the instrument while in other embodiments, no such sealing may be used.

Figure 6:
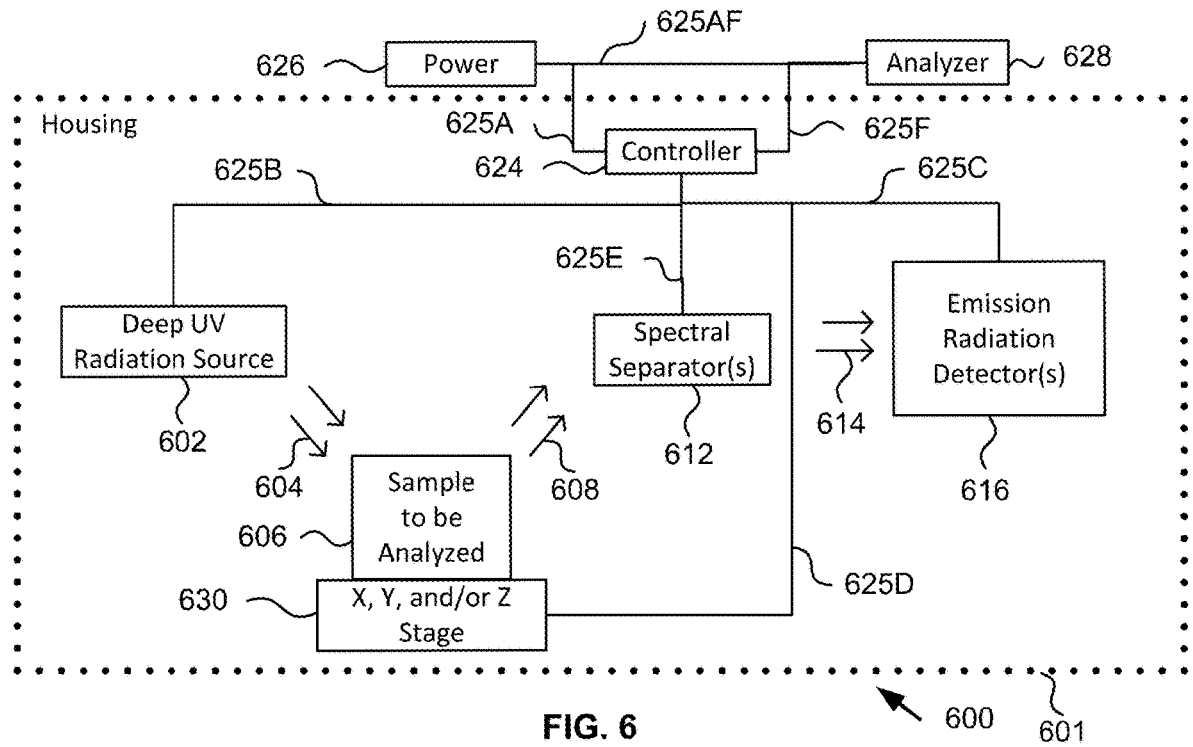
FIG. 6 provides a schematic representation of a system according to a sixth embodiment of the invention that is similar to that of FIG. 5 with the exception that the external controller is replaced with an internal controller that is located within the housing of the analytical instrument.

FIG. 6 provides a schematic representation of a system according to a sixth embodiment of the invention that is similar to that of FIG. 5 with the exception that the external controller is replaced with an internal controller 624 that is located within the housing of the analytical instrument and where direct power can be supplied to the analyzer along link 625AF as well as via the controller along link 625F. Similar components of FIGS. 5 and 6 are provided with similar reference numbers, but FIG. 5 uses numbers in the 500 series while FIG. 6 uses numbers in the 600 series. Numerous variations to the embodiment of FIG. 6 are possible and include those noted for FIGS. 4 and 5 as well as alternative features set forth in the other embodiments herein, mutatis mutandis, so long as those variations and alternatives do not completely remove the functionality or all the uniqueness of the embodiment of FIG. 6.

Figure 7:
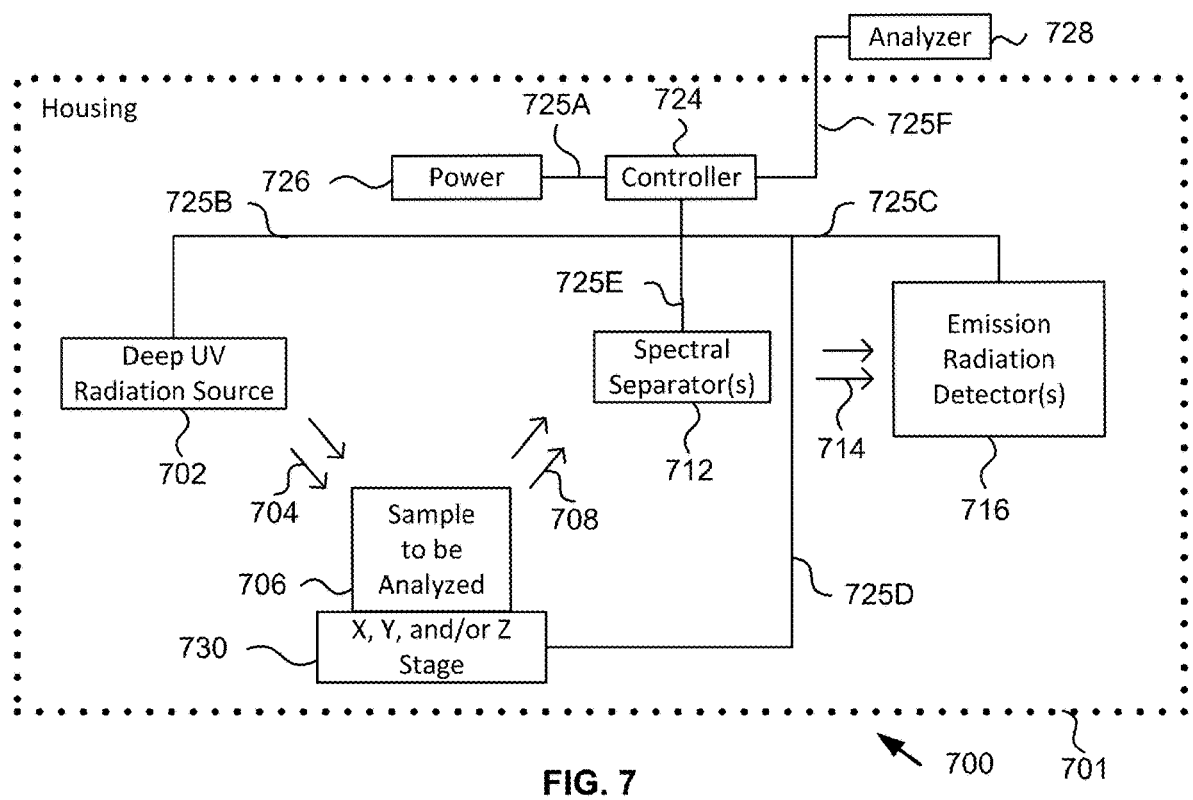
FIG. 7 provides a schematic representation of a system according to a seventh embodiment of the invention that is similar to that of FIG. 6 with the exception that the external power source is replaced by an internal power source (e.g., a battery, a fuel cell, a photo voltaic cell) that is located within or as part of a housing of the analytical instrument.

FIG. 7 provides a schematic representation of a system according to a seventh embodiment of the invention that is similar to that of FIG. 6 with the exception that the external power source is replaced by an internal power source 726 (e.g. a battery, a fuel cell, a photo voltaic cell) that is located within, or as part of, a housing of the analytical instrument and wherein the direct link between the power source and the analyzer is eliminated. Similar components of FIGS. 6 and 7 are provided with similar reference numbers, but FIG. 6 uses numbers in the 600 series while FIG. 7 uses numbers in the 700 series. Numerous alternatives to the embodiment of FIG. 6 are possible and include those noted for FIGS. 4-6 as well as for the other embodiments set forth herein, mutatis mutandis, so long as those variations do not completely remove the functionality or all the uniqueness of the embodiment of FIG. 7. For example, in some variations the analyzer may use power from the power source within the housing while in other variations, the power for the analyzer may come from an external source (e.g. a separate battery or a wall outlet while link 725F is used to convey data and/or other communication signals. In other variations, the link 725F, as is true for other links, may be of a wired or a wireless type.

Figure 8:
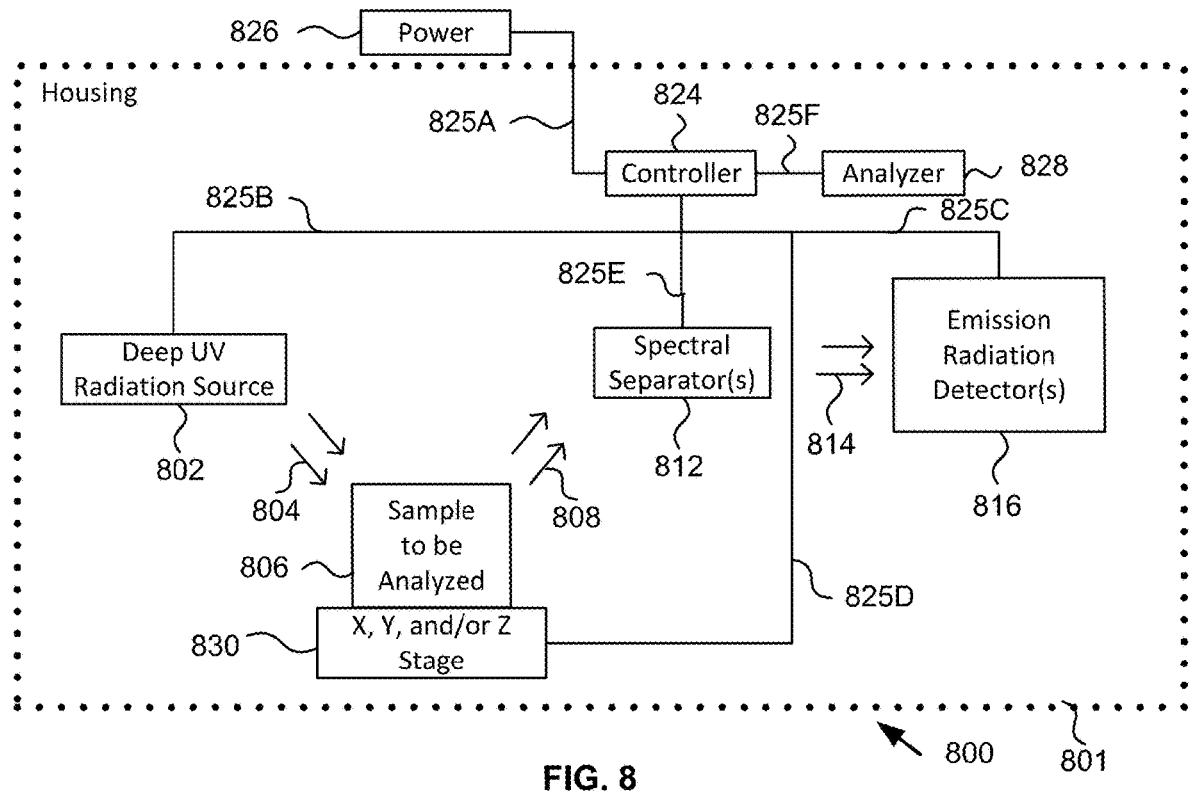
FIG. 8 provides a schematic representation of a system according to an eighth embodiment of the invention that is similar to that of FIG. 6 with the exception that the external analyzer is replaced by an internal analyzer that is located within a housing of the analytical instrument.

FIG. 8 provides a schematic representation of a system according to an eighth embodiment of the invention that is similar to that of FIG. 7 with the exception that the external analyzer 728 is replaced by an internal analyzer 828 that is located within a housing of the analytical instrument and the internal power source 726 becomes an external source 826. Similar components of FIGS. 7 and 8 are provided with similar reference numbers, but FIG. 7 uses numbers in the 700 series while FIG. 8 uses numbers in the 800 series. Numerous alternatives to the embodiment of FIG. 8 are possible and include those noted for FIGS. 4-7 as well as those noted for the other embodiments set forth herein, mutatis mutandis, so long as those variations do not completely remove the functionality or all the uniqueness of the embodiment of FIG. 8.

Figure 9:
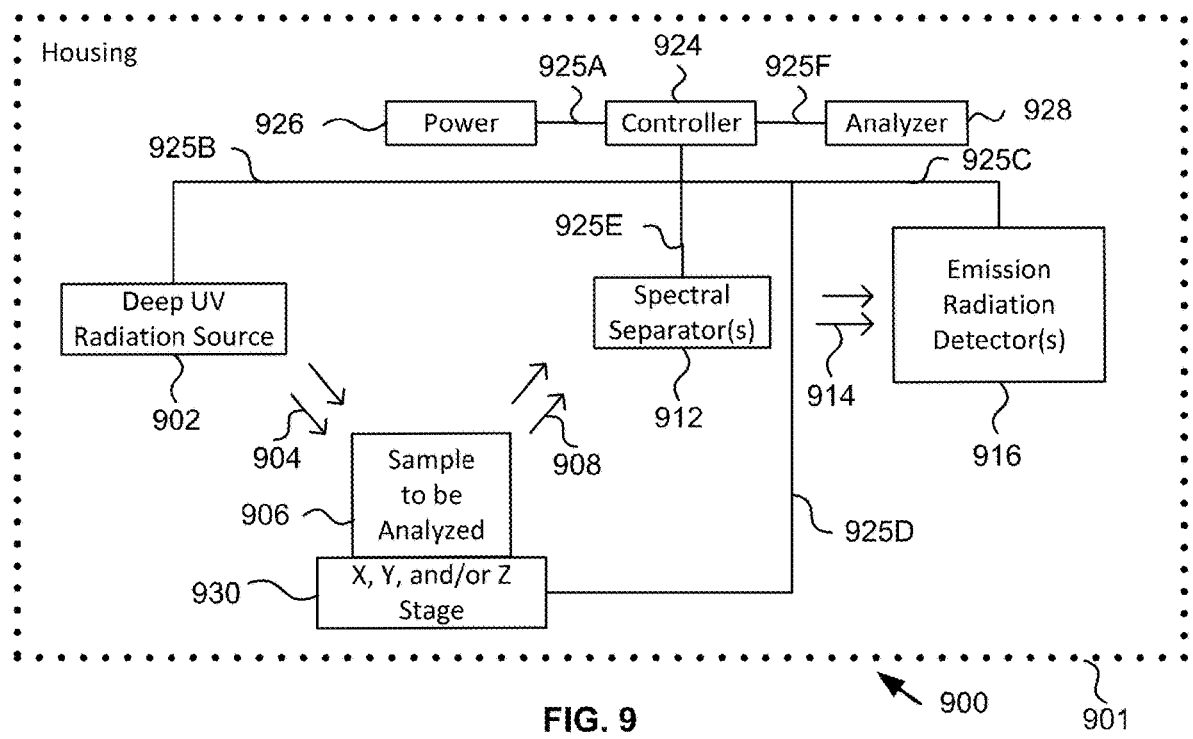
FIG. 9 provides a schematic representation of a system according to a ninth embodiment of the invention that is similar to that of FIG. 6 with the exception that the external analyzer and external power source are replaced by an internal analyzer and internal power source that are located within a housing of the analytical instrument.

FIG. 9 provides a schematic representation of a system according to a ninth embodiment of the invention that is similar to that of FIG. 8 with the exception that the external power source 826 is replaced by an internal power source 926 (e.g., a battery, a fuel cell, a photo voltaic cell, or the like) that is located on or within a housing of the analytical instrument. Similar components of FIGS. 8 and 9 are provided with similar reference numbers, but FIG. 8 uses numbers in the 800 series while FIG. 9 uses numbers in the 900 series. Numerous alternatives to the embodiment of FIG. 9 are possible and include those noted for FIGS. 4-8 as well as those noted for the other embodiments set forth herein, mutatis mutandis, so long as those variations do not completely remove the functionality or all the uniqueness of the embodiment of FIG. 9.

Figure 10:
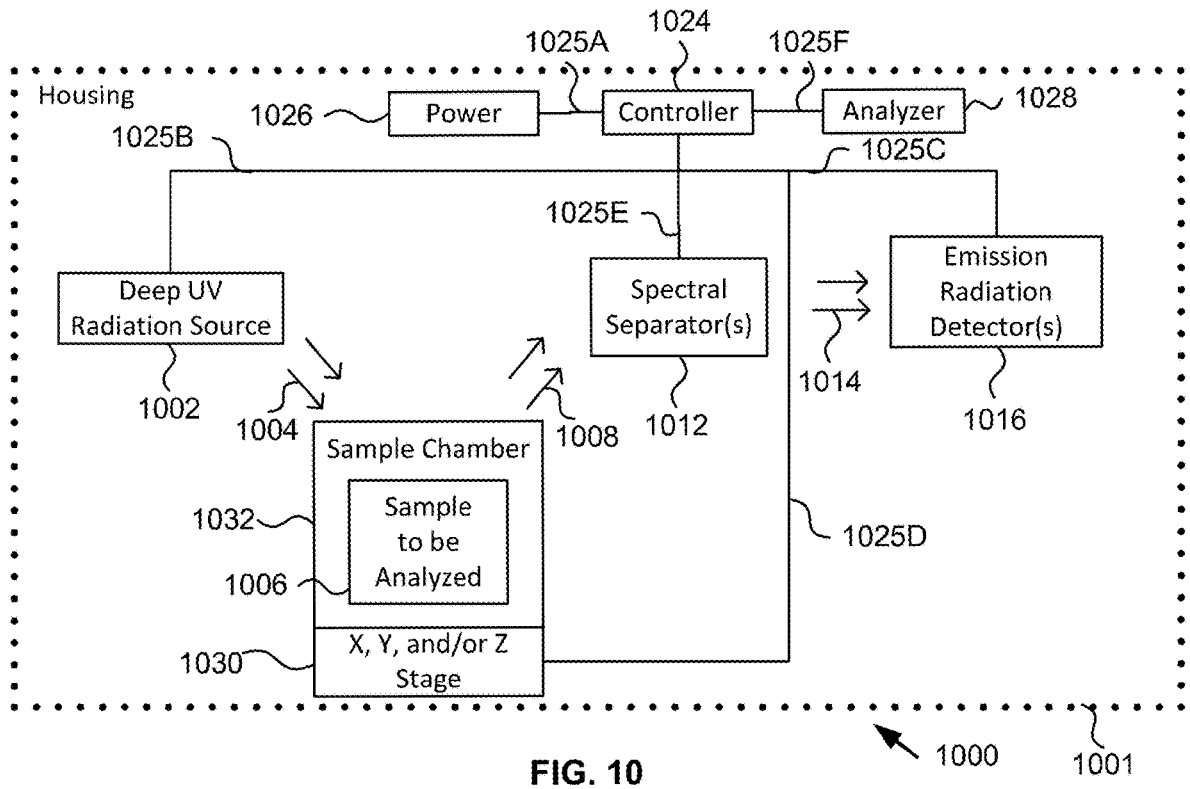
FIG. 10 provides a schematic representation of a system according to a tenth embodiment of the invention that is similar to that of FIG. 9 with the exception that the sample to be analyzed is located in a removable sample chamber that can be placed within the housing.

FIG. 10 provides a schematic representation of a system according to a tenth embodiment of the invention that is similar to that of FIG. 9 with the exception that the sample to be analyzed is located in a fixed or removable sample chamber 1032 that can be placed within the housing 1001. Similar components of FIGS. 9 and 10 are provided with similar reference numbers, but FIG. 9 uses numbers in the 900 series while FIG. 10 uses numbers in the 1000 series. Numerous alternatives to the embodiment of FIG. 10 are possible and include those noted for FIGS. 4-9 as well as those noted for the other embodiments set forth herein, mutatis mutandis, so long as those variations do not completely remove the functionality or all the uniqueness of the embodiment of FIG. 10. In other variations of this embodiment, the sample chamber may provide a sealed container for holding one or more samples and it may be loadable and removable with the sample or samples so that it may be sterilized or cleaned before loading in new samples or after removing the sample or samples. In embodiments where the chamber is capable of holding more than one sample, it may include a means separate from stage 1030 to move samples in and out of an exposure or detection path. Such means may provide a binary movement from a hold position to a test position (and possibly back to the hold position) or it may provide for more nuanced movement that can be used to supplement the positioning provided by the stage. The means may include, for example, a simple manually positionable stage (X, Y and/or Z), a manually positionable rotational stage with or without positioning detents, a robotic arm and hand (e.g. with a gripping claw, a vacuum chuck, a magnetic chuck, or the like, and/or it may be motorized or even operate under computer control (and associated programming). It may also provide for movement of samples from or within a multiple sample holder to allow movement between storage positions and loading or unloading positions. It may also include sensors and associated algorithms for optimizing movement and reliability of sample placement and/or providing feedback to a system operator. In some embodiments, the system may include an optical scanner, bar code reader, a RF reader for reading tags or other markings on sample substrates or containers where such read information may be stored along with spectroscopic or other data extracted from the sample itself. Such tags may be affixed to the sample substrate or container at the time of sample gathering or at some other point and may include sample identification information or other information about the sample, its gathering method, the location where it was gathered, and/or the time of gathering. If the sample is from a human or animal, additional information may be included such as medical history, current symptoms, and/or demographic information while if from an inanimate object, the information might include, for example, specific information about the general or specific environment around gathering location, recent events or history concerning the gathering site.

Figure 11:
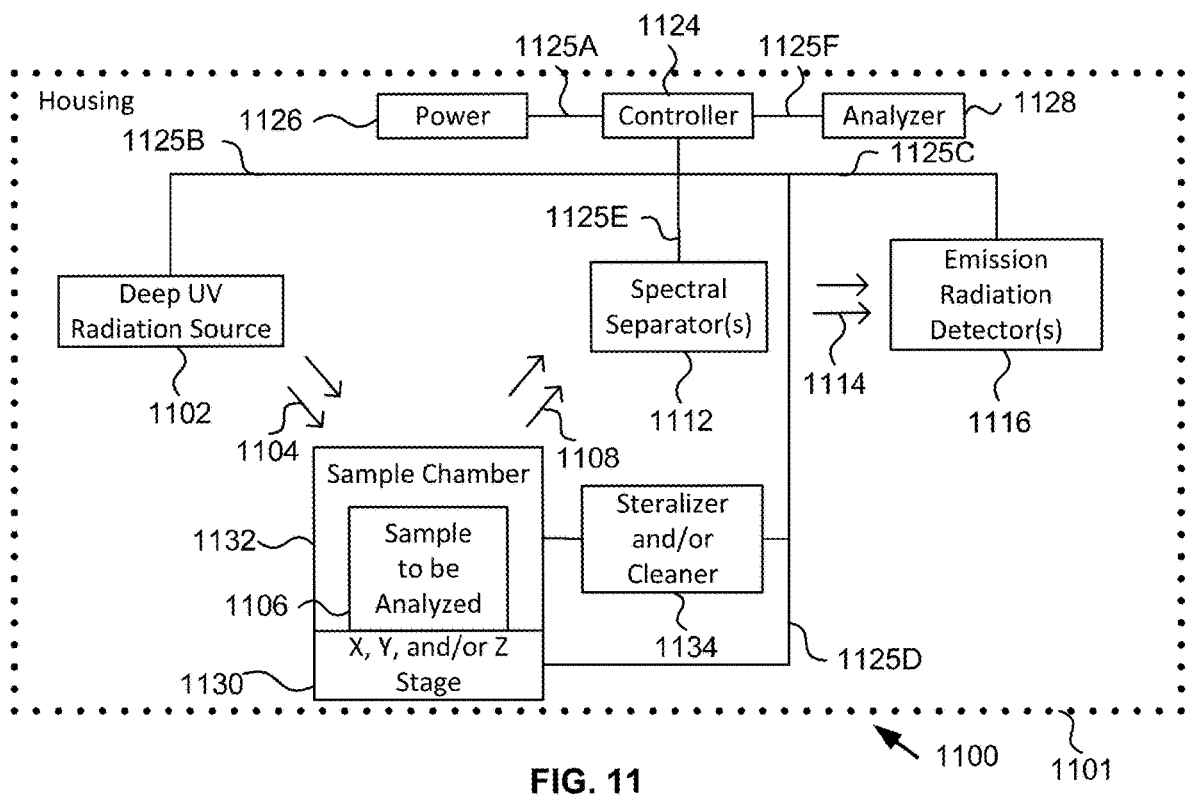
FIG. 11 provides a schematic representation of a system according to an eleventh embodiment of the invention that is similar to that of FIG. 9 with two exceptions: (1) the sample to be analyzed is located in a sample chamber within the housing that may be similar to that of FIG. 10 or may not be loadable into and removable along with a sample, and (2) the housing includes a sterilizer and/or cleaner which may be used to ensure sample chamber or instrument cleanliness and/or sterility is maintained to avoid cross-contamination of samples and inadvertent exposure of users to biohazards.

FIG. 11 provides a schematic representation of a system according to an eleventh embodiment of the invention that is similar to that of FIG. 10 with the exception that the housing includes a sterilizer and/or cleaner 1134 that may be used to ensure sample chamber or instrument cleanliness and/or sterility is maintained to avoid cross-contamination of samples and inadvertent exposure of users to biohazards. Similar components of FIGS. 10 and 11 are provided with similar reference numbers, but FIG. 10 uses numbers in the 1000 series while FIG. 11 uses numbers in the 1100 series. In some embodiments, such sterilization systems may include UV radiation sources, ozone sources, chemical sterilizers, heaters, fans, filters, and other components and controllers for operating them to provide the desired sterilization, cleaning, or verification. In some variations, sterilization may be limited to killing or deactivation of biological agents while in others, it may include removal of such agents along with inorganic contaminates to avoid the instrument producing inaccurate results (e.g. false positives). Numerous other alternatives to the embodiment of FIG. 11 are possible and include those noted for FIGS. 4-10 as well as those noted for the other embodiments set forth herein, mutatis mutandis, so long as those variations do not completely remove the functionality or all the uniqueness of the embodiment of FIG. 11.

Figure 12:
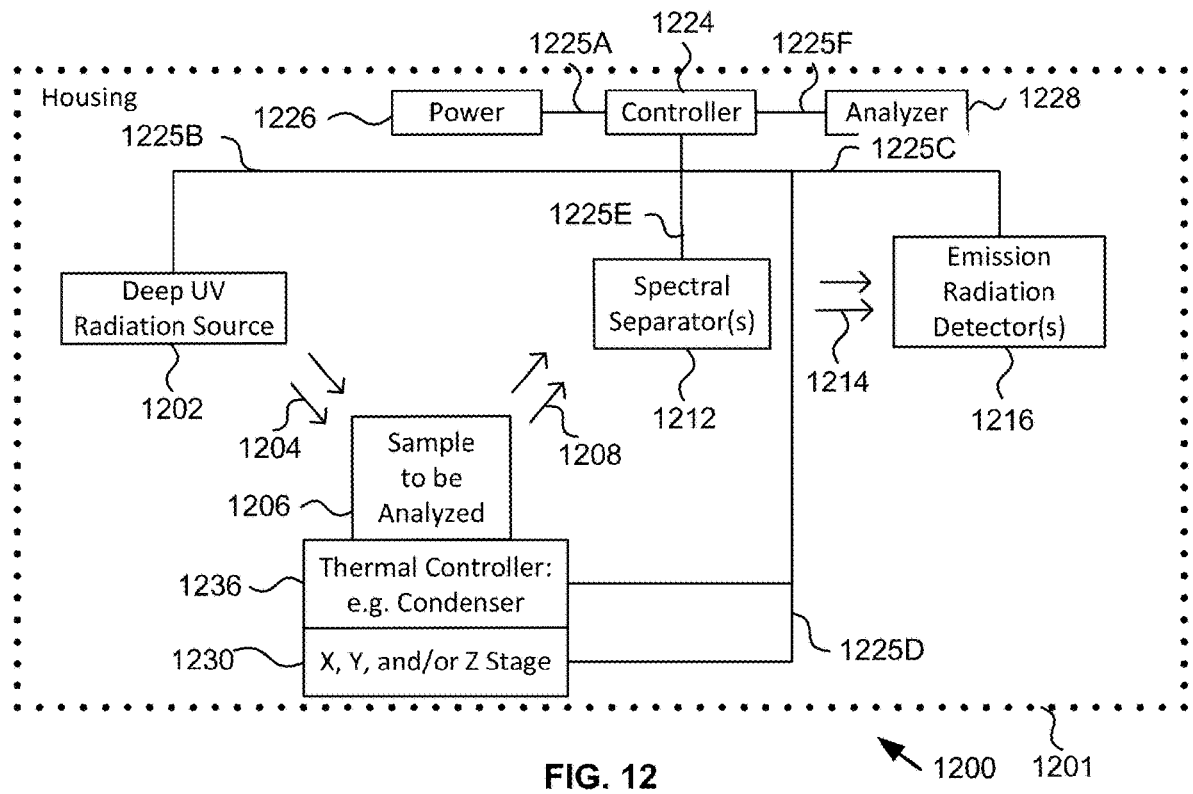
FIG. 12 provides a schematic representation of a system according to a twelfth embodiment of the invention that is similar to that of FIG. 9 with the exception that the system additionally includes a controller for controlling the temperature of the sample or of a sample location.

FIG. 12 provides a schematic representation of a system according to a twelfth embodiment of the invention that is similar to that of FIG. 9 with the exception that the system additionally includes a thermal controller 1236 for controlling the temperature of the sample or of a sample location. Similar components of FIGS. 12 and 11 are provided with similar reference numbers, but FIG. 11 uses numbers in the 1100 series while FIG. 12 uses numbers in the 1200 series. This temperature controller may be used for one or more purposes including for example, one or more of condensing airborne material onto the sample location for biohazard presence examination and vaporizing condensed material for removal or sterilization. In some variations, the controller may provide one or more heating elements, in others it may provide one or more cooling elements, in others it may provide an intake or exhaust fan, along with filters and/or sterilizers for treating exhausted air, while in others it may provide a combination of the two or more of the above example elements along with appropriate power and control elements and functionality. Numerous other alternatives to the embodiment of FIG. 12 are possible and include those noted for FIGS. 4-11 as well as those noted for the other embodiments set forth herein, mutatis mutandis, so long as those variations do not completely remove the functionality or all the uniqueness of the embodiment of FIG. 12.

Figure 13:
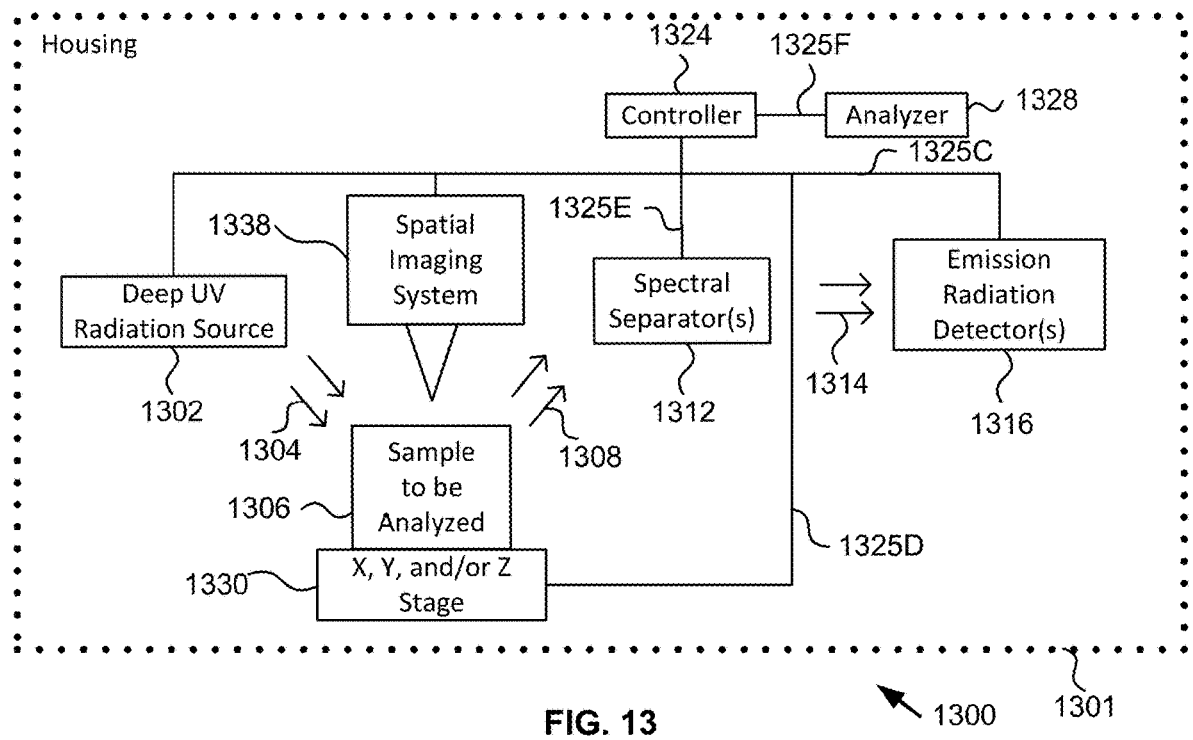
FIG. 13 provides a schematic representation of a system according to a thirteenth embodiment of the invention that is similar to that of FIG. 9 with the exception that the system additionally includes a spatial imaging system that can provide images (e.g., still or video images) of the sample location before, during, or after application of excitation radiation.

FIG. 13 provides a schematic representation of a system according to a thirteenth embodiment of the invention that is similar to that of FIG. 9 with the exception that the system additionally includes a spatial imaging system that can provide images (e.g. using a still or video camera system operating in one or more of visible, UV, or IR wavelength ranges, possibly using a separate illumination source, possibly using image processing or manipulation software, and an image or video display) of the sample location before, during, or after application of excitation radiation. Similar components of FIGS. 13 and 12 are provided with similar reference numbers, but FIG. 12 uses numbers in the 1200 series while FIG. 13 uses numbers in the 1300 series. Numerous other alternatives to the embodiment of FIG. 13 are possible and include those noted for FIGS. 4-12 as well as those noted for the other embodiments set forth herein, mutatis mutandis, so long as those variations do not completely remove the functionality or all the uniqueness of the embodiment of FIG. 13. In some variations, the imaging system may provide, for example: (1) illumination of a sample area with IR radiation, (2) illumination of a sample area with near UV radiation, (3) illumination of a sample area with visible light, (4) illumination of a sample area with UV radiation, (5) illuminating radiation as narrow band radiation; (6) illuminating radiation as broad band radiation, (7) showing of captured images or video on a display that is part of the analytic instrument, (8) showing of image or video data on a display system that is separate from the analytical instrument, (9) images showing the entire sample location, (10) images showing only selected portions of the display at any given time, (11) images for manual or automatic positioning of the sample before or during data acquisition, (12) images showing which portions of the sample are associated with exposure locations; and/or (13) images or video that may be aid in the data processing that leads to a better or faster biohazard signature conclusion.

Figure 14:
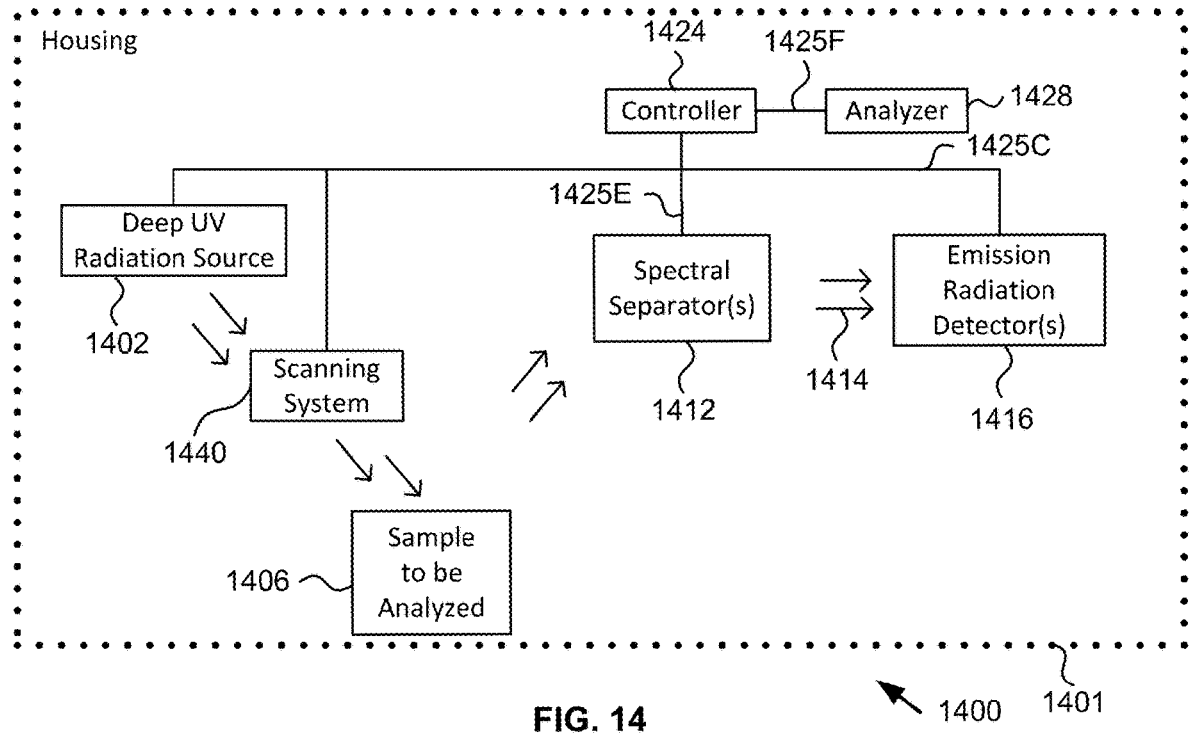
FIG. 14 provides a schematic representation of a system according to a fourteenth embodiment of the invention that is similar to that of FIG. 9 with the exception that the stage for causing relative movement of the sample is replaced by a scanning system that directs excitation radiation onto different locations and thus produces emission radiation from different locations on a sample.

FIG. 14 provides a schematic representation of a system according to a fourteenth embodiment of the invention that is similar to that of FIG. 9 with the exception that the stage for causing relative movement of the sample is replaced by at least one scanning mirror (as part of scanning system 1440) that directs excitation radiation onto different locations of a sample and thus produces emission radiation from different locations on a sample. Similar components of FIGS. 14 and 13 are provided with similar reference numbers, but FIG. 13 uses numbers in the 1300 series while FIG. 14 uses numbers in the 1400 series. Numerous other alternatives to the embodiment of FIG. 14 are possible and include those noted for FIGS. 4-13 as well as elements or features found in the other embodiments set forth herein, mutatis mutandis, so long as those variations do not completely remove the functionality or all the uniqueness of the embodiment of FIG. 14. Additional variations of the embodiment of FIG. 14 may provide the at least one scanning mirror system as (1) one or more galvanometer scanning mirrors, (2) one or more stepper motor driven scanning mirrors, (3) one or more rotational scanning mirrors, (4) one or more tip/tilt scanning mirrors, (5) one or more oscillating scanning mirrors, (6) one or more flying spot scanning mirror systems, (7) one or more polygonal scanning mirrors, (8) one or more raster scanning mirror systems, (9) one or more dither mirror systems, (10) one or more oscillating mirror scanning systems, and (11) a scanning system capable of two dimensional scanning. The scanning mirror systems of the different variations may provide additional components to achieve different functionalities, such as, for example, one or more programmed controllers that provide for operation of the scanning system along with correlated operation of other system components, focusing elements or systems, beam attenuation elements or systems, positioning feedback components or systems, positioning calibration components or systems, intensity or optical power feedback components or systems.

Figure 15:
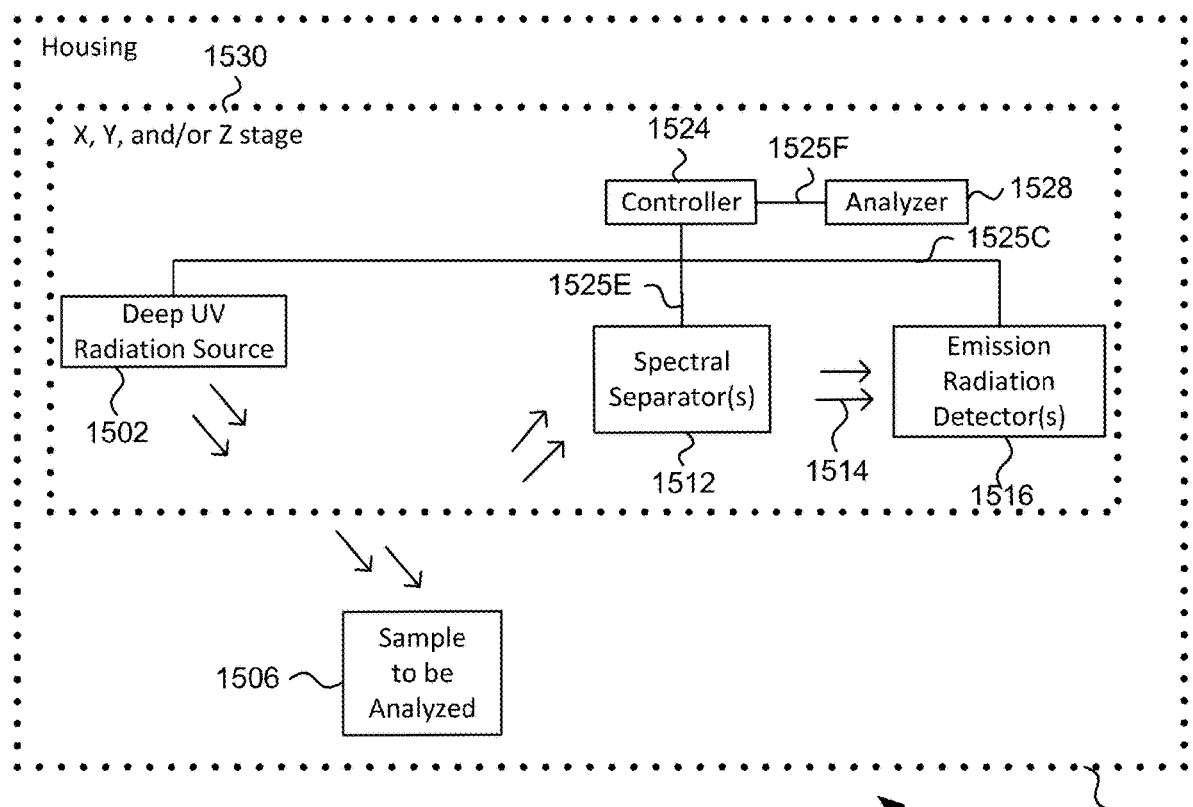
FIG. 15 provides a schematic representation of a system according to a fifteenth embodiment of the invention that is similar to that of FIG. 9 with the exception that in the system, the stage that moves the sample location relative to the fixed exposure location is replaced by a stage that shifts the exposure, and possibly the detection, components, module, or modules so as to provide the required relative motion and thus different exposure locations on a sample while leaving the sample in a fixed position.

FIG. 15 provides a schematic representation of a system according to a fifteenth embodiment of the invention that is similar to that of FIG. 9 with the exception that in the system, the stage that moves the sample location relative to the fixed exposure location is replaced by a stage 1530 that shifts the exposure, and possibly the detection, components, module, or modules so as to provide the required relative motion and thus different exposure locations on a sample while leaving the sample in a fixed position. Similar components of FIGS. 15 and 14 are provided with similar reference numbers, but FIG. 14 uses numbers in the 1400 series while FIG. 15 uses numbers in the 1500 series. Numerous other alternatives to the embodiment of FIG. 15 are possible and include those noted for FIGS. 4-14 as well as those noted for the other embodiments set forth herein, mutatis mutandis, so long as those variations do not completely remove the functionality or all the uniqueness of the embodiment of FIG. 15. Other variations might include replacing the movable stage of FIG. 15 with a tilt system that tilts the radiation source and associated optics and possibly the detection system and associated optics to cause excitation radiation to strike different sample locations and the detection system to optimally receive produced emission radiation coming from the different locations.

Figure 16:
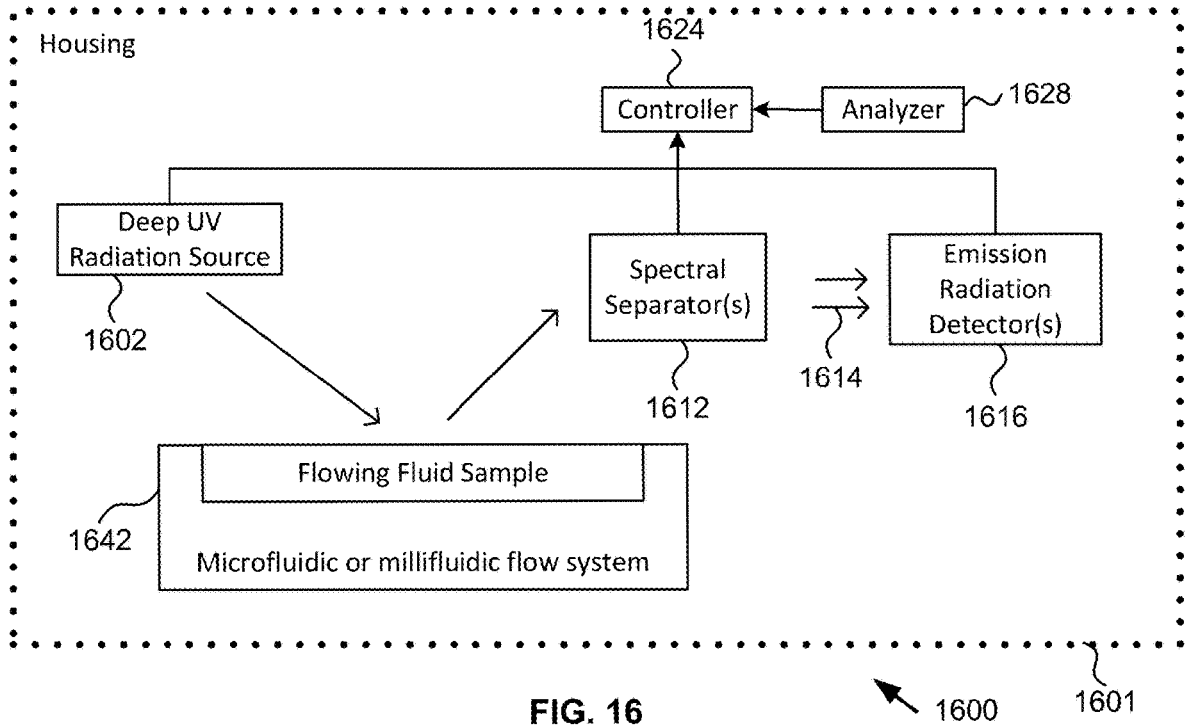
FIG. 16 provides a schematic representation of a system according to a sixteenth embodiment of the invention that is similar to that of FIG. 9 with the exception that in the system, the stage that moves the sample location relative to a fixed exposure location is replaced with components or modules that provide for a flow of a sample past a fixed exposure location wherein the spatial relationship between individual measurements is based on a combination of the flow rate and time between measurements.

FIG. 16 provides a schematic representation of a system according to a sixteenth embodiment of the invention that is similar to that of FIG. 9 with the exception that the stage that moves the sample location relative to a fixed exposure location is replaced with components or modules 1642 that provide for a flow of sample material past a fixed exposure location wherein the spatial relationship between individual measurements is based on a combination of the flow rate and time between measurements. Similar components of FIGS. 16 and 15 are provided with similar reference numbers, but FIG. 15 uses numbers in the 1500 series while FIG. 16 uses numbers in the 1600 series. Numerous alternatives to the embodiment of FIG. 16 are possible and include those noted for FIGS. 4-15 as well as those noted for the other embodiments set forth herein, mutatis mutandis, so long as those variations do not completely remove the functionality or all the uniqueness of the embodiment of FIG. 16. Some variations may include, for example: (1) locating the sample in a capillary tube and allowing capillary force to drive a flow of the fluid, (2) locating the sample in a tube and using vacuum, pneumatic or hydraulic forces to drive a flow of the fluid through at least a portion of the tube, e.g. by heating or cooling one or both ends of the tube or of a reservoir positioned on either side of the sample such that a pressure differential is created that produces a sufficient driving force to cause a flow of the sample material past an exposure location, (3) locating a sample in the tube and using peristaltic pumping to cause a flow of the sample past an exposure location, (4) locating a sample in a tube and using a movable piston to push or pull the sample past an exposure location where the piston may be moved by magnetic force, other non-contact force, coupling to a driving shaft, pressure, or the like. In some variations, the tube or flow channel may be, for example: (1) open on both ends, (2) closed on one end, (3) closed on both ends, (4) formed in a closed loop with sample material filing the vast majority of the loop, (5) formed in a closed loop with sample material filing a relatively small portion of the tube, or (6) formed in a closed loop with sample portions separated by movement markers (i.e. markers that can be detected from which a flow rate can be determined or confirmed) that move with the flow of the sample material. Numerous other variation possibilities exist and will be apparent to those of skill in the art.

Figure 17:
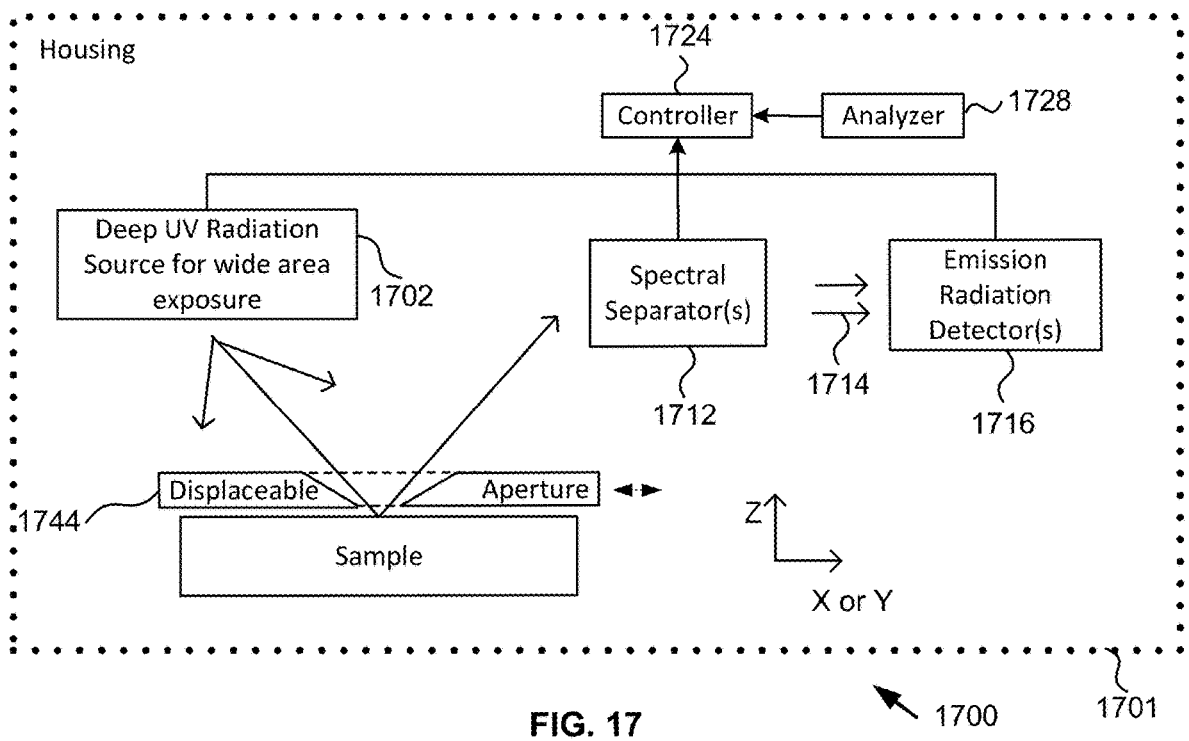
FIG. 17 provides a schematic representation of a system according to a seventeenth embodiment of the invention that is similar to that of FIG. 9 with the exception that in the system, the stage that moves the sample location relative to a fixed exposure location is replaced with a displaceable or movable aperture that allows excitation radiation to strike different locations of a sample and thus produce respective emission radiation from those different locations wherein the spatial relationships between locations is determined by the amount of aperture displacement between detections.

FIG. 17 provides a schematic representation of a system according to a seventeenth embodiment of the invention that is similar to that of FIG. 9 but using a relatively wide area exposure source 1702 with the other exception involving the replacement of the stage that moves the sample location relative to a fixed exposure location is replaced with a displaceable or movable aperture 1744 that allows excitation radiation to strike different locations of a sample and allows respective emission radiation from those different locations to reach a detector or detector focusing optics. The spatial relationships between locations are determined by the amount of aperture displacement between detections. The movable aperture includes a surrounding shield that inhibits or minimizes radiation not traveling along the aperture path from reaching the sample. Similar components of FIGS. 17 and 16 are provided with similar reference numbers, but FIG. 16 uses numbers in the 1600 series while FIG. 17 uses numbers in the 1700 series. Numerous alternatives to the embodiment of FIG. 17 are possible and include those noted for FIGS. 4-16 as well as those noted for the other embodiments set forth herein, mutatis mutandis, so long as those variations do not completely remove the functionality or all the uniqueness of the embodiment of FIG. 17. In some variations, for example: (1) shielding around the aperture may be coated with an absorber or other anti-reflection material to inhibit or minimize reflected excitation radiation from reaching emission detection optics, (2) some emission detection optical components (e.g. windows, lenses, or the like) may be provided with filters or selective transmission features that inhibit or minimize the amount of excitation radiation that can reach the at least one detector, and/or (3) the shielding around the aperture may not block excitation radiation from reaching the sample when an impact location of such radiation is removed from an intended excitation location particularly when emission radiation coming from such peripheral locations is inhibited from reaching a detector or focusing optics for the detector. In some embodiments, the aperture may be displaceable in a single lateral dimension (e.g., X or Y, R or θ) while in others, it may be displaceable in multiple directions (e.g., including two or more X, Y, and Z, or R, θ, and Z).

Figure 18:
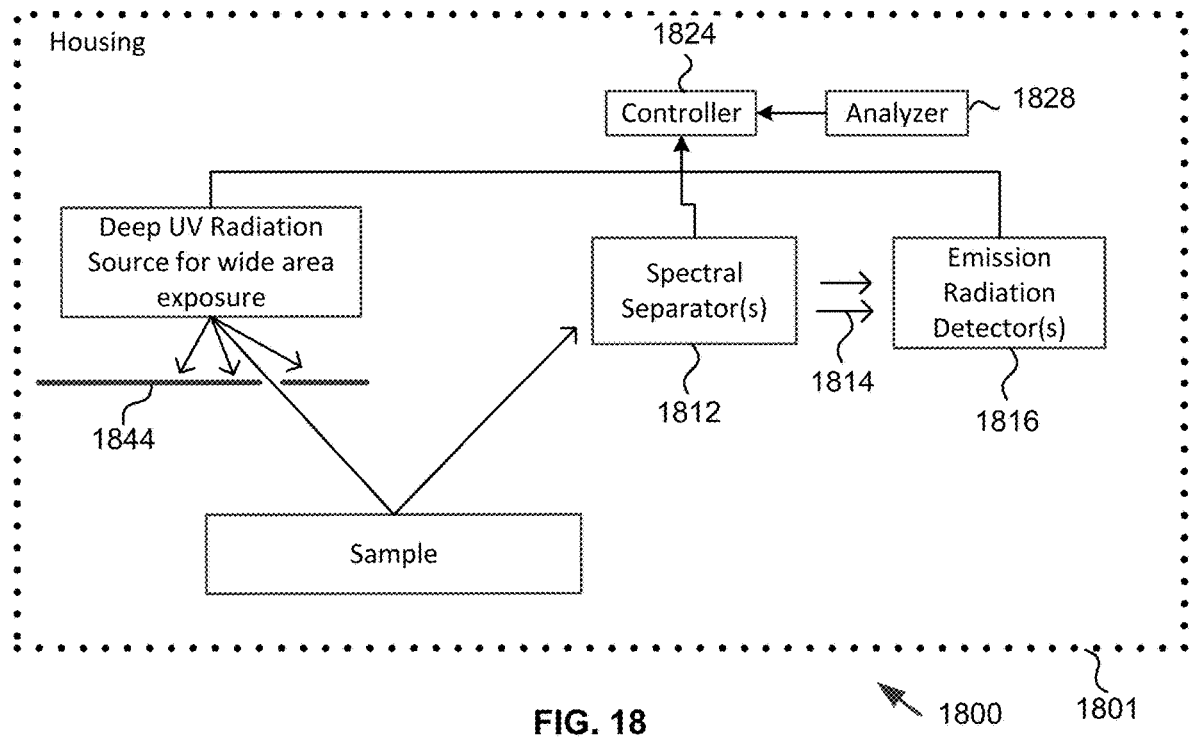
FIG. 18 provides a schematic representation of a system according to an eighteenth embodiment of the invention that is similar to that of FIG. 9 with the exception that in the system, the stage that moves the sample location relative to a fixed exposure location is replaced with a displaceable or movable aperture that allows broad area excitation radiation to be provided by a source while only allowing a portion of such radiation to strike a sample at a controllable location such that only emission radiation from a small but movable area of the sample reaches the at least one detector at any given time such that emission radiation from different sample locations can be serially detected.

FIG. 18 provides a schematic representation of a system according to an eighteenth embodiment of the invention that is similar to that of FIG. 17 with the exception that the displaceable aperture 1844 does not block emission radiation but only excitation radiation. The movable aperture includes a surrounding shield that inhibits or minimizes radiation not traveling along the aperture path from reaching the sample. Similar components of FIGS. 18 and 17 are provided with similar reference numbers, but FIG. 17 uses numbers in the 1700 series while FIG. 18 uses numbers in the 1800 series. Numerous alternatives to the embodiment of FIG. 18 are possible and include those noted for FIGS. 4-17 as well as those noted for the other embodiments set forth herein, mutatis mutandis, so long as those variations do not completely remove the functionality or all the uniqueness of the embodiment of FIG. 18. In some variations, shielding around the aperture may not block excitation radiation from reaching the sample when an impact location of such radiation is removed from an intended excitation location particularly when emission radiation coming from such peripheral locations is inhibited from reaching a detector or focusing optics for the detector. In some embodiments, the aperture may be displaceable in a single lateral dimension (e.g., X or Y, R or θ) while in others, it may be displaceable in multiple directions (e.g., including two or more X, Y, and Z, or R, θ, and Z).

Figure 19:
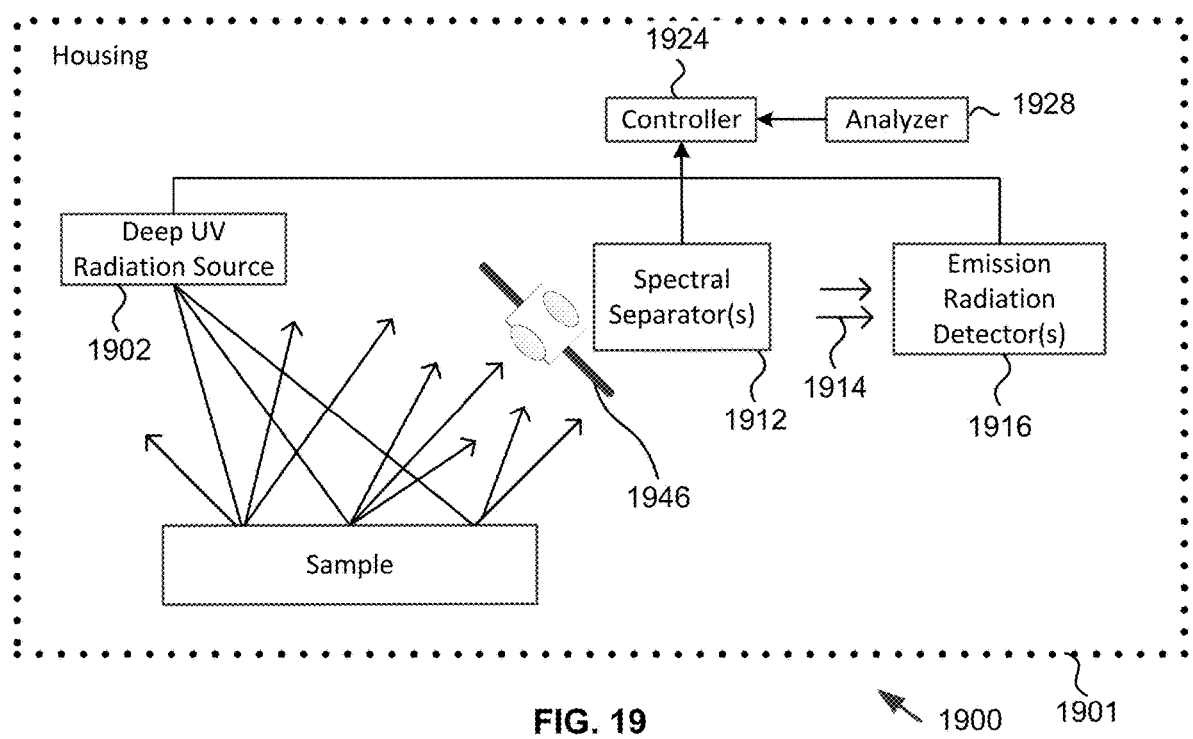
FIG. 19 provides a schematic representation of a system according to a nineteenth embodiment of the invention that is similar to that of FIG. 9 with the exception that in the system, the stage that moves the sample location relative to a fixed exposure location is replaced with a displaceable or movable aperture that allows broad area excitation radiation to strike a sample while allowing only emission radiation from a small but movable area of the sample to reach the at least one detector such that emission radiation from different sample locations can be detected.

FIG. 19 provides a schematic representation of a system according to an nineteenth embodiment of the invention that is similar to that of FIGS. 17 and 18 with the exception that in the system, the displaceable aperture that blocked excitation radiation of FIGS. 17 and 18 is replaced with a displaceable and/or tiltable and/or focusable aperture and lens system 1946 that allows broad area excitation radiation to strike a sample while allowing only emission radiation from a small but movable area of the sample to effectively reach the at least one detector such that emission radiation from different sample locations can be detected. Similar components of FIGS. 19 and 18 are provided with similar reference numbers, but FIG. 18 uses numbers in the 1800 series while FIG. 19 uses numbers in the 1900 series. Numerous alternatives to the embodiment of FIG. 19 are possible and include those noted for FIGS. 4-18 as well as those noted for the other embodiments set forth herein, mutatis mutandis, so long as those variations do not completely remove the functionality or all the uniqueness of the embodiment of FIG. 19. As with the embodiments of FIGS. 17 and 18, the lens system and aperture of FIG. 19 are preferably controlled by the controller in conjunction with control of detection timing and possibly in conjunction with production or impingement of excitation radiation.

Figure 20:
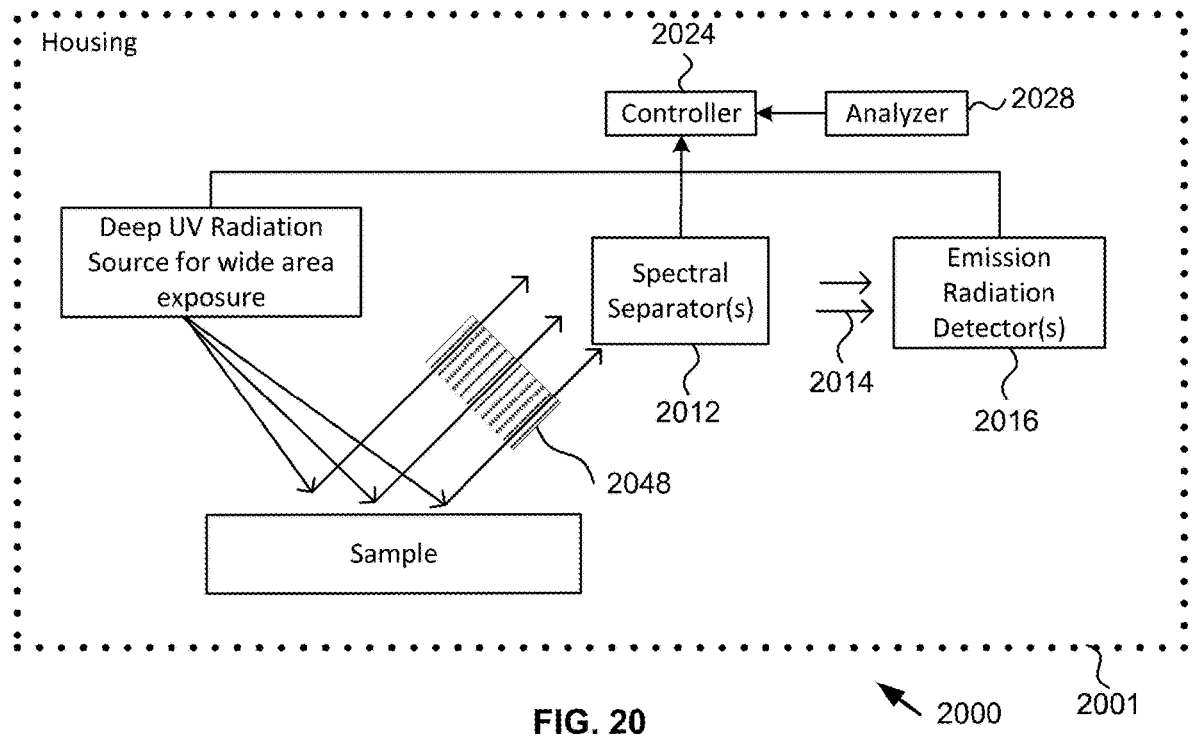
FIG. 20 provides a schematic representation of a system according to a twentieth embodiment of the invention that is similar to that of FIG. 9 with the exception that in the system, the stage that moves the sample location relative to a fixed exposure location is replaced with a plurality of emission detection paths that provide emission radiation from a plurality of differentiable sample locations to be detected in parallel or in a serial manner.

FIG. 20 provides a schematic representation of a system according to a twentieth embodiment of the invention that is similar to that of FIG. 19 with the exception that in the system, the aperture and lens system 1946 that controls what emission radiation reaches the detector is replaced with a spatial filter or optical system 2048 that allows (1) a plurality of emission detection paths that provide emission radiation from a plurality of differentiable sample locations to be detected in parallel or in a serial manner, or (2) a plurality of potential emission paths where the angle can be adjusted so that emission radiation projected within a narrow solid angular range can reach a detector wherein tilt of the spatial filter is set to pass radiation emitted from a position on the sample that is to be analyzed. Similar components of FIGS. 20 and 19 are provided with similar reference numbers, but FIG. 19 uses numbers in the 1900 series while FIG. 20 uses numbers in the 2000 series. Numerous alternatives to the embodiment of FIG. 20 are possible and include those noted for FIGS. 4-19 as well as those noted for the other embodiments set forth herein, mutatis mutandis, so long as those variations do not completely remove the functionality or all the uniqueness of the embodiment of FIG. 20. The tilt angle of the spatial filter or optical system 2048 (e.g., passage array) is preferably controlled by the controller in conjunction with control of detection timing and possibly in conjunction with production of impinging excitation radiation. Though the embodiments of FIGS. 4-20 provide different system embodiments for use in determining biohazard signature presence in complex samples, numerous other system embodiments are possible and include, for example, hybrid systems that incorporate various aspects of the system features from two or more of embodiments of the fourth to twentieth embodiments. Similarly, other embodiments are possible that add component or method features to one or more of the embodiments, or hybrid embodiments, of FIGS. 4-20 by incorporation of the method features of the first to third embodiments of FIGS. 1-3, and their variations, and/or features of the methods and systems set forth in the analytical instruments and methods incorporated herein by reference.

Figure 21:
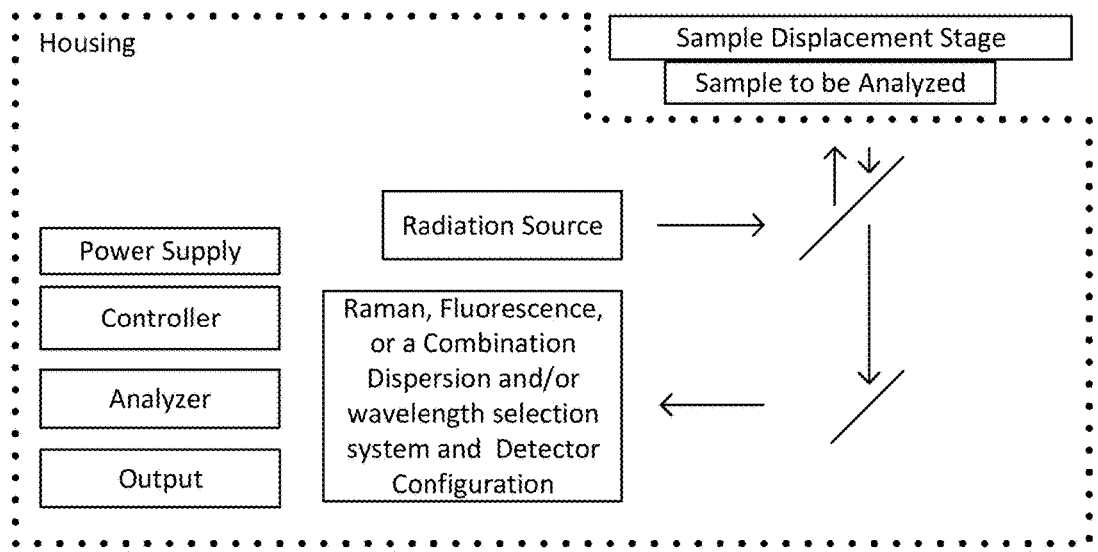
FIG. 21 provides a block diagram of components of a chemical analysis system according to a twenty-first embodiment of the invention wherein a single detection path is provided from the sample up to a dispersion or wavelength specific selection and detection system which allows distinct wavelength bands of Raman and/or fluorescence emission radiation to be read.

FIGS. 21-24 illustrate additional system variations that may be used in embodiments of the present invention. FIG. 21 provides a block diagram of components of a chemical analysis system according to a twenty-first embodiment of the invention wherein a single detection path is provided from the sample up to a dispersion or wavelength specific selection and detection system which allows distinct wavelength bands of Raman and/or fluorescence emission radiation to be read.

Figure 22:
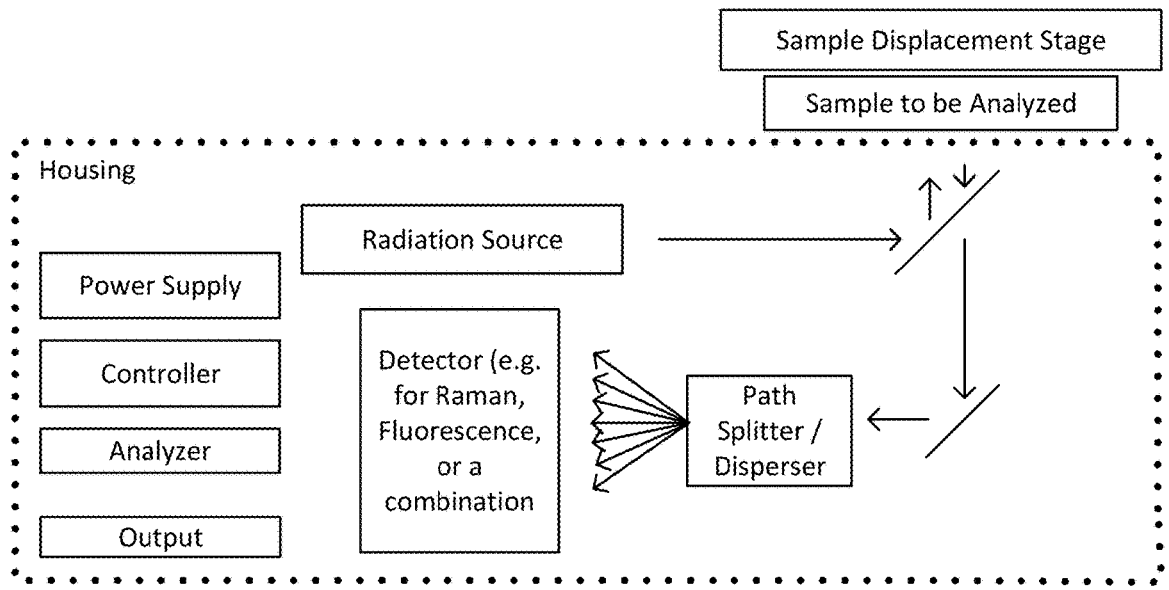
FIG. 22 provides a block diagram of components of a chemical analysis system according to a twenty-second embodiment of the invention wherein a single detection path is provided from the sample up to a dispersion/path splitting element or system from which separate bands of emission radiation follow different detection paths to a detector system which provides for distinct wavelength bands to be detected for different wavelengths of Raman and fluorescence emission radiation.

FIG. 22 provides a block diagram of components of a chemical analysis system according to a twenty-second embodiment of the invention wherein a single detection path is provided from the sample up to a dispersion/path splitting element or system from which separate bands of emission radiation follow different detection paths to a detector system which provides for distinct wavelength bands to be detected for different wavelengths of Raman and fluorescence emission radiation.

Figure 23:
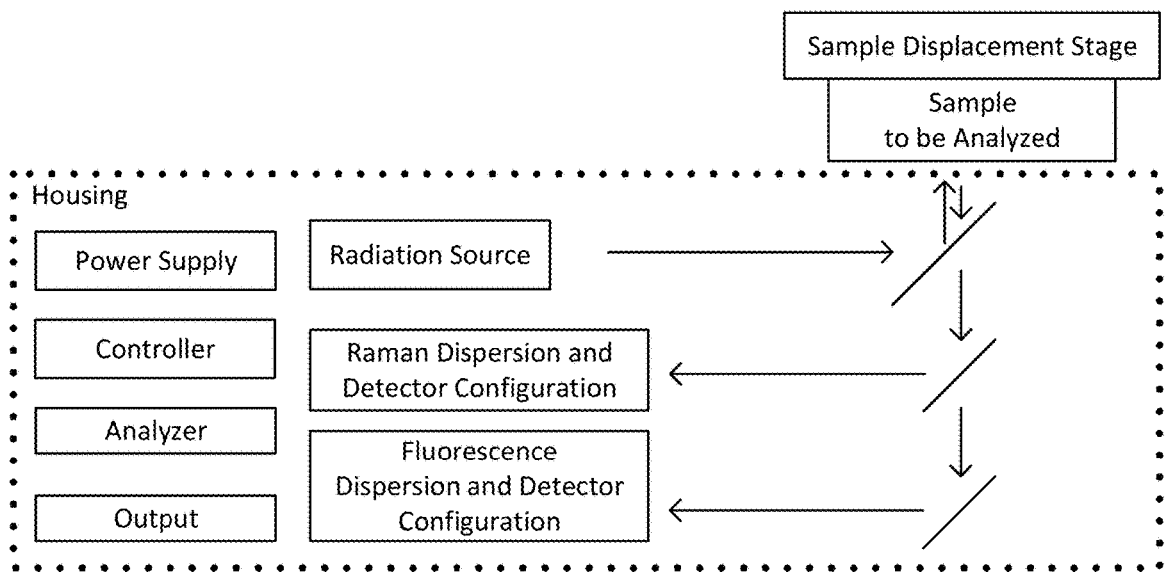
FIG. 23 provides a block diagram of components of a chemical analysis system according to a twenty-third embodiment of the invention wherein a detection path is divided into two separate paths with one going to a Raman dispersion and detection configuration and the other going to a fluorescence dispersion and detector system which allow distinct wavelength bands to be detected for different wavelengths of Raman and fluorescence emission radiation.

FIG. 23 provides a block diagram of components of a chemical analysis system according to a twenty-third embodiment of the invention wherein a detection path is divided into two separate paths with one going to a Raman dispersion and detection configuration and the other going to a fluorescence dispersion and detector system which allow distinct wavelength bands to be detected for different wavelengths of Raman and fluorescence emission radiation.

Figure 24:
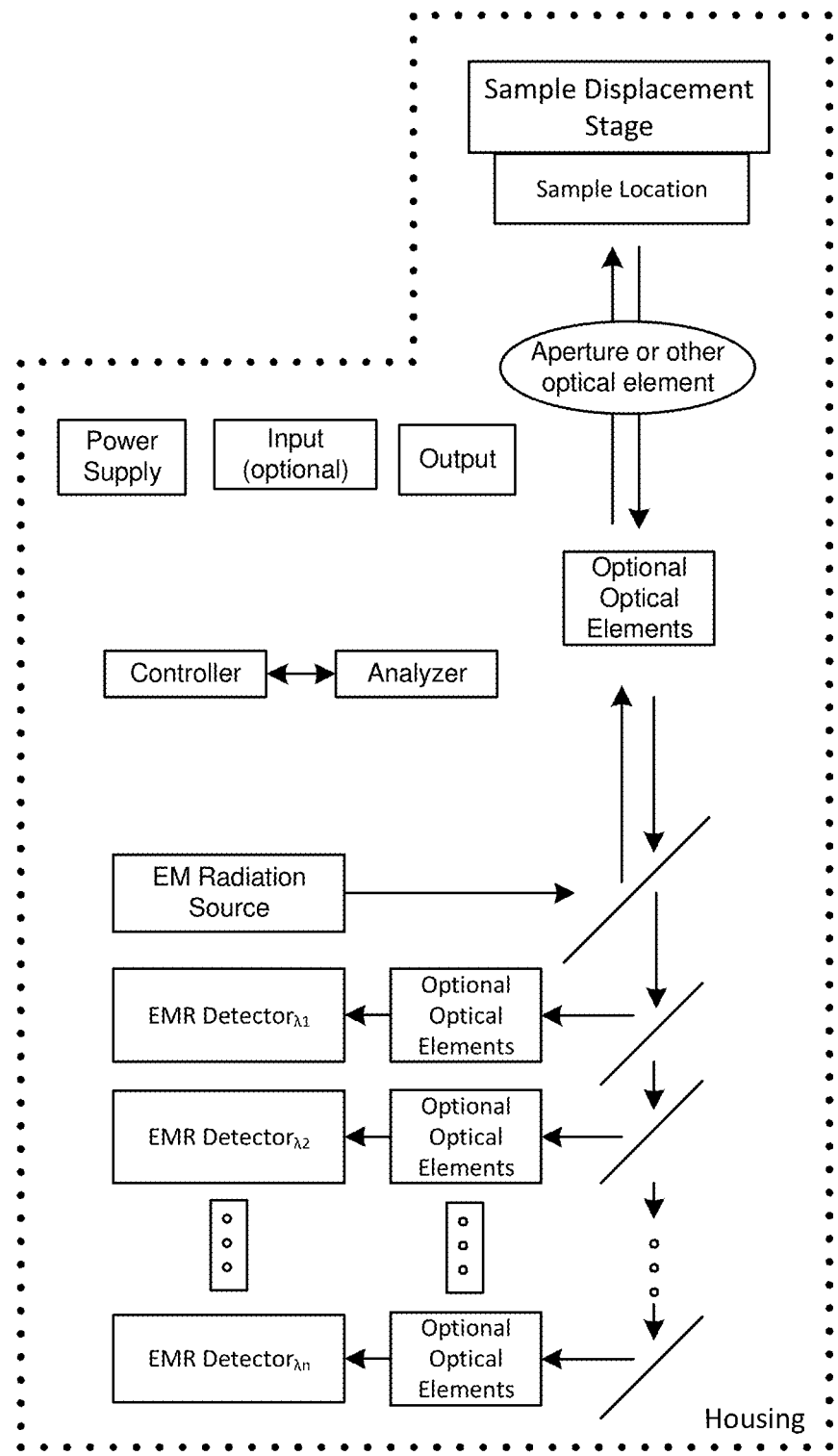
FIG. 24 provides a block diagram of components of a chemical analysis system according to a twenty-fourth embodiment of the invention wherein a single detection path is divided into a plurality of distinct detection paths wherein each distinct detection path provides emission radiation to a detector element (which may include a single detector or multiple detectors) wherein the emission radiation reaching each of the detector elements may or may not undergo further wavelength dispersion or separation to provide additional wavelength band detection.

FIG. 24 provides a block diagram of components of a chemical analysis system according to a twenty-fourth embodiment of the invention wherein a single detection path is divided into a plurality of distinct detection paths wherein each provides emission radiation to a detector element (which may include a single detector or multiple detectors) wherein the emission radiation reaching each of the detector elements may or may not undergo further wavelength dispersion or separation to provide additional wavelength band detection. In some embodiments, the different paths and detector elements may provide detection of different types of emission radiation such as Rayleigh, Raman, fluorescence, and/or phosphorescence, they may provide different band regions for a single type of emission radiation, and/or they may provide bands having selected widths or having varying widths that are considered important in distinguishing different materials so as to provide enhanced operational performance, enhancing analysis speed, reduced system cost, or material differentiation capability.

Figure 26:
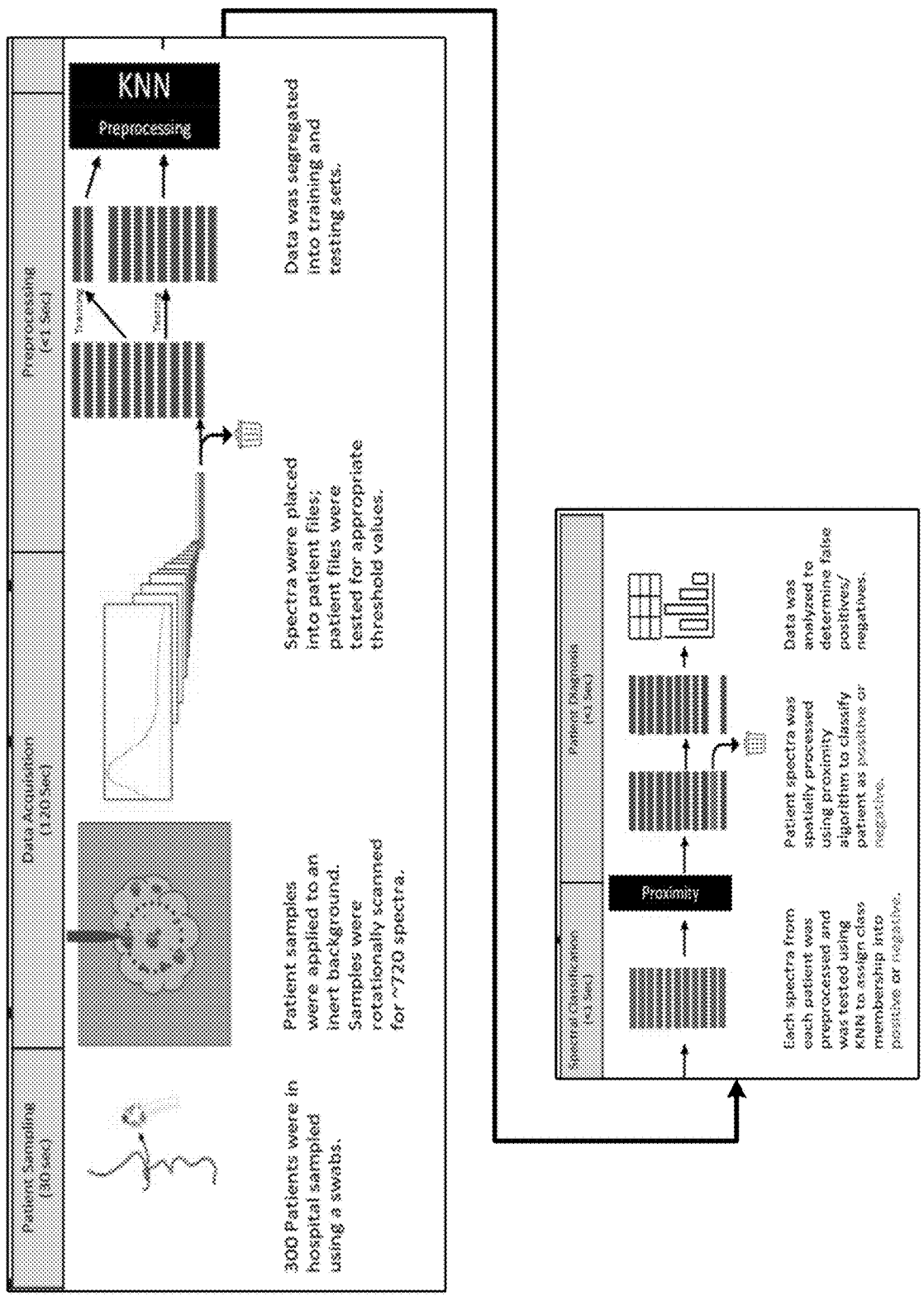
FIG. 26 illustrates a process used in a pilot study involving the use of spectroscopic methods of an embodiment invention for identifying SARS-CoV-2/COVID-19 in patient samples.

FIGS. 25-28 provide illustrations of a system (FIG. 25), a training and testing method that has been put to use in a pilot study to identify samples with SARS-CoV-2 or COVID-19 signatures (FIG. 26), an associated method for testing samples of unknown biohazard signature presence (FIG. 27), and the results of the pilot study (FIG. 28) of FIG. 26.

FIG. 25 provides a schematic illustration of a system according to a twenty-fifth embodiment of invention illustrating in more detail example optical components and relationships that may be used in some implementations of system embodiments.

FIG. 26 illustrates a process used in a pilot study where patients were sampled for SARS-CoV-2/COVID-19 with the samples analyzed by RT-PCR to determine whether the samples were negative or positive for the SARS-CoV-2 virus and its consequences (i.e. whether or not they contained a signature of the presence of the virus or its resulting infection, e.g. COVID-19) and with each sample scanned at offset locations to produce 720 spectra. The data was tested for appropriate threshold values and was segregated into training and testing sets. The data was processed to train and test a KNN algorithm wherein class membership for each spectra of the test set was assigned as positive or negative. The classified location data was then subjected to a proximity algorithm to classify each sample as a whole, as being positive or negative, and the resulting conclusion was compared to the RT-PCR data to determine false positives and negatives.

Figure 27:
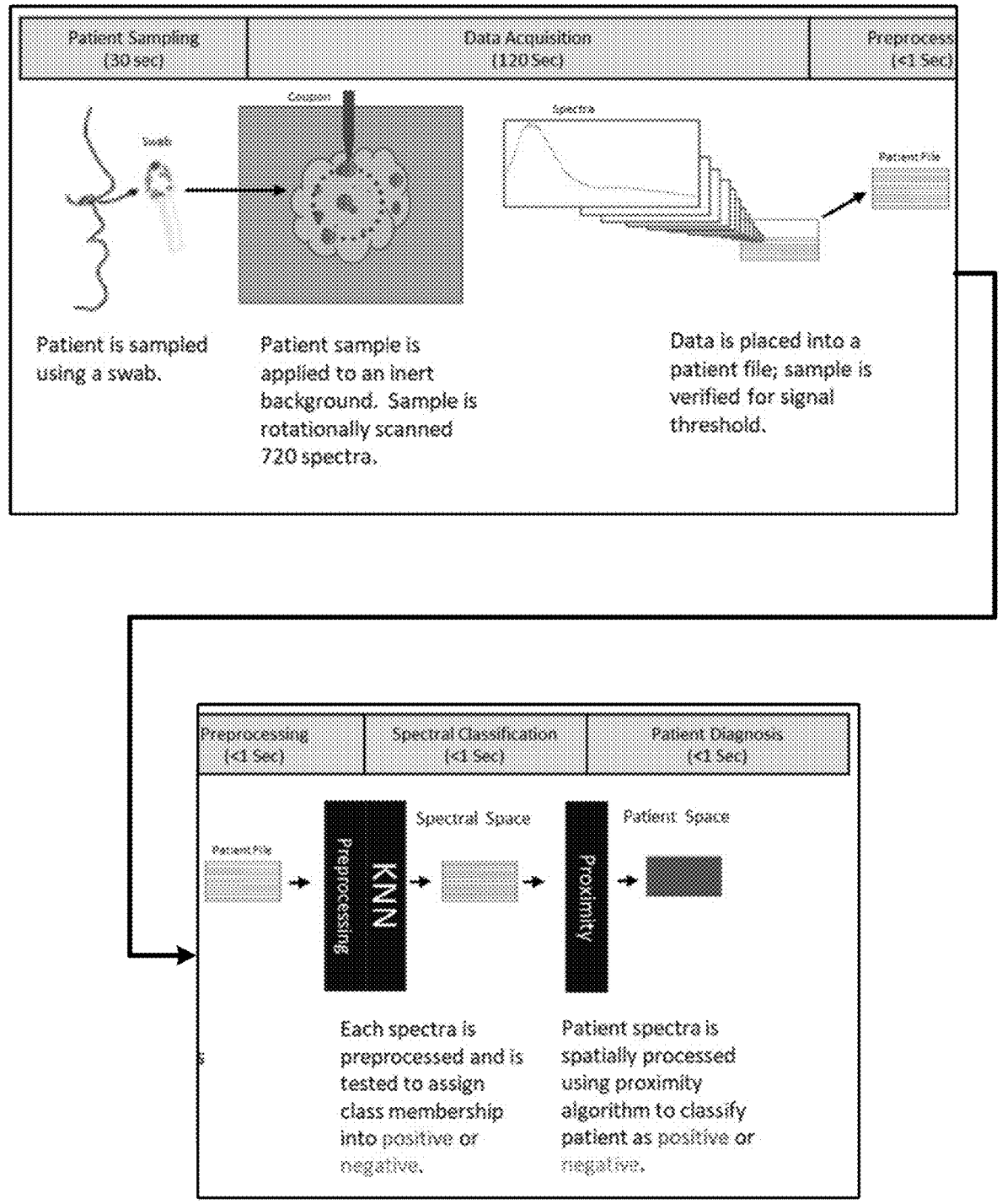
FIG. 27 illustrates how the process of FIG. 26 can be applied to samples with unknown biohazard signature status to provide a biohazard signature status conclusion.

FIG. 27 illustrates how the process of FIG. 26 can be applied to samples with unknown biohazard signature status to provide a biohazard signature status conclusion.

The study used a deep UV instrument configured for both autofluorescence spectroscopy and spatial scanning of samples taken from patients. The instrument was used to detect analytes in their natural state, taken directly from a patient with no sample processing other than smearing the collected material onto a coupon. In the study, the clinical samples were taken by smearing material accumulated using nasopharyngeal swabs onto a test coupon which was inserted into the instrument and spatially scanned to collect the 720 emission spectra from 720 different locations as the sample was moved in a circular pattern relative to the exposure location in a period of less than 2 minutes. The skill level of the instrument operator was minimal. The instrument was a fully integrated, highly portable, instrument weighing under 30 pounds (~25 pounds) and drawing under 150 watts (~100 W) of electrical power from a line or battery.

The pilot study was performed under an ethics board approved pilot study at the University Hospital Aachen/Germany. Multiple types of samples from 300 individual human patients were collected. Samples included 10 different types of specimens with the majority being of the nasopharyngeal type. The samples were either freshly acquired or collected previously and frozen and preserved using standard preservation methods designed to be used with PCR. Each sample collected included RT-PCR analysis to categorize samples into a positive or negative infection groups.

The samples were introduced immediately to the system or after defrosting of the samples occurred. The instrument exposed the samples to deep-UV laser excitation radiation to induce native fluorescence emission radiation. It was believed that the unique protein constituents in the virus or its resulting effects would enable detection and differentiation from human host cells, microbes, and organics that are present in the sample.

Of the 300 clinical specimens, 230 were sampled using nasopharyngeal swabs with 95 patients identified as positive and 135 patients identified as negative for SARS-CoV-2 by RT PCR. The SARS-CoV-2 positive group (with RT-PCR CT values of 13 to 36) were subdivided into two groups. One subgroup consisted of patients having been hospitalized and were being monitored, while the other subgroup were of new infections from individuals that were symptomatic. Neither the analysis system, nor the analysts, had knowledge of which patients fit into either of the two subgroups.

In the SARS-CoV-2 negative group (determined by RT-PCR), there were also two subgroups of patients. One negative subgroup included patients that were showing COVID-19 symptoms (fever, cough, chills, etc.) and had been in contact with a COVID-19 positive individual. While this subgroup was negative, the individuals were infected by another virus or bacterial infection and thus represented possible interferants to SARS-CoV-2 detection. For example, one patient in this group had a positive PCR test for influenza. The other negative subgroup was composed of members of the hospital staff that were being routinely tested and were asymptomatic. Aside from the influenza positive patient, neither the analysis system, nor the analysts, had knowledge of which patients fit into either of the two subgroups.

The process flow used during the clinical study is illustrated in FIG. 26, where total time from beginning of the process to final positive/negative result was less than 3 minutes (with future implementations targeting under 1 minute). The method used employed manual sample taking from a patient and deposition onto an untreated metal coupon. It is believed that with more automation, it may be possible to improve the sample rate per instrument to more than 60 tests per hour.

Prior to any spectral analysis occurring, a threshold was set in the spectral data for each patient at a signal-to-noise value of 7:1. This step was intended to eliminate random results. These data sets were then normalized to their maximum emission values.

The patient populations were split into positive and negative data sets as determined by RT-PCR. The positive and negative patients were then split via a randomization process where 5% of the patients were used to define a Positive and a Negative class and 95% were used as "unknowns".

A patient's positive or negative status (i.e. the conclusion from a sample overall) was dependent on two parameters: (1) the distance of each spectrum of a patient to the Positive or Negative class via k-Nearest Neighbors method, and (2) whether similarly classified spectra were spatially associated (spatial nearest neighbors). The KNN analysis with a K of 1 was used to classify each spectrum of "unknowns" based on the distance to the defined Positive and Negative spectral classes. The results of the KNN analysis were then processed through a spatial filter such that only spatially connected, similarly classified (i.e., positive) spectra was the basis for determining a positive result for a patient while a lack of such spatial connectedness was the basis for determining a negative result for a patient.

The results of the pilot study showed for the 230 nasopharyngeal samples a sensitivity of 96% and a specificity of 97%.

Figure 28:
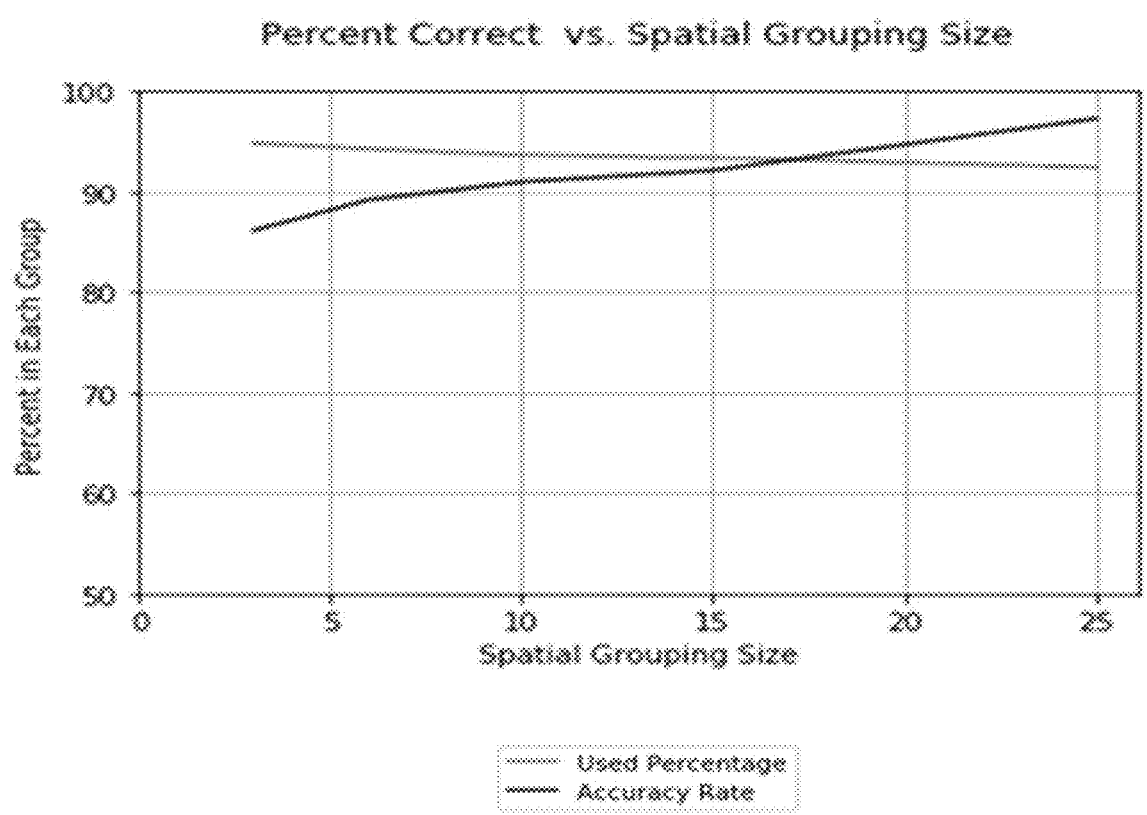
FIG. 28 provides an illustration of the results of the pilot study of FIG. 26.

FIG. 28 shows the effect of spatial group size on the positive and negative accuracy of test conclusions as well as the unused percentage of patient data resulting from changes in spatial group size. A number of the patients' data were not used in the analysis, primarily due to poor SNR<7:1, however some additional patient data were removed as a result of the spatial filtering method and particularly as a result of the number of neighboring positive classified spectra that needed to be grouped in order to categorize the sample wherein sample locations with poor SNR would result in indeterminate results as opposed to a positive or negative result which became more pronounced as the required proximity grouping size became larger. In particular, as the spatial group size for a positive conclusion transitioned from 3 locations to 25 locations the percentage of samples that could give a definite result dropped from about 95% or 96% to about 92%. This effect is shown in FIG. 28 along with a showing that the accuracy rate in the analysis went up as the required grouping size increased. In particular, as the grouping size went from 3 locations to 25 locations, the accuracy level increased from about 86% to about 97%.

Although the above example focused on SARS-CoV-2/COVID-19 detection, the same method is applicable to other microbial or biohazard samples, whether read in situ or in vitro, whether from clinical and environmental surfaces, and whether from a surface, water, or air.

Final Comments

Though various embodiments of the invention have been set forth above as methods, apparatus, and systems, numerous variations are possible and will be apparent to those of skill the art upon review of the teaching herein. Other embodiments may be obtained by using various implementations of methods to define apparatus and systems features. Other embodiment variations are possible by taking functionality provided by selected apparatus and system components and features to define additional steps or operations for method embodiments. Other method embodiments may remove certain steps or operations or change the order of steps or operations so long as such changes do completely eliminate the functionality of the methods. Other methods may take one or more steps or operations and divide them into multiple steps or operations with intermediate steps or operations inserted therebetween. In some cases, some steps or operations may be merged into single steps or operations. Similarly, apparatus and system elements and features may be repositioned, eliminated, or other components added in. In some embodiments, control and analysis steps may be implemented as programs stored in memory and operating under control of a microprocessor, microcontroller, or other logic circuit or control device (e.g., running in a multipurpose computer or dedicated computer system). Other embodiments may implement control and analysis systems in hardware. Programs stored in memory may be limited to programmer defined operations or functionalities or they may include some functionalities, particularly in the form of analysis, determination, classification, or characterization functions that are implemented via trained artificial intelligence or machined learning algorithms.

The biohazard or pathogen signature detection methods set forth herein and/or used by the systems set forth herein may be implemented without use of AI or ML methods or they may be implemented via limited use of AI or ML methods or extensive use of such methods. AI or ML algorithms may be implemented to determine the best set of parameters to use based on a limited set of algorithm variations, e.g., to determine the best value of K to use in a KNN algorithm, the optimum threshold criteria or rejection levels to use when distinguishing or separating useful locations from unusable locations, or to select the optimal spatial correlations to use in making a final conclusion concerning biohazard or pathogen presence or non-presence. In other embodiments, more elaborate AI or ML methods may be used in the hunt for reliable correlations. Implemented programs may have their algorithms and associated parameters set by the AI or ML results directly or once discovered using AI or ML the algorithms and associated parameters may be implemented using definitive code written by a human programmer. In using AI or ML algorithms to find optimized parameters, a single target criteria may be used, e.g. (1) minimized false negative readings, (2) minimized false positive readings, (3) minimized sample rejection, (4) minimized system processing time, (5) maximization of sample types that can be processed successively, (6) minimization of system input needed about particular samples to provide results meeting minimum acceptable criteria, or (7) use of parameters optimized for the type of sample that is being analyzed. In other implementations, optimization of multiple target criteria may be used where each target criteria may be given equal weight or certain criteria may be given more importance than others and where minimum acceptable target criteria, or a criterion for each type of target, may be independently set. In some implementations, once essential criteria have been met, e.g. level of false positives or level of false negatives, algorithms and parameters may be considered fully defined while in other implementations, further analysis may be performed to further enhance one or more of the essential criteria or to improve results for other less essential criteria (but none the less important criteria), e.g., minimization of samples that produce indeterminate results, reduction in system operating time, or improvement in results coming from different types of samples, or from different type of sample sources. In some AI or ML implementations, the algorithms, variables, and/or parameters specifically noted herein may form the primary basis for such AI or ML investigations and trainings while in other implementations, other algorithms, variables, and/or parameters may be used in such investigations and trainings.

Though various portions of this specification have been provided with headers, it is not intended that the headers be used to limit the application of teachings found in one portion of the specification from applying to other portions of the specification. For example, alternatives acknowledged in association with one embodiment are intended to apply to all embodiments to the extent that the features of the different embodiments make such application functional and do not otherwise contradict or remove all benefits of the adopted embodiment. Various other embodiments of the present invention exist. Some of these embodiments may be based on a combination of the teachings set forth herein with various teachings incorporated herein by reference.

It is intended that the aspects of the invention set forth herein represent independent invention descriptions which Applicant contemplates as full and complete invention descriptions that Applicant believes may be set forth as independent claims without need of importing additional limitations or elements, from other embodiments or aspects set forth herein, for interpretation or clarification other than when explicitly set forth in such independent claims once written. It is also understood that any variations of the aspects set forth herein represent individual and separate features that may form separate independent claims, be individually added to independent claims, or added as dependent claims to further define an invention being claimed by those respective dependent claims should they be written.

In view of the teachings herein, many further embodiments, alternatives in design and uses of the embodiments of the instant invention will be apparent to those of skill in the art. As such, it is not intended that the invention be limited to the illustrative embodiments, alternatives, and uses described above but instead that it be solely limited by the claims presented hereafter, subsequently amended, or subsequently set forth in an application that claims priority to this application. In view of the teachings herein, many further embodiments, alternatives in design and uses of the instant invention will be apparent to those of skill in the art.

We claim:

1. A method for identifying presence of at least one of a SARS-CoV2 or a COVID-19 biohazard signature in a sample, comprising:
   (a) exposing a sample to deep UV excitation radiation having a wavelength and reading resulting native fluorescence emission radiation in a plurality of wavelength bands from each of a plurality of locations on the sample, wherein individual locations are exposed and read to produce emission readings, and then followed by movement of the sample relative to an exposure/ emission location in preparation for reading a subsequent location, wherein the wavelength is selected from the group consisting of (i) below 300 nm, (ii) below 275 nm, and (iii) below 250 nm, wherein the plurality of wavelength bands are selected from the group consisting of (i) more than 10 bands, (ii) more than 30 bands, (iii) more than 60 bands, (iv) more than 120 bands, more than 200 bands, (v) more than 400 bands, (vi) more than 600 bands, and (vii) more than 800 bands, and wherein the plurality of locations on the sample is selected from the group consisting of (i) more than 200 locations, (ii) more than 350 locations, (iii) more than 500 locations, and (iv) more than 650 locations;

(b) on a location-by-location basis, performing a first level analysis to determine which locations provide emission radiation that meets signal threshold requirements by exceeding background noise by a factor selected from the group consisting of (i) at least 3, (ii) at least 5, and (iii) at least 7;

(c) for each emission radiation location meeting signal threshold requirements, performing a second level membership analysis to assign a class membership to individual locations which have readings indicative of potential relevance to at least one of a SARS-CoV2 or a COVID-19 biohazard signature presence, wherein the second level membership analysis comprises use of a KNN algorithm, with a K value selected from the group consisting of: (i) at least one, (ii) at least three, and (iii) at least five, and wherein the class membership is assigned on a location-by-location basis using at least two categories comprising: (1) positive membership for locations wherein emission radiation for each such location is more closely aligned to biohazard signature presence than to biohazard signature non-presence, and (2) negative membership for locations wherein emission radiation for each such location is closer to biohazard signature non-presence than to biohazard signature presence; and (d) performing at least one additional level of analysis involving spatial relationships between a plurality of locations having positive membership wherein at least one of a SARS-CoV2 or a COVID-19 biohazard signature presence for the sample is determined when the sample comprises a number N of neighboring locations having positive membership with no more than M intervening locations having negative membership, wherein N is selected from the group consisting of: (i) at least 3, (ii) at least 7, (iii) at least 11, (iv) at least 15, and (v) at least 25, and wherein M is selected from the group consisting of: (i) 0, (ii) no more than 1, (iii) no more than 5% of N, (iv) no more than 10% of N, (v) no more than 20% of N, (vi) no more than 30% of N, and (vii) no more than 40% of N.

2. A method for identifying presence of a selected biohazard signature in a sample, comprising:

(a) exposing a sample to excitation radiation and reading resulting emission radiation for a plurality of wavelength bands from each of a plurality of locations on the sample;

(b) on a location-by-location basis, performing a first level analysis to determine which emission radiation readings meet signal threshold requirements relative to background noise readings;

(c) for each location having emission radiation readings meeting signal threshold requirements, performing a second level membership analysis to assign a class membership to individual location readings indicative of potential relevance to biohazard signature presence, wherein positive membership is assigned to locations when the readings for such locations are deemed closer to readings associated with samples known to contain the biohazard signature than to readings associated with samples known not to contain the biohazard signature; and (d) defining at least one minimum threshold spatial grouping criterion for locations with positive membership that is necessary to conclude that the sample is positive for presence of the biohazard signature;

(e) performing at least one additional level of analysis comprising a determination of whether the sample includes positive membership locations that, taken together in conjunction with their relative spatial positions, meet the at least one minimum threshold spatial grouping criterion and if so, determining that the sample is positive for the presence of the biohazard signature, wherein the excitation radiation comprises radiation with wavelength selected from the group consisting of: (1) below 300 nanometers, (2) below 275 nm, and (3) below 250 nm, wherein the emission radiation readings comprise readings of native fluorescence emission radiation, and wherein the at least one minimum threshold spatial grouping criterion comprises use of positive membership for multiple locations and the spatial relationship of those locations.

3. The method of claim 2 wherein negative membership is assigned to locations when the readings for such locations are deemed closer to readings associated with samples known not to contain the biohazard signature than to readings associated with samples known to contain the biohazard signature, wherein the minimum spatial grouping criteria for locations with positive membership is selected from the group consisting of:

(1) a plurality of successive neighboring individual locations have a positive membership wherein the plurality is selected from the group consisting of: (a) at least three, (b) at least five, (c) at least seven, (d) at least ten, and (e) at least fifteen;

(2) at least N % of a plurality of nearest neighbor locations have a positive membership, wherein a number of the plurality is selected from the group consisting of: (a) at least five, (b) at least seven, (c) at least ten, and (d) at least fifteen, and wherein N % is selected from the group consisting of (a) greater than 50%, (b) greater than 65%, (c) greater than 80%, and (d) greater than 90%;

(3) each of a plurality of nearest neighbor locations have a positive membership, with a possible exception that one location intermediate to the plurality may provide a membership determination selected from the group consisting of: (a) an indeterminate membership, and (b) a negative membership, and wherein a number of the plurality is selected from the group consisting of: (a) at least five, (b) at least seven, (c) at least ten, and (d) at least fifteen;

(4) a plurality of K neighboring locations have positive membership, with a possible exception that a number of locations intermediate to the neighboring locations may not have positive membership wherein the number is no less than one but as high as a number, if higher than one, selected form the group consisting of: (a) less than 10% of K having negative membership, (b) less then 20% of K having indeterminant membership, and (c) less than 10% of K having negative membership and less than 20% having indeterminant membership, and wherein the number K is selected from the group consisting of: (a) at least five, (b) at least seven, (c) at least ten, and (d) at least fifteen;

(5) at least M clusters of locations with each cluster having at least N neighboring locations with each such location providing positive membership, wherein M is at least 2 and N is at least 3, and wherein the sum of M and N is at least 10;

(6) at least M out of N locations have positive membership where the N locations are proximate to one another such that each of the N locations is separated from neighboring locations by at least R exposure widths but no more than S exposure widths, wherein M is selected from the group consisting of: (a) at least 3, (b) at least 5, (c) at least 9, (d) at least 15, wherein N is selected from the group consisting of: (a) at least 50, (b) at least 100, (c) at least 200, (d) at least 400, and (e) at least 800, wherein R is selected from the group consisting of: (a) no less than ¼, (b) no less than ½, (c) no less than ¾, (d) no less than 1; and wherein S is selected from the group consisting of: (a) no more than 2, (b) no more than 5, (c) no more than 10, and (d) no more than 20;

(7) a supermajority of N non-overlapping locations have positive membership, wherein the supermajority is selected from the group consisting of: (a) at least ⅔ of N, (b) at least ¾ of N, (c) at least ⅘ of N, (d) at least ⅚ of N, (e) at least 6/7 of N, (f) at least ⅞ of N, (g) at least 8/9 of N, and (h) at least 9/10 of N, and wherein N is selected from the group consisting of: (a) at least 5, (b) at least 7, (c) at least 11, (d) at least 15, and (e) at least 25; and (8) a plurality of at least F out of FF locations have positive membership based on native fluorescence emission detections and a plurality of at least R out of RR locations have positive membership based on Raman emission detections where the R locations are common with respective F locations, wherein (i) F and R are selected from the group consisting of: (a) F is at least 3 and R is at least 2, (b) F is at least 5 and R is at least 3, (c) F is at least 9 and R is at least 7, (d) F is at least 15 and R is at least 11, and wherein (ii) FF and RR are each selected from the group consisting of: (a) at least 20 locations, (b) at least 50 locations, (c) at least 100 locations, (d) at least 200 locations, (e) at least 400 locations, and (f) at least 800 locations.

4. The method of claim 2, wherein element (a) additionally comprises a step between successive sets of exposing and reading that causes relative movement of the exposure location and the sample to expose the plurality of locations selected from the group consisting of: (1) using a movable stage to move a sample relative to sample excitation components and emission radiation detection components when obtaining emission data from different locations of the plurality of locations on the sample, (2) using a movable stage to move components selected from the group consisting of: (i) excitation radiation components and (ii) emission radiation detection components relative to a sample that is held in a fixed position relative to a housing between obtaining emission data from each of the plurality of locations on the sample, (3) using a movable aperture that allows excitation radiation to strike a sample at a single location and emission radiation to reach a detector from such single location and moving the aperture to obtain emission data from each of the plurality of locations on the sample, (4) using a movable aperture that allows excitation radiation to strike a sample at a single location and thus allows only emission radiation from such location to reach a detector at any given time and moving the aperture to obtain emission data from each of the plurality of locations on the sample, (5) using a movable aperture that allows only emission radiation from a single location to reach a detector at any given time and moving the aperture to obtain emission data from each of the plurality of locations on the sample, (6) using a multiple path transmission array in controlling which location on a sample provides emission radiation for detection and moving the transmission array to allow emission radiation from each of the plurality of sample locations to be detected, and (7) using a multiple path transmission array in controlling which location on a sample provides emission radiation for detection and rotating the transmission array to allow emission radiation from each of the plurality of sample locations to be detected.

5. A method for identifying presence of a selected biohazard signature in a complex sample, comprising:

(a) providing excitation radiation onto a portion of a sample, wherein the excitation radiation is provided as a beam from a source within a housing, wherein the beam has a dimension that is smaller than a sample dimension;

(b) receiving emission radiation, from the portion of the sample that received excitation radiation, onto at least one optical element which directs the emission radiation along at least one detection path within the housing;

(c) directing excitation radiation to be incident upon different portions of a sample by relatively moving the beam and the sample;

(d) for each of a plurality of different portions of the sample, detecting a group of emission signals, with each group comprising signals from a plurality of different wavelength bands, using at least one detector located within the housing at a location along the at least one detection path;

(e) for the plurality of groups of emission signals associated with the plurality of different sample portions, distinguishing useful signal groups from unusable signal groups, where useful signal groups are those containing at least one signal having a strength that is greater than a strength of a corresponding background signal by a predefined amount, and wherein each useful signal group is associated with one of the plurality of difference sample portions;

(f) providing both predetermined biohazard indicative signal information and predetermined non-biohazard indicative signal information related to the selected biohazard signature;

(g) producing a biohazard indicative status for each useful signal group based at least in part upon a comparison of emission signal data for that group with the predetermined biohazard indicative signal information and predetermined non-biohazard indicative signal information; and (h) forming a biohazard indicative conclusion based, at least in part, on a combination of (1) biohazard indicative signal information for a plurality of useful signal groups, and (2) relative spacings between the portions of the sample associated with the plurality of useful signal groups having biohazard indicative signal information.

6. The method of claim 5 wherein the excitation radiation comprises radiation with wavelength selected from the group consisting of (1) below 300 nanometers, (2) below 275 nm, and (3) below 250 nm.

7. The method of claim 6 wherein the directing of excitation radiation comprises a method selected from the group consisting of:
(1) operating a stage to move the sample relative to an excitation radiation to provide excitation radiation to different portions of the sample,
(2) moving an aperture that allows excitation radiation to strike a sample at a single location and emission radiation to reach a detector from the single location at a given time and moving the aperture to obtain emission data from the plurality of locations on the sample,
(3) using a movable aperture that allows only emission radiation from a single location to reach a detector at a given time,
(4) a combination of any of at least two of (1)-(3).

8. The method of claim 6 wherein the biohazard comprises a pathogen and the biohazard signature is a pathogen signature.

9. The method of claim 6 wherein the selected biohazard signature is selected from the group consisting of:
(1) a molecular indicator of a biohazard selected from the group consisting of: (i) a virus, (ii) a fungus, (iii) a yeast, (iv) a mold, (v) a bacterium, (vi) a prion, and (vii) a biological toxin;
(2) a molecular indicator of a non-infecting presence of a biohazard, wherein the biohazard is selected from the group consisting of: (i) a virus, (ii) a fungus, (iii) a yeast, (iv) a mold, (v) a bacterium, (vi) a prion, and (vii) a biological toxin;
(3) a molecular indicator of an infecting presence of a biohazard, wherein the biohazard is selected from the group consisting of: (i) a virus, (ii) a fungus, (iii) a yeast, (iv) a mold, (v) a bacterium, (vi) a prion, and (vii) a biological toxin; and
(4) a molecular indicator of a past infecting presence of a biohazard, wherein the biohazard is selected from the group consisting of: (i) a virus, (ii) a fungus, (iii) a yeast, (iv) a mold, (v) a bacterium, (vi) a prion, and (vii) a biological toxin.

10. A method of identifying presence of a selected biohazard signature in a complex sample, comprising:
(a) providing excitation radiation onto a portion of a sample, wherein the excitation radiation is provided as a beam from a source within a housing, wherein the beam has a dimension that is smaller than a sample dimension;
(b) receiving emission radiation, from the portion of the sample that received excitation radiation, onto at least one optical element which directs the emission radiation along at least one detection path within the housing;
(c) directing excitation radiation to be incident upon different portions of a sample by relatively moving the beam and the sample;
(d) for each of a plurality of different portions of the sample, detecting a group of emission signals, with each group comprising signals from a plurality of different wavelength bands, and using at least one detector located within the housing at a location along the at least one detection path;
(e) for the plurality of groups of emission signals associated with the plurality of different sample portions, distinguishing useful signal groups from unusable signal groups, where useful signal groups are those containing at least one signal having a strength that is greater than a strength of a corresponding background signal by a predefined amount, and wherein each useful signal group is associated with one of the plurality of different sample portions;
(f) providing both predetermined biohazard indicative signal information and predetermined non-biohazard indicative signal information related to the selected biohazard signature;
(g) producing a biohazard indicative status for each useful signal group based at least in part upon a comparison of emission signal data for that group with the predetermined biohazard indicative signal information and predetermined non-biohazard indicative signal information; and
(h) forming a biohazard indicative conclusion based, at least in part, on a combination of (1) biohazard indicative signal information for a plurality of useful signal groups, and (2) relative spacings between the portions of the sample associated with the plurality of useful signal groups having biohazard indicative signal information,
wherein the excitation radiation comprises radiation with wavelength selected from the group consisting of: (1) below 300 nanometers, (2) below 275 nm, and (3) below 250 nm,
wherein the selected biohazard signature is selected from the group consisting of:
(1) a molecular indicator of a virus,
(2) a molecular indicator of a non-infecting presence of a virus,
(3) a molecular indicator of an infecting presence of a virus, and
(4) a molecular indicator of a past infecting presence of a virus, and
wherein the selected biohazard is further selected from the group consisting of: (1) a corona virus, (2) SARS-CoV-2, (3) an influenza virus (selected from the group consisting of A, B, C, and D), (4) a hemorrhagic fever virus, and (5) Ebola.

11. The method of claim 10 wherein the excitation radiation is supplied in a form selected from the group consisting of:
(1) CW radiation,
(2) radiation supplied in pulses with durations greater than 100 ns (nanosecond),
(3) radiation supplied in pulses with durations greater than 1 µs (microsecond),
(4) radiation supplied in pulses with durations greater than 10 µs, and
(5) radiation supplied with a power density smaller than that which will cause adiabatic heating damage to the biohazard signature; and
(6) radiation supplied at a power level, over a time, and with a number of repetitions that will not substantially inhibit future detection of the biohazard signature, wherein not substantially inhibiting detection is selected from the group consisting of: (a) not reducing detection by more than 10%, (b) not reducing detection by more than 20%, (c) not reducing detection by more than 50%, (d) not increasing presence of false negative conclusions by more than 1%, (e) not increasing presence of false negative conclusions by more than 2%, (f)

not increasing presence of false negative conclusions by no more 5%, (g) not increasing presence of false negative conclusions by more than 10%, (h) not increasing presence of false negative conclusions by more than 25%; and wherein the source of the UV excitation radiation is selected from the group consisting of:
(1) any radiation source with a wavelength less than 250 nm,
(2) an LED source with a wavelength less than 300 nm,
(3) an LED source with a wavelength less than 275 nm,
(4) an LED source with a wavelength less than 250 nm,
(5) an LD (laser diode) with a wavelength less than 300 nm,
(6) an LD source with a wavelength less than 275 nm,
(7) an LD source with a wavelength less than 250 nm,
(8) a CW laser source with a wavelength less than 300 nm,
(9) a CW laser source with a wavelength less than 275 nm,
(10) a CW laser source with a wavelength less than 250 nm,
(11) a pulsed laser source with a wavelength less than 300 nm,
(12) a pulsed laser source with a wavelength less than 275 nm,
(13) a pulsed laser source with a wavelength less than 250 nm,
(14) an unpolarized ultraviolet source with a wavelength below 300 nm, and
(15) any of (1)-(14) wherein no more than 20% of the excitation radiation is above the indicated wavelength.

12. The method of claim 10 wherein the beam dimension is a width and has a size selected from the group consisting of:
(1) less than 1 mm,
(2) less than 0.5 mm,
(3) less than 0.2 mm,
(4) less than 0.1 mm, and
(5) less than 0.05 mm,
wherein the beam has a maximum width to minimum width ratio at a focal point selected from the group consisting of:
(1) less than 5.0,
(2) less than 2.0,
(3) less than 1.5,
(4) less than 1.25, and
(5) less than 1.1.

13. The method of claim 10, wherein the emission radiation that is detected comprises radiation selected from the group consisting of:
(1) native fluorescence radiation,
(2) Raman radiation,
(3) phosphorescence,
(4) fluorescence decay over time after excitation radiation exposure ceases,
(5) native fluorescence radiation for a plurality of first sample positions with a first spacing followed by further fluorescence emission radiation detection from at least one intermediate position to at least one selected pair of the first sample positions where an initial detection of fluorescence emission radiation provided a result that triggered the further radiation exposure and fluorescence emission radiation detection, and
(6) native fluorescence radiation for a plurality of first sample positions followed by Raman radiation detection at at least one position selected from the group consisting of: (a) at least one of the plurality of first sample positions, and (b) at least one position intermediate to the plurality of first sample positions where initial fluorescence radiation for at least one of the plurality of first sample positions provided a result that triggered a more detailed analysis of the at least one position using Raman radiation.

14. The method of claim 10 wherein the emission radiation comprises native fluorescence radiation wherein the plurality of different wavelength bands for each group of emission signals comprises at least N wavelength bands wherein N is selected from the group consisting of: (1) at least four, (2) at least eight, (3) at least fifteen, (4) at least thirty, (5) at least sixty, (6) at least one-hundred twenty, (7) at least two hundred fifty, (8) at least five hundred, (9) at least one thousand, and (10) at least two thousand.

15. The method of claim 10 wherein the emission radiation is detected with a timing selected from the group consisting of:
(1) during exposure but greater than 1 µs (microsecond) after the initiation of excitation radiation,
(2) during exposure but greater than 5 µs after initiation of the excitation radiation,
(3) during exposure but greater than 10 µs after initiation of the excitation radiation,
(4) during exposure but greater than 20 µs after initiation of the excitation radiation,
(5) greater than 1 µs (microsecond) after the extinction of excitation radiation,
(6) greater than 5 µs after the extinction of excitation radiation,
(7) greater than 10 µs after the extinction of excitation radiation,
(8) greater than 20 µs after the extinction of excitation radiation,
(9) at a set time after initiation of the excitation radiation,
(10) at a plurality of different set times after initiation of the excitation radiation,
(11) at a set time after extinction of the of excitation radiation, and
(12) at a plurality of set times after extinction of the of excitation radiation.

16. The method of claim 10 wherein the predefined amount is a ratio of measured signal strength to background signal selected from the group consisting of: (1) at least three, (2) at least five, (3) at least seven, (4) at least ten, and (5) at least fifteen.

17. The method of claim 10 wherein the predetermined biohazard indicative signal information and non-biohazard indicative signal information is provided in a manner selected from the group consisting of: (1) on a band-by-band basis, and (2) band-by-band ratio basis for a plurality of samples known to contain the biohazard signature and for a plurality of samples known not to contain the biohazard signature wherein the information is provided in a form selected from the group consisting of:
(1) raw band-by-band data for the each of the plurality of samples known to contain and known not to contain the biohazard signature;
(2) normalized band-by-band data for the each of the plurality of samples known to contain and known not to contain the biohazard signature;
(3) a plurality of selected band-to-band ratios for each of the plurality of samples known to contain and known not to contain the biohazard signature;
(4) a band-by-band value taken from normalized data for each group of samples known to contain and known not to contain the biohazard signature, wherein the value is selected from the group consisting of: (a) a mean, (b)

a mode, (c) a median, (d) a mid-point of a range, (e) a midpoint of a range with outliers removed, (f) a low range number with outliers removed, (g) a low range number without outliers removed, (h) a high range number with outliers removed, and (i) a high range number without outliers removed;

(5) the band-by-band value of (4) along with at least one value indicative of range, wherein the at least one value indicative of range is selected from the group consisting of: (a) a standard deviation, (b) a plus range number, (c) a minus range number, (d) both a plus and minus range number, (e) a full range number with outliers removed, (f) a full range number without outliers removed and (g) S standard deviations where S is a number between 1 and 10 inclusive;

(6) a band-by-band low range value and a high range value taken from normalized data with outliers removed;

(7) a band-by-band low range value and a high range value taken from normalized data without outliers removed;

(8) a band-by-band group of equations bridging the normalized emission values for the predetermined known biohazard signature containing and non-biohazard signature containing groups;

(9) a band-by-band group of relationships bridging the normalized emission values for the predetermined known biohazard signature containing and non-biohazard signature containing groups;

(10) a band-by-band set of normalized detection values for each of the groups of predetermined samples known to contain biohazard signatures and known not to contain biohazard signatures wherein the band-by-band set of normalized detection values are closer to the detection values for their respect group than they are to the values for the other group;

(11) a plurality of values for selected band-to-band ratios for each of the predetermined known biohazard and non-biohazard containing groups wherein each of the values is selected from the group consisting of: (a) a mean, (b) a mode, (c) a median, (d) a mid-point of a range, (e) a midpoint of a range with outliers removed, (f) a low range number with outliers removed, (g) a low range number without outliers removed, (h) a high range number with outliers removed, and (i) a high range number without outliers removed;

(12) the plurality of values of (11) along with at least one value indicative of ratio range, wherein the at least one value indicative of ratio range is selected from the group consisting of: (a) a standard deviation, (b) a plus range number, (c) a minus range number, (d) both a plus and minus ratio range number, (e) a full range number with outliers removed, (f) a full range number without outliers removed, and (g) S standard deviations where S is a number between 1 and 10;

(13) a plurality of selected band-to-band ratios providing a low range value and a high range value with outliers removed;

(14) a plurality of selected band-to-band ratios providing a low range value and a high range value without outliers removed;

(15) a plurality of selected band-to-band ratio equations bridging the emission value ratios for the predetermined known biohazard and non-biohazard containing groups;

(16) a plurality of selected band-to-band ratio relationships bridging the emission value ratios for the predetermined known biohazard and non-biohazard containing groups;

(17) a selected band-to-band set of ratio values for each of the groups of predetermined samples known to contain biohazard signatures and known not to contain biohazard signatures;

(18) central values and range related values for each band as obtained from the plurality of samples known to contain biohazard signatures and those known not to contain biohazard signaturesp and

(19) central values and range related values (for each of a plurality of selected band-to-band ratios as obtained from the plurality samples known to contain the biohazard signatures and those known not to contain the biohazard signatures.

18. The method of claim 17 wherein producing a biohazard indicative status for each useful signal group based at least in part upon a comparison of emission signal data for that group with the predetermined biohazard indicative signal information and predetermined non-biohazard indicative signal information is performed on a basis selected from the group consisting of:

(1) for each of at least a selected plurality of the bands, comparing the measured spectral information to those of the samples with known biohazard and non-biohazard indicative signatures and determining if the spectral information of the measured sample is generally closer to that of the samples with known biohazard signatures or to that of the samples with known non-biohazard indicative signatures and labeling the band with a corresponding biohazard status, and then combining the corresponding biohazard status for each selected band to provide a biohazard indicative status for the location;

(2) using a calculated ratio of spectral information associated with each selected band and another band from the measured sample to a corresponding ratio of bands from the samples with known biohazard and known non-biohazard indicative signatures and determining if the ratio of the measured sample is generally closer to that of the samples having the known biohazard signature or the known non-biohazard signature and labeling the band with a corresponding biohazard status, and then combining the corresponding biohazard status for each selected band to provide a biohazard indicative status for the portion;

(3) using a selected artificial intelligence (AI) algorithm that is trained and verified with the information from the samples with known biohazard signature statuses such that when the measured data associated with specific positions on the complex sample undergoes analysis, the trained algorithm produces results that are consistent with training data and meets any requirements associated with limiting false positives and false negatives;

(4) using basis (3) with an AI algorithm including an instance-based algorithm selected from the group consisting of: (a) a K Nearest Neighbor (KNN) algorithm, (b) a Learning Vector Quantization (LVQ) algorithm, (c) a Self-Organizing Map (SOM) analysis, (d) a Locally Weighted Learning (LWL) analysis, and (e) a Support Vector Machines (SVM) analysis;

(5) using basis (3) with an AI algorithm including a dimensionality reduction algorithm, selected from the group consisting of: (a) a Principal Component Analysis (PCA), (b) a Principal Component Regression (PCR), (c) a Partial Least Squares Regression (PLSR), and (d) a Discriminant Analysis (DA); and (6) using basis (3) with an AI algorithm including a regression analysis selected from the group consisting of: (a) an Ordinary Least Squares Regression (OLSR) analysis, (b) a Linear Regression analysis, (c) a Logistic Regression analysis, (d) a Stepwise Regression analysis, (e) a Multivariate Adaptive Regression Splines (MARS) analysis, and (f) a Locally Estimated Scatterplot Smoothing (LOESS) analysis.

19. The method of claim 10 wherein the forming of a biohazard indicative conclusion, is based on steps selected from the group consisting of:

(1) selecting a given useful signal group and successively looking at next nearest neighbor useful signal groups until one of: (a) a count of likely biohazard presence exceeds a value N without a count of no likely biohazard presence exceeding a value M in which case a biohazard indicative conclusion of biohazard present is made, and (b) a count of no likely biohazard presence exceeds M, without a count of likely biohazard presence exceeding N, in which case the selecting and looking restarts with a new useful signal group having a likely biohazard presence indication and the counts for N and M are reset, with the process continuing until a conclusion is reached that is selected from the group consisting of: (i) a conclusion of biohazard presence is reached, and (ii) all useful signal groups have acted as a starting point with no conclusion of biohazard presence being reached, in which case a conclusion of no biohazard present is reached, wherein for (a) or (b), N is selected from the group consisting of: (i) at least 3, (ii) at least 5, (iii) at least 7, (iv) at least 9, (v) at least 11, (vi) at least 15, (vii) at least 25, and wherein M is selected from the group consisting of: (i) 0, (ii) at least 1, (iii) at least 10% of N, (iv) at least 20% of N, and (v) at least 30% of N;

(2) selecting a given useful signal group and successively looking at next nearest neighbor signal groups until a conclusion selected from the group consisting of: (a) a count of likely biohazard presence exceeds a value N without a count of no likely biohazard presence exceeding M, a count of unusable signal groups exceeding R, a count of groups having indeterminate biohazard status exceeding S, and a combined sum of at least two of M, R, and S exceeding an amount T, in which case a biohazard indicative conclusion of biohazard present is made, and (b) if conclusion under (a) is not met, the selecting and looking restarts with a new useful signal group having a likely biohazard presence indication and the counts of N, M, R, S are reset, with the process continuing until a conclusion is reached and selected from the group consisting: (i) a conclusion of biohazard present is reached, and (ii) all useful signal groups have acted as a starting point with no conclusion of biohazard presence being reached in which case a conclusion of no biohazard present is reached, wherein for (a) or (b) N is selected from the group consisting of: (i) at least 3, (ii) at least 5, (iii) at least 7, (iv) at least 9, (v) at least 11, (vi) at least 15, (vii) at least 25, and wherein M is selected from the group consisting of: (i) 0, (ii) at least 1, (iii) at least 10% of N, (iv) at least 20% of N, and (v) at least 30% of N, wherein R is selected from the group consisting of: (i) 0, (ii) at least 1, (iii) at least 10% of N, (iv) at least 20% of N, and (v) at least 30% of N, where S is selected from the group consisting of: (i) 0, (ii) at least 1, (iii) at least 10% of N, (iv) at least 20% of N, and (v) at least 30% of N, wherein T is selected from the group consisting of: (i) 0, (ii) at least 1, (iii) at least 10% of N, (iv) at least 20% of N, and (v) at least 30% of N; and (3) selecting a given useful signal group and successively looking at next nearest neighbor signal groups until a conclusion selected from the group consisting of: (a) a count of likely biohazard presence exceeds a value N without a count of no likely biohazard presence exceeding M, a count of unusable signal groups exceeding R, a count of groups having indeterminate biohazard statuses exceeding S, a combined sum associated with at least two of M, R, and S exceeding an amount T, and wherein the count of at least one of M, R, and S is reset to 0 when a count of successive nearest neighbors having likely biohazard presence status exceeds T, in which case a biohazard indicative conclusion of biohazard present is made, and (b) if any of M, R, S, or T is exceeded, the selecting and looking restarts with a new useful signal group having a likely biohazard presence indication, the counts of N, M, R, S, and T are reset, with the process continuing until a conclusion is reached and selected from the group consisting of: (i) a conclusion of biohazard present is reached, and (ii) all useful signal groups have acted as a starting point with no conclusion of biohazard presence being reached in which case a conclusion of no biohazard present is reached.

20. The method of claim 10 wherein the biohazard indicative conclusion indicating the presence of the biohazard requires the presence of a condition selected from the group consisting of:

(1) a plurality of neighboring biohazard indicative statuses each provide an indication of the likely presence of the biohazard, wherein a number of the plurality is selected from the group consisting of (a) at least three, (b) at least five, (c) at least seven, (d) at least ten, and (e) at least fifteen;

(2) at least N % of a plurality of nearest neighbor biohazard indicative statuses, provide an indication of the likely presence of the biohazard, wherein a number of the plurality is selected from the group consisting of (a) at least five, (b) at least seven, (c) at least 10, and (d) at least 15, and wherein N is selected from the group consisting of (i) greater than 50%, (ii) greater than 65%, (iii) greater than 80%, and (iv) greater than 90%;

(3) a plurality of nearest neighbor biohazard indicative statuses each provide an indication of the likely presence of the biohazard, with a possible exception that one such status may be selected from the group consisting of: (a) indeterminant presence of the biohazard, and (b) an indication of no likely presence of the biohazard, wherein a number of the plurality is selected from the group consisting of: (i) at least five, (ii) at least seven, (iii) at least ten, and (iv) at least fifteen;

(4) a plurality of K neighboring biohazard indicative statuses with each providing an indication of the likely presence of the biohazard, with a possible exception that a number of positions intermediate to the neighboring locations may not be indicative of likely presence wherein the number is no less than one but as high as a number, if higher than one, selected from the group consisting of: (a) less than 10% of K indicative of no likely presence, (b) less than 20% of K being indeterminant, and (c) less than 10% of K indicative of no likely presence and less than 20% of K being indeterminant, and wherein the number of the plurality is selected from the group consisting of: (i) at least five, (ii) at least seven, (iii) at least ten, and (iv) at least fifteen;

(5) M clusters of N biohazard likely indicative neighboring statuses from substantially non-overlapping sample positions, wherein M is at least two and N is at least three, and the sum of M and N is at least ten;

(6) at least M biohazard indicative statuses associated with a plurality of N different portions of the sample that are proximate to one another wherein the portions are physically separated by at least R exposure widths and no more than S exposure widths, wherein M is selected from the group consisting of: (a) at least 3, (b) at least 5, (c) at least 9, (d) at least 15, wherein N is selected from the group consisting of: (a) at least 50, (b) at least 100, (c) at least 200, (d) at least 400, and (e) at least 800, wherein R is selected from the group consisting of: (a) no less than $1/4$, (b) no less than $1/2$, (c) no less than $3/4$, (d) no less than 1; and wherein S is selected from the group consisting of: (a) no more than 2, (b) no more than 5, (c) no more than 10, and (d) no more than 20;

(7) a supermajority of N non-overlapping biohazard present indicative statuses provide an indicative status of likely positive presence, wherein the supermajority is selected from the group consisting of: (a) at least $2/3$ of N, (b) at least $3/4$ of N, (c) at least $4/5$ of N, (d) at least $5/6$ of N, (e) at least $6/7$ of N, (f) at least $7/8$ of N, (g) at least $8/9$ of N, and (h) at least $9/10$ of N, and wherein N is selected from the group consisting of: (i) at least 5, (ii) at least 7, (iii) at least 11, (iv) at least 15, and (v) at least 25; and (8) a plurality of at least F out of FF neighboring biohazard present indicative statuses from useful signal groups provide indications of likely biohazard presence based on native fluorescence emission detections and a plurality of at least R out of RR neighboring biohazard present indicative statuses from useful signal groups provide indications of likely biohazard presence based on Raman emission detections where the positions of the R indicative statuses are common with the positions of the respective F indicative statuses, wherein (i) the ratio of F/to R is selected from the group consisting of: (a) at least 3/2, (b) at least 5/3, (c) at least 9/7, (d) at least 15/11, and wherein (ii) FF and RR are each selected from the group consisting of: (a) at least 20 locations, (b) at least 50 locations, (c) at least 100 locations, (d) at least 200 locations, (e) at least 400 locations, and (f) at least 800 locations.

21. The method of claim 10 wherein the housing additionally holds a programmed processor for controlling the excitation radiation source, the relative moving of the beam of excitation radiation and the sample, the at least one detector; and a memory for storing emission radiation detection signals and associated positioning information, and wherein the housing additionally holds at least one programmed processor and at least one memory for providing at least a plurality of functions selected from the group consisting of: (1) storing predetermined biohazard indicative signal information, (2) storing predetermined non-biohazard indicative signal information, (3) storing background signal information, (4) processing information to produce useful detection signal information, (5) processing information to produce a plurality of biohazard indicative statuses, and (6) processing information to produce a biohazard indicative conclusion.

22. The method of claim 10 additionally comprising: an imaging camera that provides an image from a sample location selected from the group consisting of: (1) an image from visible reflected radiation, (2) an image from transmitted visible radiation, (3) an image from visible radiation created by excitation, (4) an image from selected visible reflected radiation, (5) an image from selected transmitted visible radiation, (6) an image from selected visible radiation created by excitation, (7) an image from UV reflected radiation, (8) an image from transmitted UV radiation, (9) an image from UV radiation created by excitation, (10) an image from selected UV reflected radiation, (11) an image from selected transmitted UV radiation, (12) an image from selected UV radiation created by excitation, (13) an image from IR reflected radiation, (14) an image from transmitted IR radiation, (15) an image from IR radiation created by excitation, (16) an image from selected IR reflected radiation, (17) an image from selected transmitted IR radiation, (18) an image from selected NIR radiation created by excitation, (19) an image from NIR reflected radiation, (20) an image from transmitted NIR radiation, (21) an image from NIR radiation created by excitation, (22) an image from selected NIR reflected radiation, (23) an image from selected transmitted NIR radiation; and further comprises a display for visually viewing the provided image from the sample location.

23. The method of claim 10 wherein the volume of the housing is selected from the group consisting of: (1) less than 500 liters, (2) less than 50 liters, (3) less than 20 liters, (4) less than 10 liters, (5) less than 5 liters, and (6) less than 2 liters; wherein the mass of the housing and its contents is selected from the group consisting of: (1) less than 50 Kg, (2) less than 25 Kg, (3) less than 10 Kg, (4) less than 5 Kg, (5) less than 3 Kg, and (6) less than 2 Kg; and wherein the power consumed by components within the housing is selected from the group consisting of: (1) less than 500 W, (2) less than 200 W, (3) less than 100 W, (4) less than 50 W, and (5) less than 20 W.

\* \* \* \* \*